US011723987B2

(12) United States Patent
Dominguez-Bendala

(10) Patent No.: US 11,723,987 B2
(45) Date of Patent: Aug. 15, 2023

(54) DOUBLE SUICIDE GENE VECTOR SYSTEMS FOR STEM CELLS

(71) Applicant: UNIVERSITY OF MIAMI, Miami, FL (US)

(72) Inventor: Juan Dominguez-Bendala, Miramar, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 597 days.

(21) Appl. No.: 16/333,962

(22) PCT Filed: Sep. 15, 2017

(86) PCT No.: PCT/US2017/051847
§ 371 (c)(1),
(2) Date: Mar. 15, 2019

(87) PCT Pub. No.: WO2018/053306
PCT Pub. Date: Mar. 22, 2018

(65) Prior Publication Data
US 2019/0247518 A1 Aug. 15, 2019

Related U.S. Application Data

(60) Provisional application No. 62/394,977, filed on Sep. 15, 2016.

(51) Int. Cl.
| | |
|---|---|
| *A61K 48/00* | (2006.01) |
| *A61P 1/16* | (2006.01) |
| *A61K 9/00* | (2006.01) |
| *A61P 25/28* | (2006.01) |
| *A61P 3/10* | (2006.01) |
| *A61P 35/00* | (2006.01) |
| *C12N 15/86* | (2006.01) |
| *C12N 15/85* | (2006.01) |

(52) U.S. Cl.
CPC ........ *A61K 48/0058* (2013.01); *A61K 9/0019* (2013.01); *A61K 48/00* (2013.01); *A61K 48/0066* (2013.01); *A61P 1/16* (2018.01); *A61P 3/10* (2018.01); *A61P 25/28* (2018.01); *A61P 35/00* (2018.01); *C12N 15/85* (2013.01); *C12N 15/86* (2013.01)

(58) Field of Classification Search
CPC .. A61K 48/0058; A61K 9/0019; A61K 48/00; A61K 48/0066; A61P 25/28; A61P 1/16; A61P 3/10; A61P 35/00; C12N 15/85; C12N 15/86
See application file for complete search history.

(56) References Cited

U.S. PATENT DOCUMENTS

| | | | | |
|---|---|---|---|---|
| 6,537,805 | B1 * | 3/2003 | Melchner | C12N 15/63 |
| | | | | 435/320.1 |
| 2006/0068496 | A1 * | 3/2006 | Kelly | A61P 43/00 |
| | | | | 435/455 |
| 2011/0178282 | A1 | 7/2011 | Freytag et al. | |
| 2015/0079682 | A1 * | 3/2015 | Lu | C12N 15/85 |
| | | | | 435/465 |

FOREIGN PATENT DOCUMENTS

WO  WO-9938964 A3 * 1/2000 ............ A61P 35/00

OTHER PUBLICATIONS

Keith N, Bilsland AE, Anderson CJ, Monaghan AJ, Plumb JA. 336. Telomerase-Directed Suicide Gene Therapy: An Analysis of hTR and hTERT Promoters. Molecular Therapy. May 2003;7(5) (Year: 2003).*
Schuldiner M, Itskovitz-Eldor J, Benvenisty N. Selective ablation of human embryonic stem cells expressing a "suicide" gene. Stem cells. May 2003;21(3):257-65. (Year: 2003).*
Li W, Xiang AP. Safeguarding clinical translation of pluripotent stem cells with suicide genes. Organogenesis. Jan. 1, 2013 ;9(1):34-9. (Year: 2013).*
Navarro SA, Carrillo E, Griñán-Lisón C, Martín A, Peran M, Marchal JA, Boulaiz H. Cancer suicide gene therapy: a patent review. Expert opinion on therapeutic patents. Sep. 1, 2016;26(9):1095-104. (Year: 2016).*
Jiang, J., Wei, D., Sun, L., Wang, Y., Wu, X., Li, Y., Fang, Z., Shang, H., Wei, Z."A preliminary study on the construction of double suicide gene delivery vectors by mesenchymal stem cells and the in vitro inhibitory effects on SKOV3 cells". Oncology Reports 31, No. 2 (2014): 781-787 (Year: 2014).*
Ma Y, Zhang P, Wang F, Yang J, Yang Z, Qin H. The relationship between early embryo development and tumourigenesis. Journal of cellular and molecular medicine. Dec. 2010;14(12):2697-701. (Year: 2010).*
Yi BR, Choi KJ, Kim SU, Choi KC. Therapeutic potential of stem cells expressing suicide genes that selectively target human breast cancer cells: evidence that they exert tumoricidal effects via tumor tropism. International journal of oncology. Sep. 1, 2012;41(3):798-804 (Year: 2012).*
Ulasov IV, Borovjagin AV, Schroeder BA, Baryshnikov AY. Oncolytic adenoviruses: a thorny path to glioma cure. Genes & diseases. Dec. 1, 2014;1(2):214-26 (Year: 2014).*

(Continued)

*Primary Examiner* — James D Schultz
(74) *Attorney, Agent, or Firm* — Marshall, Gerstein & Borun LLP

(57) ABSTRACT

Provided herein are recombinant expression vector systems for expression by stem cells that allow for selective elimination of stem cell-derived tumorigenic cells, while preserving stem cell-derived therapeutic cells. The systems provided herein provide a means by which modified stem cells can be safely transplanted into subjects. In exemplary embodiments, the system comprises at least two suicide genes, one of which is specifically inactivated in cells exhibiting the desired phenotype and one of which is activated when the cell comprising the recombinant expression vector system behaves similarly to or the same as a tumor cell.

11 Claims, 20 Drawing Sheets

Specification includes a Sequence Listing.

(56) References Cited

OTHER PUBLICATIONS

Kaltschmidt C, Kaltschmidt B, Neumann H, Wekerle H, Baeuerle PA. Constitutive NF-kappa B activity in neurons. Molecular and cellular biology. Jun. 1994;14(6):3981-92 (Year: 1994).*
Dorer DE, Nettelbeck DM. Targeting cancer by transcriptional control in cancer gene therapy and viral oncolysis. Advanced drug delivery reviews. Jul. 2, 2009;61(7-8):554-71 (Year: 2009).*
Albanell et al., Telomerase activity in germ cell cancers and mature teratomas, *J. Natl. Cancer Inst*. 91:1321-6 (1999).
Ausubel, Current Protocols in Molecular Biology, John Wiley & Sons, Hoboken, NJ (1995).
Bartlett et al., Report from IPITA-TTS Opinion Leaders Meeting on the Future of β-Cell Replacement, *Transplantation*. 100 Suppl 2:S1-44 (2016).
Baum et al., Mutagenesis and oncogenesis by chromosomal Insertion of gene transfer vectors, *Hum. Gene. Ther.* 17:253-63 (2006).
Behar et al., Curr. Protoc. Stem Cell Biol. Chapter 1, Unit 1C 13 (2012).
Belteki et al., Conditional and Inducible transgene expression in mice through the combinatorial use of Cre-mediated recombination and tetracycline induction, *Nucleic Acids Res.* 33:e51 (2005).
Black et al., Herpes simplex virus-1 thymidine kinase mutants created by semi-random sequence mutagenesis improve prodrug-mediated tumor cell killing, *Cancer Res.* 61:3022-6 (2001).
Blum et al., The anti-apoptotic gene survivin contributes to teratoma formation by human embryonic stem cells, *Nat. Biotechnol.* 27:281-7 (2009).
Bridgewater et al., Expression of the bacterial nitroreductase enzyme in mammalian cells renders them selectively sensitive to killing by the prodrug CB1954, *Eur. J. Cancer.* 31A:2362-70 (1995).
Carbrera et al., The unique cytoarchitecture of human pancreatic islets has implications for islet cell function, *Proc. Natl. Acad. Sci. USA.* 103:2334-9 (2006).
Cechin et al., Influence of in vitro and in vivo oxygen modulation on β cell differentiation from human embryonic stem cells, *Stem Cells Transl. Med.* 3:277-89 (2014).
Clark et al., Selective cell ablation in transgenic mice expression *E. coli* nitroreductase, *Gene Ther.* 4:101-10 (1997).
Davis et al., Oncolysis and suppression of tumor growth by a GFP-expressing oncolytic adenovirus controlled by an hTERT and CMV hybrid promoter, *Cancer Gene Ther.* 13:720-3 (2006).
Dominguez-Bendala et al., The Human Endocrine Pancreas: New Insights on Replacement and Regeneration, *Trends Endocrinol. Metab.* 27:153-162 (2016).
Drabek et al., The expression of bacterial nitroreductase in transgenic mice results in specific cell killing by the prodrug CB1954, *Gene Ther.* 4:93-100 (1997).
Elion et al., The chemotherapeutic exploitation of virus-specified enzymes, *Adv. Enzyme Regul.* 18:53-66 (1980).
Fareed et al., Suicide gene transduction sensitizes murine embryonic and human mesenchymal stem cells to ablation on demand—a fail-safe protection against cellular misbehavior, *Gene Ther.* 9:955-62 (2002).
Felmer et al., The gene suicide system Ntr/CB1954 causes ablation of differentiated 3T3L1 adipocytes by apoptosis, *Biol. Res.* 37:449-60 (2004).
Fox et al., FDA scrutinizes human stem cell therapies, *Nat. Biotechnol.* 26:598-99 (2008).
Fraker et al., A physiological pattern of oxygenation using perfluorocarbon-based culture devices maximizes pancreatic islet viability and enhances β-cell function, *Cell Transplant.* 22:1723-33 (2013).
Fraker et al., Enhanced oxygenation promotes beta-cell differentiation in vitro, *Stem Cells.* 25:3155-64 (2007).
Fraker et al., Oxygen: a master regulator of pancreatic development? *Biol. Cell.* 101:431-40 (2009).
Fujikawa et al., Teratoma formation leads to failure of treatment for type I diabetes using embryonic stem cell-derived insulin-producing cells, *Am. J. Pathol.* 166:1781-91 (2005).
Grove et al., Virus-directed enzyme prodrug therapy using CB1954, *Anticancer Drug Des.* 14:461-72 (1999).
Hansson et al., Artifactual insulin release from differentiated embryonic stem cells, *Diabetes.* 53:2603-9 (2004).
Hori et al., Growth inhibitors promote differentiation of insulin-producing tissue from embryonic stem cells, *Proc. Natl. Acad. Sci. USA.* 99:16105-10 (2002).
International Preliminary Report on Patentability, PCT/US2017/051847 (dated Mar. 19, 2019).
International Search Report and Written Opinion, PCT/US2017/051847 (dated Dec. 4, 2017).
Irion et al., Identification and targeting of the ROSA26 locus in human embryonic stem cells, *Nat. Biotechnol.* 25:1477-82 (2007).
Jiang et al., A preliminary study on the construction of double suicide gene delivery vectors by mesenchymal stem cells and the in vitro inhibitory effects on SKOV3 cells, *Oncol. Rep.* 31:781-7 (2014).
Kamani et al., Unrelated donor cord blood transplantation for children with severe sickle cell disease: results of one cohort from the phase II study from the Blood and Marrow Transplant Clinical Trials Network (BMT CTN), *Biol. Blood. Marrow Transplant.* 18:1265-72 (2012).
Karjoo et al., Progress and problems with the use of suicide genes for targeted cancer therapy, *Adv. Drug Deliv. Rev.* 99:113-28 (2016).
Karussis et al., Safety and immunological effects of mesenchymal stem cell transplantation in patients with multiple sclerosis and amyotrophic lateral sclerosis, *Arch. Neurol.* 67:1187-94 (2010).
Klatzmann et al., A phase I/II dose-escalation study of herpes simplex virus type 1 thymidine kinase "suicide" gene therapy for metastatic melanoma. Study Group on Gene Therapy of Metastatic Melanoma, *Hum. Gene Ther.* 9:2585-94 (1998).
Kos et al., Cre/loxP system for generating tissue-specific knockout mouse models, *Nutr. Rev.* 62:243-6 (2004).
Kozak, An analysis of 5'-noncoding sequences from 699 vertebrate messenger RNAs, *Nucliec Acids Res.* 15:8125-48 (1987).
Kroon et al., Pancreatic endoderm derived from human embryonic stem cells generates glucose-responsive insulin-secreting cells in vivo, *Nat. Biotechnol.* 26:443-52 (2008).
Kuhn et al., Cre/loxP recombination system and gene targeting, *Methods Mol. Biol.* 180:175-204 (2002).
Lanzoni et al., Concise review: clinical programs of stem cell therapies for liver and pancreas, *Stem Cells.* 31:2047-60 (2013).
Mikkers et al., Retroviral insertional mutagenesis: tagging cancer pathways, *Adv. Cancer Res.* 88:53-99 (2003).
Moolten, Tumor chemosensitivity conferred by inserted herpes thymidine kinase genes: paradigm for a prospective cancer control strategy, *Cancer Res.* 46:5276-81 (1986).
Nagy et al., Cre recombinase: the universal reagent for genome tailoring, *Genesis.* 26:99-109 (2000).
Nishiyama et al., Anticellular effects of 9-(2-hydroxyethoxymethyl) guanine against herpes simplex virus-transformed cells, *J. Gen. Virol.* 45:227-30 (1979).
Odagiri et al., Function of the human insulin promoter in primary cultured islet cells, *J .Biol. Chem.* 271:1909-15 (1996).
Odorico et al., Multilineage differentiation from human embryonic stem cell lines, *Stem Cells.* 19:193-204 (2001).
Pagliuca et al., Generation of functional human pancreatic β cells in vitro, *Cell.* 159:428-39 (2014).
Pennacchio et al., Enhancers: five essential questions., *Nat. Rev. Genet.* 14:288-95 (2013).
Qasim et al., T cell transduction and suicide with an enhanced mutant thymidine kinase, *Gene Ther.* 9:824-7 (2002).
Qin et al., Systematic comparison of constitutive promoters and the doxycycline-inducible promoter, *PLoS One.* 5:e10611 (2010).
Rezania et al., Enrichment of human embryonic stem cell-derived NKX6.1-expressing pancreatic progenitor cells accelerates the maturation of insulin-secreting cells in vivo, *Stem Cells.* 31:2432-42 (2013).
Rezania et al., Reversal of diabetes with insulin-producing cells derived in vitro from human pluripotent stem cells, *Nat. Biotechnol.* 32:1121-33 (2014).

(56) References Cited

OTHER PUBLICATIONS

Russ et al., Controlled induction of human pancreatic progenitors produces functional beta-like cells in vitro, *EMBO J.* 34:1759-72 (2015).
Schipper et al., Evaluation of herpes simplex virus 1 thymidine kinase-mediated trapping of (131)I FIAU and prodrug activation of ganciclovir as a synergistic cancer radio/chemotherapy, *Mol. Imaging Biol.* 9:110-6 (2007).
Schuldiner et al., Effects of eight growth factors on the differentiation of cells derived from human embryonic stem cells., *Proc. Natl. Acad. Sci. USA.* 97:11307-12 (2000).
Schuldiner et al., Selective ablation of human embryonic stem cells expressing a "suicide" gene, *Stem Cells.* 21:257-65 (2003).
For production of functional pancreatic progenitors from human embryonic stem cells, *PLoS One.* 7:e7004 (2012).
Searle et al., Nitroreductase: a prodrug-activating enzyme for cancer gene therapy, *Clin. Exp. Pharmacol. Physiol.* 31:811-6 (2004).
Sipione et al., Insulin expressing cells from differentiated embryonic stem cells are not beta cells, *Diabetologia.* 47:499-508 (2004).
Methods and Reviews, Cancer Research UK Centre for Cancer Therapeutics at the Institute of Cancer Research, Humana Press (2004).
Tamada et al., Molecular targeting of pancreatic disorders, *World J. Surg.* 29:325-33 (2005).
Tedesco et al., Transplantation of genetically corrected human iPSC-derived progenitors in mice with limb-girdle muscular dystrophy, *Sci. Transl. Med.* 4:140ra89 (2012).
Thomson et al., Embryonic stem cell lines derived from human blastocysts, *Science.* 282:1145-7 (1998).
Tian et al., Human telomerase reverse-transcriptase promoter-controlled and herpes simplex virus thymidine kinase-armed adenoviruses for renal cell carcinoma treatment, *Onco. Targets Ther.* 6:419-26 (2013).
Vegas et al., Long-term glycemic control using polymer-encapsulated human stem cell-derived beta cells in immune-competent mice, *Nat. Med.* 22:306-11 (2016).
Vogel, Cell biology. Ready or not? Human ES cells head toward the clinic, *Science.* 308:1534-8 (2005).
Wang et al., Specific gene expression and therapy for pancreatic cancer using the Cytosine deaminase gene directed by the ray insulin promoter, *J. Gastrointest. Surg.* 8:98-108 (2004).
Williams et al., Nitroreductase gene-directed enzyme prodrug therapy: insights and advances toward clinical utility, *Biochem. J.* 471:131-53 (2015).
Yazawa et al., Current progress in suicide gene therapy for cancer, *World J. Surg.* 26:783-9 (2002).
Yoshihara et al., ERRγ is Required for the Metabolic Maturation of Therapeutically Functional Glucose-Responsive β Cells, *Cell Metab.* 23:622-34 (2016).
Yoshimura et al. Application of Cre-loxP system to the urinary tract and cancer gene therapy, *Mol. Urol.* 5:81-4 (2001).
Ikegami et al., "Development of Gene Therapy Using Prostate-specific Membrane Antigen Promoter/Enhancer with Cre Recombinase/LoxP System for Prostate Cancer Cells Under Androgen Ablation Condition", Japanese Journal of Cancer Research, vol. 93, No. 10, pp. 1154-1163 (Oct. 1, 2002).
Luo et al., "Targeted killing effects of double CD and TK suicide genes controlled by surviving promoter on gastric cancer cell", Molecular Biology Reports; an International Journal on Molecular and Cellular Biology, Kluwer Academic Publishers, DO, vol. 38, No. 2, pp. 1201-1207 (Jun. 24, 2010).
Plumb et al., "Telomerase-specific suicide gene therapy vectors expressing bacterial nitroreductase sensitize human cancer cells to the prodrug CB1954", Oncogene, vol. 20, No. 53, pp. 7797-7803 (Nov. 1, 2001).

\* cited by examiner

FIG. 7a
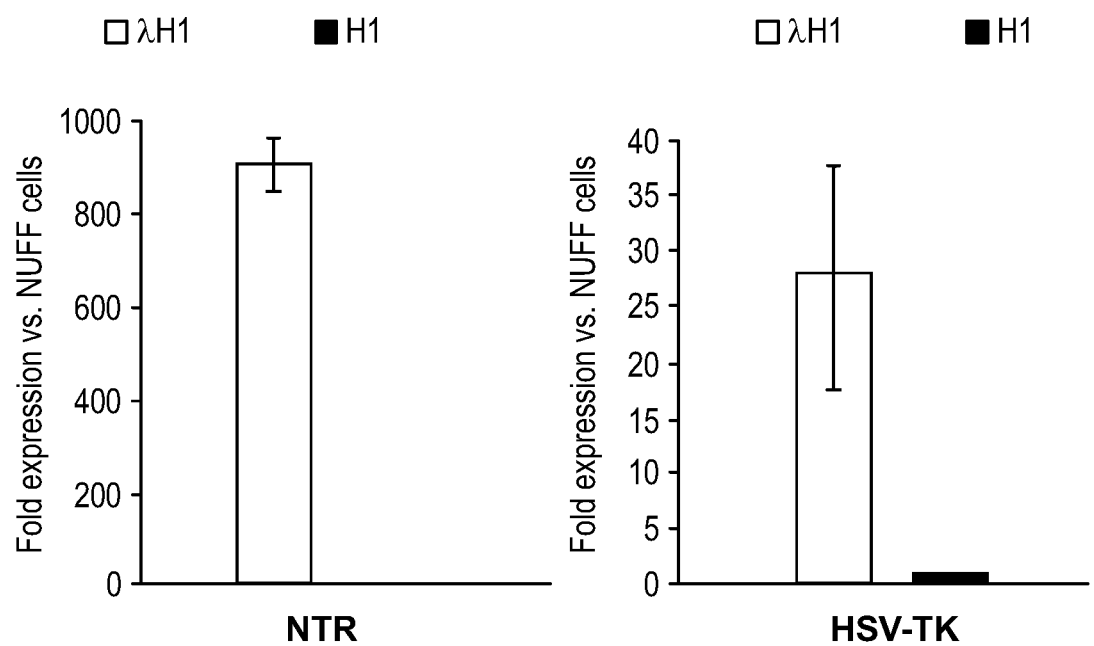
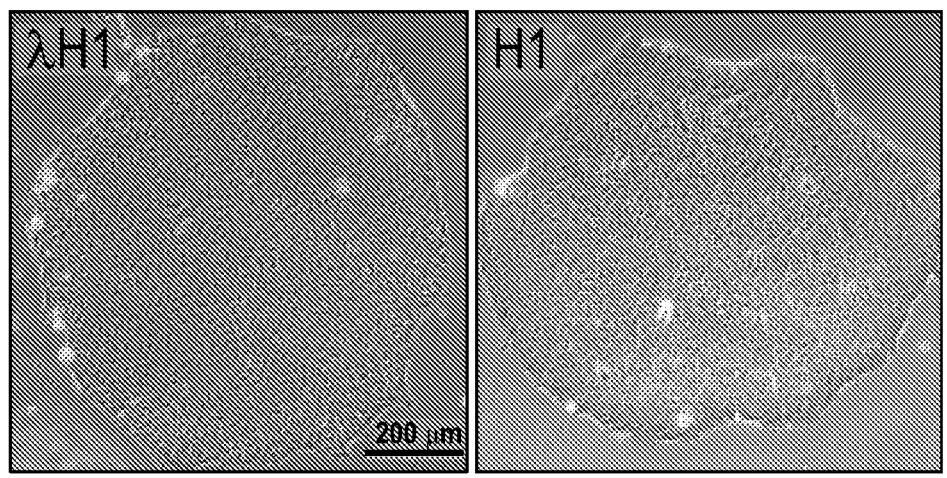
FIG. 7b

FIG. 10c
FIG. 10d
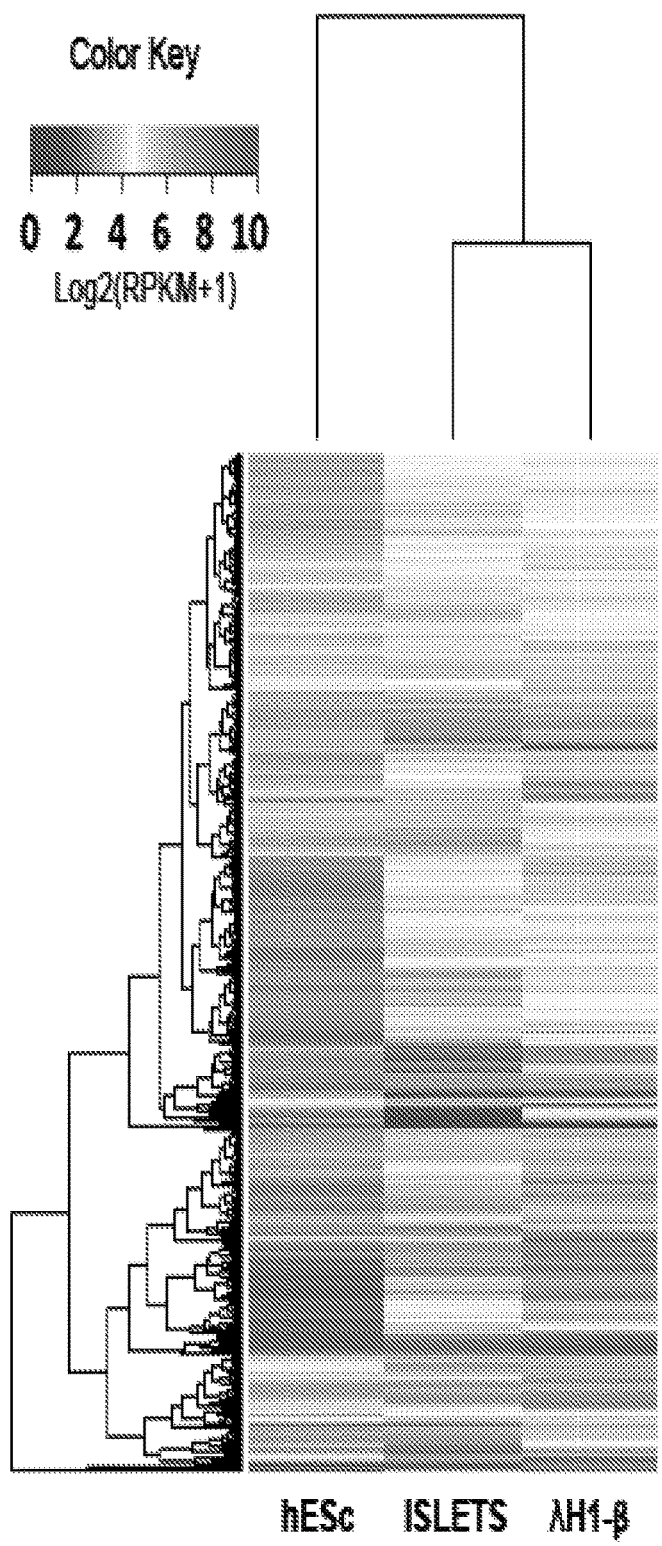
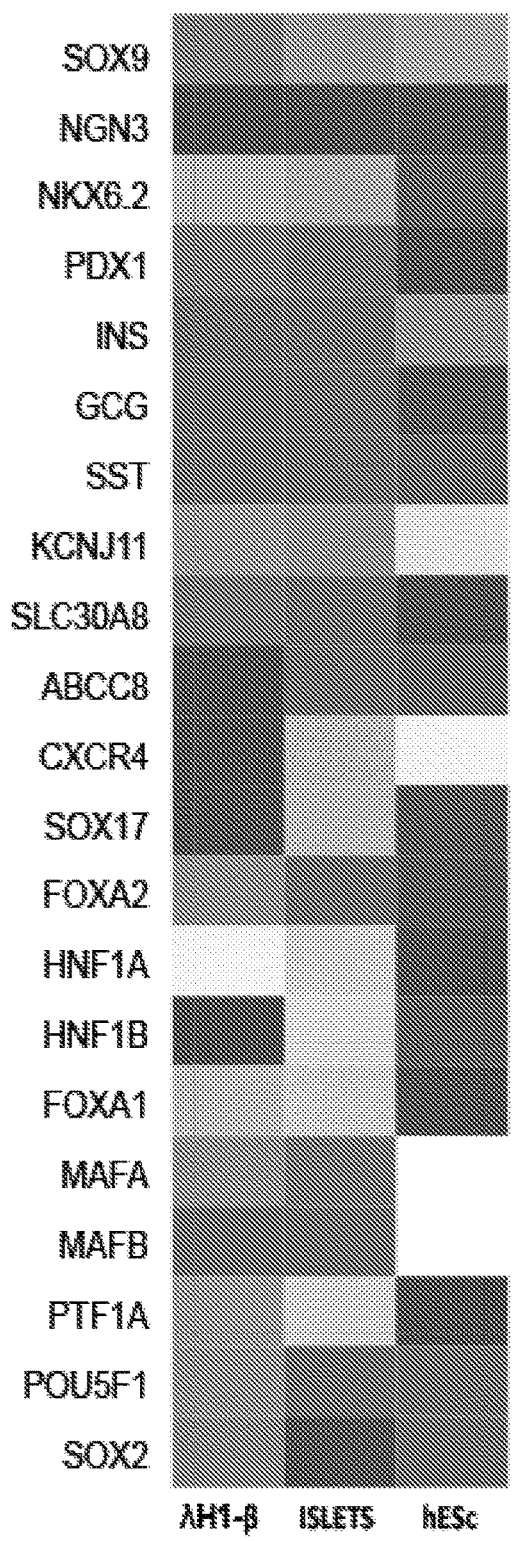

DOUBLE SUICIDE GENE VECTOR SYSTEMS FOR STEM CELLS

CROSS-REFERENCE TO RELATED APPLICATIONS

This application claims priority to U.S. Provisional Patent Application No. 62/394,977, filed Sep. 15, 2016, which is incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 48,000 byte ACII (Text) file named "51087A_SeqListing.txt"; created on Sep. 14, 2017.

BACKGROUND

Islet transplantation is an effective cell therapy for type 1 diabetes (T1D), but its clinical application is limited by the shortage of donors. Among all alternative sources of islets, the differentiation of human pluripotent stem cells (hPSCs), chiefly human embryonic stem cells (hESc), has taken an early lead. The initiation of nationwide Phase I/II clinical trials for T1D using hESc-derived pancreatic progenitors by Viacyte, Inc. (based on [1,2]), as well as the recent publication of key advances in the maturation of functional β-cells in vitro[3-8] have galvanized the field. However, while the proportion of β-like cells obtained through state-of-the-art terminal differentiation methods is relatively high (30-40%) [4,5] a significant percentage of undefined non-endocrine cell types are also generated[4,9]. Most importantly, there is the potential for carry-over of non-differentiated cell types that may produce teratomas upon transplantation. The formation of complex teratomas consisting of derivatives from the three germ layers was the result of transplantation of hPSC into immunodeficient rodents. In fact, the test for teratoma formation is routinely used to test the pluripotency of hESc (and more recently, iPSc)[10]. In the context of hPSC-based clinical therapies, the formation of teratomas would obviously be an undesired occurrence. As differentiation is hardly a synchronous process, teratomas tend to arise either from carry-over undifferentiated cells or from cells that de-differentiate upon transplantation[11-14]. They are common in protocols in which non-terminally differentiated cells are allowed to mature in vivo[1]. The formation of teratomas is a major cause of concern for regulatory agencies[15].

Although refinements of the prevailing differentiation protocols have significantly reduced this risk in preclinical studies, the foreseeable implementation of hPSC-based therapies in thousands of patients calls for caution. One single case of hPSC-derived tumors in patients may set the entire field back for years.

Some research groups have approached the problem of hPSC tumorigenesis by screening the number of undifferentiated cells in each transplantable preparation. If such number is below the threshold known to produce teratomas in immunodeficient mice, they argue, these preparations should be considered safe for clinical use[34]. However, this method does not take into account the risk of de-differentiation after transplantation[11]. hPSC-based therapies are predicted to reach millions of patients in the near future. It would take only one incidence of tumorigenesis to bring the entire field to a screeching halt, perhaps for years. For this reason, other groups have proposed the use of engineered hPSC with integrated safeguards, namely suicide genes. However, the pro-drug to which the suicide genes confer sensitivity, kill the whole graft, including the cells for which there was a need in the first place. Considering the frequency at which teratogenic lesions are observed in numerous experimental conditions, such safeguard would render the entire approach impractical.

Thus, there is a need for means by which modified hESc and induced pluripotent stem cell (iPSc) lines that can be efficiently differentiated and safely transplanted. There is a need for a means by which "good" cells are selectively preserved, while cells with tumorigenic potential are destroyed.

SUMMARY

The present disclosure provides a recombinant expression vector system that provides an integrated fail-safe mechanism that allows for selective elimination of tumorigenic cells while preserving cells of therapeutic value, thereby providing a means by which modified stem cells can be safely transplanted into subjects in need therefor.

In exemplary embodiments, the recombinant expression vector system comprises at least two suicide genes, one of which is specifically inactivated in cells exhibiting the desired phenotype. In exemplary embodiments, the recombinant expression vector system comprises at least two suicide genes, one of which is specifically excised, removed or deleted in cells exhibiting the desired phenotype. In exemplary embodiments, the recombinant expression vector system comprises at least two suicide genes, one of which is specifically excised, removed or deleted via action of a recombinase in cells exhibiting the desired phenotype. In exemplary aspects, at least one of the two suicide genes is activated when the cell the recombinant expression vector system behaves similarly to or the same as a tumor cell. In exemplary aspects, the expression of at least one of the two suicide genes is controlled by a promoter which is highly active in a tumor or cancer cell.

In exemplary aspects, the recombinant expression vector system of the present disclosure comprises at least one suicide gene located between two loxP sites, two HIV markers, or two FRT sites. In exemplary aspects, the recombinant expression vector system comprises a nucleic acid encoding a recombinase, including, e.g., FLT, Cre, Tre. In exemplary aspects, expression of the nucleic acid encoding the Cre recombinase is controlled by a promoter which is tissue-specific or hormone-responsive. In exemplary aspects, the recombinant expression vector system comprises a telomerase promoter controlling the expression of at least one suicide gene.

Also provided by the present disclosure is a host cell comprising any one of the recombinant expression vector systems described herein, and kits comprising such host cells or recombinant expression vector systems. In exemplary embodiments, the kit comprises at least one agent which causes cell death to cells expressing a suicide gene.

Further provided is a method of producing stem cells suitable for transplantation into a subject. In exemplary embodiments, the method comprising contacting a cell culture comprising stems cells with any one of the recombinant expression vector systems described herein and adding to the cell culture an agent which causes cell death to cells expressing a suicide gene or an agent which causes cell death or to cells not expressing a selectable marker.

Furthermore provided is a method of transplanting stem cells to a subject in need thereof, comprising administering to the subject stem cells comprising the recombinant expression vector system of the present disclosure and administering to the subject an agent which causes cell death to cells expressing a suicide gene. Without being bound to a particular theory, the administration, e.g., transplantation, of such stem cells with the recombinant expression vector of the present disclosure provides cells which differentiate into cells having therapeutic value. Thus, the administration, e.g., transplantation, of such stem cells with the recombinant expression vector of the present disclosure provides therapeutic treatment of the subject. Accordingly, the present disclosure provides methods of treating a disease in a subject in need thereof, comprising administering, e.g., transplanting, stem cells with the recombinant expression vector of the present disclosure in an amount effective to treat the disease.

BRIEF DESCRIPTION OF THE DRAWINGS

FIG. 6 is a set of illustrations that depict the general strategy to genetically modify pluripotent stem cells with suicide gene constructs designed to selectively preserve the cells of the desired phenotype and kill cells with tumorigenic potential.

FIG. 7A is a set of graphs demonstrating that λH1 cells (also referred to herein as "H1.1 cells"), but not H1 cells, express both the nitroreducatse (NTR) and Herpes Simplex Virus Thymidine Kinase (HSV-TK) transgenes. FIG. 7B is a pair of photographs showing the morphology of λH1 colonies.

FIG. 10C is a comparison of specific pancreatic markers between islets and λH1-derived and selected β-like cells. FIG. 10D is a depiction that confirms the overall similitude of their transcriptional profile.

DETAILED DESCRIPTION

Figure 1:
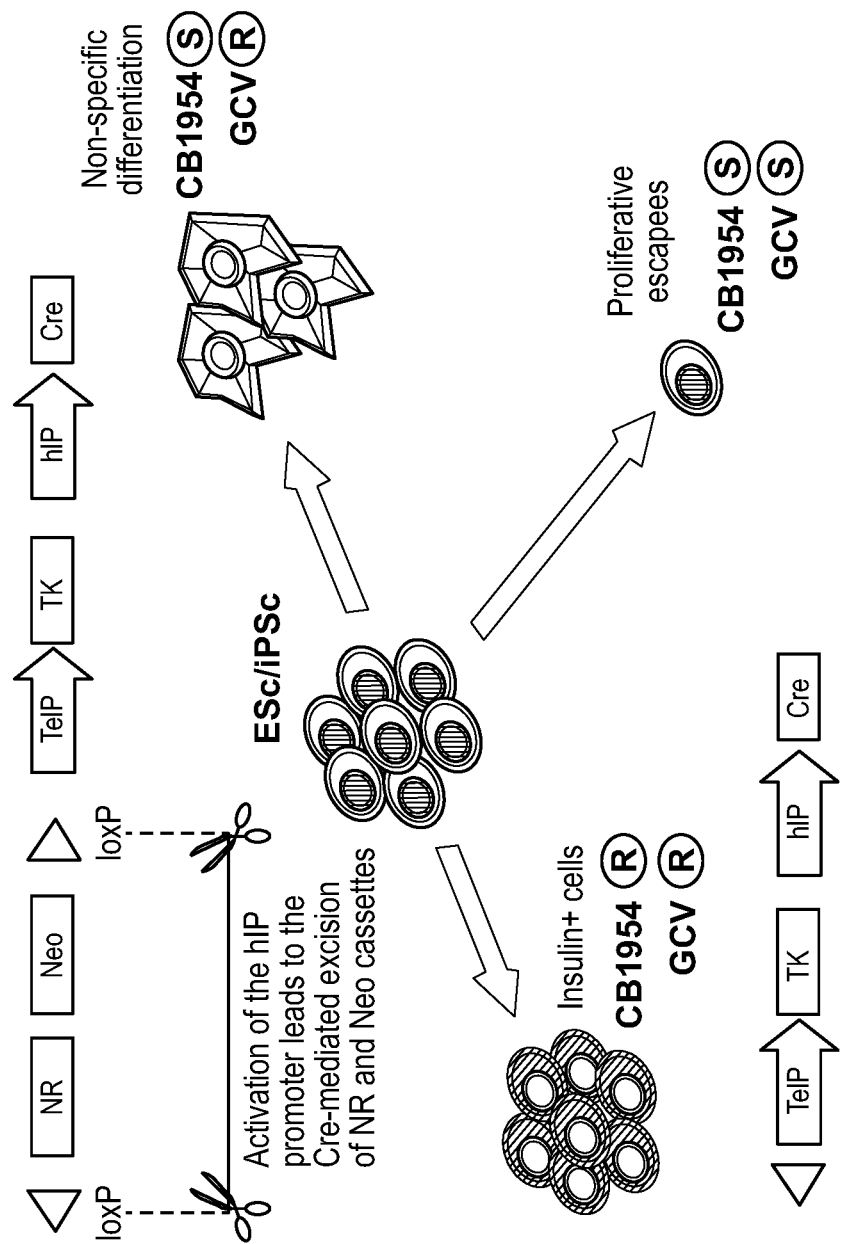
FIG. 1 is an illustration depicting a mechanism of action relating to engineered human pluripotent stem cell (hPSCs), which can be used for β-cell differentiation protocols, which also yield other cell types (non-specific differentiation) and, potentially, proliferative escapees. The construct pictured at the top is designed so that a loxP-flanked suicide gene (nitroreductase, NR) will be selectively excised out in insulin-expressing cells by virtue of the expression of Cre recombinase placed under the control of the insulin promoter. A second suicide gene (thymidine kinase, TK), which is expressed only in telomerase$^+$ cells (TeIP promoter), remains silent in β-cells. As a consequence, only insulin$^+$ cells will be resistant to both CB1954 (the pro-drug activated by NR activity) and GCV (the pro-drug activated by TK). All other possible outcomes bring about the expression of one or both suicide genes. Neo=neomycin resistance cassette (SV40 promoter); NR=nitroreductase cassette (CMV promoter); TeIP=telomerase promoter; TK=HSV thymidine kinase; hIP=human insulin promoter; Cre=Cre recombinase; S=sensitive; R=resistant.

The present disclosure provides a recombinant expression vector system providing an integrated fail-safe mechanism that will allow for selective elimination of tumorigenic cells while preserving cells of therapeutic value, thereby allowing a means by which modified stem cells can be safely transplanted into subjects in need therefor.

As used herein, the term "recombinant expression vector system" refers to one recombinant expression vector comprising all components or a set of two or more recombinant expression vectors designed to function together. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the disclosure are not naturally-occurring as a whole. However, parts of the vectors can be naturally-occurring. The inventive recombinant expression vectors in exemplary aspects comprise any type of nucleotides, including, but not limited to DNA and RNA, which may be single-stranded or double-stranded, synthesized or obtained in part from natural sources, and which in exemplary aspects contain natural, non-natural or altered nucleotides. The recombinant expression vectors in exemplary aspects comprise naturally-occurring or non-naturally-occurring internucleotide linkages, or both types of linkages. In exemplary aspects, the altered nucleotides or non-naturally occurring internucleotide linkages do not hinder the transcription or replication of the vector.

The recombinant expression vector system of the present disclosure may comprise any suitable recombinant expression vector, and may be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). In exemplary aspects, the recombinant expression vector system of the present disclosure comprises one or more vectors comprising all or part of pUC57 (GenScript; Piscataway, N.J.) or all or part of pPUR (Clontech; Mountainview; CA). Bacteriophage vectors, such as λGT10, λGT11, λZapII (Stratagene), λEMBL4, and λNMI 149, also can be used. Examples of plant expression vectors include pBIOI, pBI101.2, pBI101.3, pBI121 and pBIN19 (Clontech). Examples of animal expression vectors include pEUK-CI, pMAM and pMAMneo (Clontech). In exemplary aspects, the recombinant expression vector is a viral vector, e.g., a retroviral vector, an adenovirus vector, an adeno-associated virus (AAV) vector, or a lentivirus vector.

The recombinant expression vectors and systems comprising the same of the present disclosure can be prepared using standard recombinant DNA techniques described in, for example, Maniatis and Sambrook, *Molecular Cloning: A laboratory manual*, $4^{th}$ ed., Cold Spring Harbor, N.Y., Cold Spring Harbor Laboratory (2014) and Ausubel, *Current Protocols in Molecular Biology* John Wiley & Sons, Hoboken, N.J., (1995). Constructs of expression vectors, which are circular or linear, can be prepared to contain a replication system functional in a prokaryotic or eukaryotic host cell. Replication systems can be derived, e.g., from ColEI, 2μ plasmid, λ, SV40, bovine papilloma virus, and the like. In exemplary aspects, the recombinant expression vector system comprises an ori sequence which signals for the origin of replication. In exemplary aspects, the ori comprises a sequence of SEQ ID NO: 10, 19, or 27, or a combination thereof.

In exemplary aspects, the recombinant expression vector system comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In exemplary aspects, the recombinant expression vector system comprises a polyadenylation signal (poly(A) signal). In exemplary aspects, the recombinant expression vector system comprises several poly(A) signals. In exemplary aspects, the poly(A) signal is a bovine growth hormone poly(A) signal, optionally, comprising the sequence of SEQ ID NO: 9. In exemplary aspects, the poly(A) signal is an SV40 poly(A) signal, optionally, comprising the sequence of SEQ ID NO: 13 or SEQ ID NO: 24. In exemplary aspects, the poly(A) signal is an beta-globin poly(A) signal, optionally, comprising the sequence of SEQ ID NO: 34. In exemplary aspects, the recombinant expression vector system comprises a bi-allelic poly(A) trap vector, optionally, comprising the sequence of SEQ ID NO: 30. In exemplary aspects, the recombinant expression vector system comprises a trans-acting transcriptional activator binding site. In exemplary instances, the transcriptional activator is a catabolite activator protein (CAP). In exemplary aspects, the CAP binding site comprises the sequence of SEQ ID NO: 18. In exemplary aspects, the recombinant expression vector system comprises an operator. In exemplary instances, the operator is a Lac operator, and optionally comprises the sequence of SEQ ID NO: 16. Alternative and additional sequences may be a part of the recombinant expression vector system.

In exemplary aspects, the recombinant expression vector system comprises one or more enhancer sequences, which enhance or increase the likelihood of transcription of a gene. See, e.g., Pennacchio et al., Nat Rev Genet 14(4): 288-295 (2013). In exemplary aspects, the enhancer is a human enhancer or a viral enhancer. The viral enhancer may be an SV40 enhancer or cytomegalovirus (CMV) enhancer. In exemplary aspects, the CMV enhancer comprises the sequence of SEQ ID NO: 5.

The recombinant expression vector system may include one or more marker genes, e.g., selectable marker genes, which allow for selection of transformed or transfected hosts. Selectable marker genes include biocide resistance, e.g., resistance to antibiotics, heavy metals, etc., complementation in an auxotrophic host to provide prototrophy, and the like. Suitable selectable marker genes for the expression vectors include, for instance, kanamycin resistance genes, puromycin resistance genes, zeocin resistance genes, neomycin/G418 resistance genes, hygromycin resistance genes, histidinol resistance genes, tetracycline resistance genes, geneticin resistance genes, triclosan resistance genes, R-fluroorotic acid resistance genes, 5-fluorouracil resistance genes and ampicillin resistance genes. In exemplary aspects, the recombinant expression vector system comprises one or more of a neomycin resistance gene, an ampicillin resistance gene, and a puromycin resistance gene. In exemplary aspects, the recombinant expression vector system comprises a neomycin resistance gene, two ampicillin resistance genes, and a puromycin resistance gene. In exemplary instances, the recombinant expression vector system comprises a neomycin resistance gene comprising the sequence of SEQ ID NO: 12, two ampicillin resistance genes (one comprising the sequence of SEQ ID NO: 20 and another comprising the sequence of SEQ ID NO: 26), and a puromycin resistance gene comprising the sequence of SEQ ID NO: 23.

In exemplary aspects, the recombinant expression vector system comprises one or more protein tags. Such tags can facilitate purification of the expressed protein or detect expression of the protein. In exemplary aspects, protein tag is a histidine tag, a Myc tag, a glutathione S-transferase (GST) tag. In exemplary aspects, the Myc tag is encoded by a sequence comprising SEQ ID NO: 33.

In exemplary aspects, the recombinant expression vector system comprises one or more sequencing primers for verification of sequence of the recombinant expression vector system. Sequencing primers are known in the art and include but not limited to CMV sequencing primers, MSCV sequencing primers, pGEX or pBABE sequencing primers, SP6, T3, T7, LKO1.5', and M13 sequencing primers. In exemplary aspects, the sequencing primer is a M13 forward primer sequence, optionally, comprising the sequence of SEQ ID NO: 3. In exemplary aspects, the sequencing primer is a M13 reverse primer sequence, optionally, comprising the sequence of SEQ ID NO: 15.

The recombinant expression vector system in exemplary aspects comprises a native or normative promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus. In exemplary instances, the recombinant expression vector system comprises a CMV promoter and an SV40 promoter. In exemplary instances, the CMV promoter comprises the sequence of SEQ ID NO: 5. In exemplary instances, the SV40 promoter comprises the sequence of SEQ ID NO: 11 or SEQ ID NO: 22. In exemplary instances, the recombinant expression vector system comprises a CMV promoter comprising the sequence of SEQ ID NO: 5, a first SV40 promoter comprising the sequence of SEQ ID NO: 11 and a second SV40 promoter comprising the sequence of SEQ ID NO: 22. In exemplary aspects, the recombinant expression vector system comprises additional promoters, e.g., T7 promoter, Lac promoter, or Amp promoter. In exemplary aspects, the T7 promoter comprises the sequence of SEQ ID NO: 7. In exemplary aspects, the Lac promoter comprises the sequence of SEQ ID NO: 17. In exemplary aspects, the Amp promoter comprises the sequence of SEQ ID NO: 21 or SEQ ID NO: 25.

The recombinant expression vector system may be designed for either transient expression, for stable expression, or for both. In exemplary aspects, the recombinant expression vector system comprises elements necessary for integration into the host genome. Also, the recombinant expression vectors can be made for constitutive expression or for inducible expression. For example, the recombinant expression vector system may comprise one or more suicide genes and/or one or more constitutive or inducible promoters.

In exemplary aspects, the recombinant expression vector system comprises one or more modified nucleotides and/or one or more modified inter-nucleotide linkages. In exemplary aspects, the recombinant expression vector system comprises one or more modified nucleotides selected from the group consisting of: 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosyl queuosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosyl queuosine, 5'-methoxycarboxymethyluracil, 5-methoxyuracil, 2-methylthio-N6-isopentenyladenine, uracil-5-oxyacetic acid (v), wybutoxosine, pseudouracil, queuosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. In exemplary aspects, the recombinant expression vector system comprises one or more modified inter-nucleotide linkages selected from the group consisting of: phosphoroamidate linkages and phosphorothioate linkages.

In exemplary embodiments, the recombinant expression vector system comprises at least two suicide genes, one of which is specifically inactivated in cells exhibiting the desired phenotype. In exemplary embodiments, the recombinant expression vector system comprises at least two suicide genes, one of which is specifically excised, removed or deleted in cells exhibiting the desired phenotype. In exemplary embodiments, the recombinant expression vector system comprises at least two suicide genes, one of which is specifically excised, removed or deleted via action of a recombinase in cells exhibiting the desired phenotype. In exemplary aspects, at least one of the two suicide genes is activated when the cell the recombinant expression vector system behaves similarly to or the same as a tumor cell. In exemplary aspects, the expression of at least one of the two suicide genes is controlled by a promoter which is highly active in a tumor or cancer cell.

In exemplary aspects, the recombinant expression vector system of the present disclosure comprises at least one suicide gene located between two loxP sites, two HIV markers, or two FRT sites. In exemplary aspects, each loxP site comprises a sequence of SEQ ID NO: 4 or SEQ ID NO: 14. In exemplary aspects, the recombinant expression vector system comprises a nucleic acid encoding a recombinase, including, e.g., FLT, Cre, Tre. In exemplary aspects, the Cre recombinase is encoded by a sequence of SEQ ID NO: 32. In exemplary aspects, expression of the nucleic acid encoding the Cre recombinase is controlled by a promoter which is tissue-specific or hormone-responsive. In exemplary aspects, the recombinant expression vector system comprises a telomerase promoter controlling the expression of at least one suicide gene. In exemplary aspects, the telomerase promoter is a human telomerase reverse transcriptase (hTERT) promoter. In exemplary instances, the hTERT promoter comprises the sequence of SEQ ID NO: 28.

In exemplary embodiments, the recombinant expression vector system comprises at least two suicide genes, one of which is specifically inactivated in cells exhibiting the desired phenotype. In exemplary aspects, at least one of the two suicide genes is activated when the cell expressing the recombinant expression vector system behaves similarly to or the same as a tumor cell. In exemplary aspects, the recombinant expression vector system of the present disclosures comprises at least one suicide gene located between two loxP sites. In exemplary aspects, the recombinant expression vector system comprises a nucleic acid encoding Cre recombinase. In exemplary aspects, expression of the nucleic acid encoding the Cre recombinase is controlled by a promoter which is tissue-specific or hormone-responsive. In exemplary aspects, the recombinant expression vector system comprises a telomerase promoter controlling the expression of at least one suicide gene. In exemplary aspects, the telomerase promoter is a human telomerase reverse transcriptase (hTERT) promoter. In exemplary aspects, each loxP site comprises a sequence of SEQ ID NO: 4 or SEQ ID NO: 14. In exemplary aspects, the Cre recombinase is encoded by a sequence of SEQ ID NO: 32. In exemplary instances, the hTERT promoter comprises the sequence of SEQ ID NO: 28.

In exemplary aspects, the recombinant expression vector system comprises only one recombinant expression vector comprising the at least two suicide genes. Alternatively, the recombinant expression vector system comprises more than one recombinant expression vector. In exemplary aspects, the recombinant expression vector system comprises one recombinant expression vector per number of suicide genes in the system. In exemplary aspects, the recombinant expression vector system comprises two suicide genes and two recombinant expression vectors. In exemplary aspects, the recombinant expression vector system comprises two, three, four, five, or more recombinant expression vectors.

In exemplary aspects, the recombinant expression vector system comprises a first suicide gene and expression of the first suicide gene is controlled by a constitutive promoter, including but not limited to SV40, UBC, EF1A, PGK and CAGG (Qin et al, PLOS One 5(5): e10611). In exemplary aspects, the expression of the first suicide gene is controlled by a cytomegalovirus (CMV) promoter. In exemplary aspects, the first suicide gene is subject to removal, excision or deletion by means of a Cre-lox system. In exemplary aspects, the first suicide gene is located in a recombinant expression vector between two lox sites. In exemplary aspects, the recombinant expression vector system comprises a nucleic acid encoding Cre recombinase. In exemplary aspects, the promoter which controls expression of Cre is activated when the cell expressing the recombinant expression vector system has differentiated into the intended cell type. In exemplary aspects, expression of Cre is controlled by a tissue-specific promoter or hormone-responsive promoter. In exemplary aspects, the tissue-specific promoter is an islet beta cell-specific promoter. In exemplary aspects, the hormone-responsive promoter is an insulin-responsive promoter. In exemplary aspects, the insulin-responsive promoter is a rat insulin promoter or a human insulin promoter (hIP). In exemplary aspects, the hIP comprises the sequence of SEQ ID NO: 31. In exemplary aspects, the tissue specific promoter is pancreatic pan-endocrine (IS1, CGA, SYP, etc.). In exemplary aspects, the tissue-specific promoter is a liver-specific promoter, or an albumin promoter. In exemplary aspects, the promoter controlling the expression of Cre and the nucleic acid encoding Cre are located in the same recombinant expression vector as the first suicide gene and the lox sites. Alternatively, the promoter controlling the expression of Cre and the nucleic acid encoding Cre are located in a recombinant expression vector which is different from the one comprising the first suicide gene and the loxP sites. In exemplary aspects, the Cre-lox system of the recombinant expression vector system is replaced with another recombinase system. In exemplary aspects, FLT recombinase and FRT sites are used instead of Cre recombinase and loxP sites. Alternatively, in exemplary aspects, Tre recombinase and HIV markers are used in place of Cre and loxP sites.

In exemplary aspects, the recombinant expression vector system comprises a second suicide gene and the expression of the second suicide gene is activated when the cell expressing the recombinant expression vector system behaves similarly to or the same as a tumor cell or a cancer cell. In exemplary aspects, the expression of the second suicide gene is controlled by a telomerase promoter, e.g., a human telomerase promoter. In exemplary aspects, the expression of the second suicide gene is controlled by a promoter highly expressed in tumorigenic cells, e.g., BIRC5 (survivin). See, e.g., Blum et al., Nat Biotechnol 27: 281-287 (2009). In exemplary aspects, the expression of the second suicide gene is controlled by a naturally occurring or native promoter. In exemplary aspects, the expression of the second suicide gene is controlled by synthetic version of said promoter or a hybrid combination of promoters (e.g., hTERT-CMV). See, e.g., Davis et al, Cancer Gene Therapy (2006) 13, 720-723).

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews. Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine deaminase, purine nucleoside phosphorylase, and nitroreductase. In exemplary aspects, the first suicide gene or second suicide gene of the recombinant expression vector system is a heterologous enzyme that metabolizes an inactive prodrug into a cytotoxin. In exemplary aspects, the first suicide gene or second suicide gene is independently selected from the group consisting of: thymidine kinase (TK), guanine phosphoribosyl transferase, carboxypeptidase G2, purine nucleoside phosphorylase, cytosine deaminase-5-fluorocytosine, cytochrome P450-ifosfamide, cytochrome P450-cyclophosphamide, and nitroreductase-5-[aziridin-1-yl]-2,4-dinitrobenzamide. In exemplary aspects, the first suicide gene is TK and the second gene is nitroreductase-5-[aziridin-1-yl]-2,4-dinitrobenzamide, or nitroreductase. In exemplary instances, the TK gene comprises the sequence of SEQ ID NO: 29. In exemplary instances, the nitroreductase gene comprises the sequence of SEQ ID NO: 8.

In exemplary aspects, each vector of the recombinant expression vector system comprises a selectable marker. In exemplary aspects, the selectable marker is a gene product which confers resistance to an antibiotic, including but not limited to ampicillin, kanamycin, neomycin/G418, tetracycline, geneticin, triclosan, puromycin, zeocin, and hygromycin. In exemplary aspects, the selectable marker is selected from the group consisting of: kanamycin resistance genes, puromycin resistance genes, zeocin resistance genes, neomycin/G418 resistance genes, hygromycin resistance genes, histidinol resistance genes, tetracycline resistance genes, geneticin resistance genes, triclosan resistance genes, R-fluoorotic acid resistance genes, 5-fluorouracil resistance genes and ampicillin resistance genes. In exemplary aspects, when the system comprises more than one recombinant expression vector, each vector comprises a selectable marker. In exemplary aspects, each vector has the same selectable marker. Alternatively, each vector within the system comprises a different selectable marker.

In exemplary aspects, the recombinant expression vector comprises a nucleic acid encoding a tissue-specific promoter or hormone-responsive promoter; a nucleic acid encoding Cre recombinase; two loxP sites; a cytomegalovirus (CMV) promoter; a first suicide gene; a nucleic acid encoding a telomerase promoter (optionally hTERT (e.g., comprising SEQ ID NO: 28)); a second suicide gene; and a nucleic acid encoding a selectable marker. In exemplary aspects, the tissue-specific promoter or hormone-responsive promoter controls expression of Cre recombinase. In exemplary aspects, the Cre recombinase is encoded by a nucleic acid comprising the sequence of SEQ ID NO: 32. In exemplary aspects, the tissue-specific promoter is an insulin promoter and optionally comprises the sequence of SEQ ID NO: 31. In exemplary aspects, the first suicide gene is located between the two loxP sites. In exemplary instances, each loxP site comprises the sequence of SEQ ID NO: 4 or 14. In exemplary aspects, the CMV promoter controls expression of the first suicide gene. In exemplary aspects, the CMV promoter comprises the sequence of SEQ ID NO: 6. In exemplary aspects, the first suicide gene is a thymidine kinase gene. In exemplary instances, the TK gene comprises the sequence of SEQ ID NO: 29. In exemplary aspects, the telomerase promoter controls expression of the second suicide gene. In exemplary aspects, the recombinase is Cre, but other recombinases could also be used, such as FLT recombinase (FRT sites instead of loxP), Tre recombinase (using HIV markers instead of loxP) and others. In exemplary instances, the second suicide gene is a nitroreductase gene, optionally, comprising the sequence of SEQ ID NO: 8.

Figure 3:
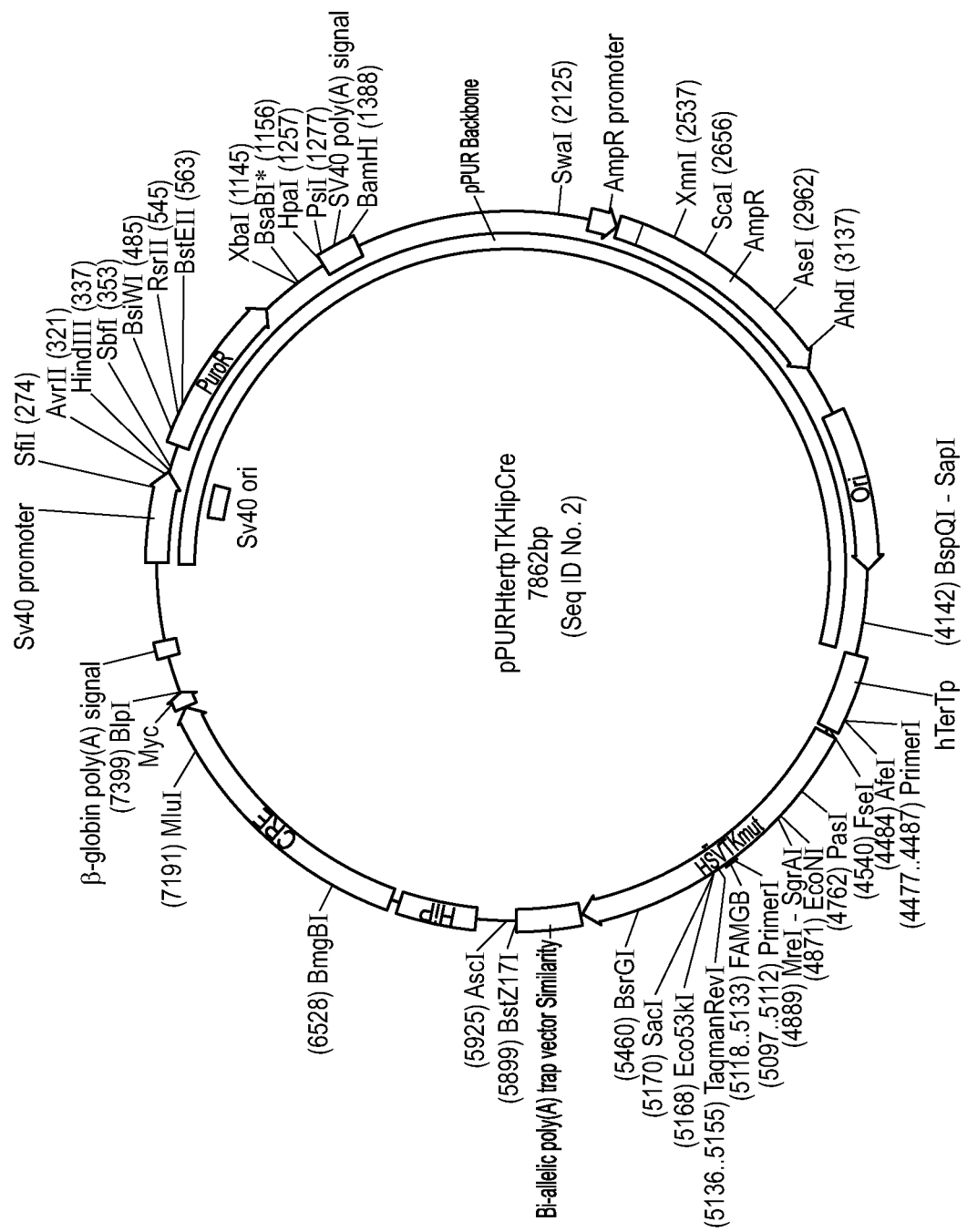
FIG. 3 is a schematic diagram of the pPURHtertpTKH-ipCre vector comprising a nucleic acid (SEQ ID NO: 2) encoding human insulin promoter (HIP)-Cre recombinase with a Myc tag, a nucleic acid encoding HSV thymidine kinase (HSVTK) under the control of a telomerase promoter (hTERTp), and a nucleic acid encoding a selectable marker which provides resistance to ampicillin (AmpR).
Figure 4:
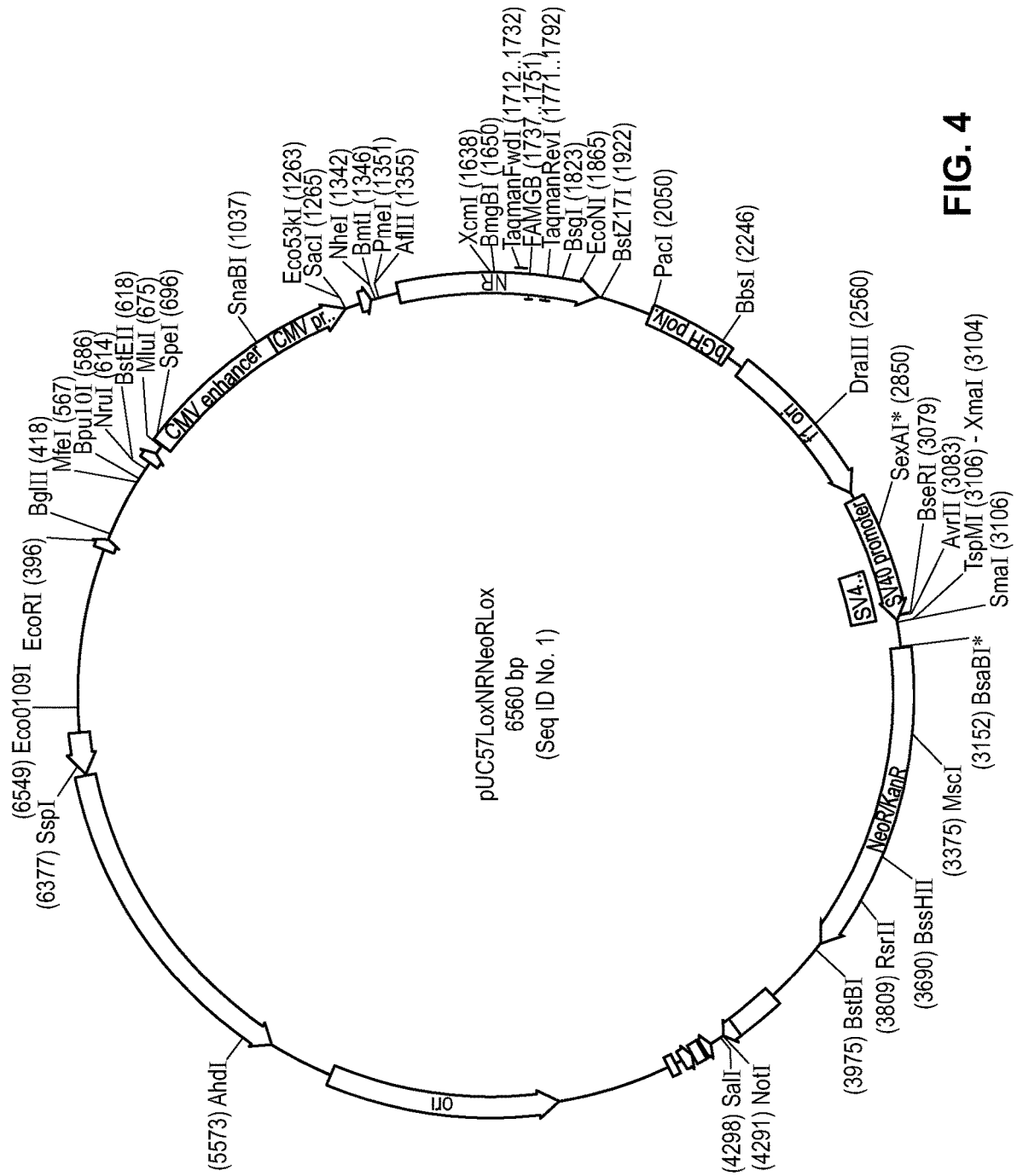
FIG. 4 is a schematic diagram of the pUC57LoxNRNeoRLox vector comprising a nucleic acid (SEQ ID NO: 1) encoding NRNeo flanked by two Lox sites and a nucleic acid encoding a selectable marker which provides resistance to neomycin and kanamycin (NeoR/KanR).
Figure 5:
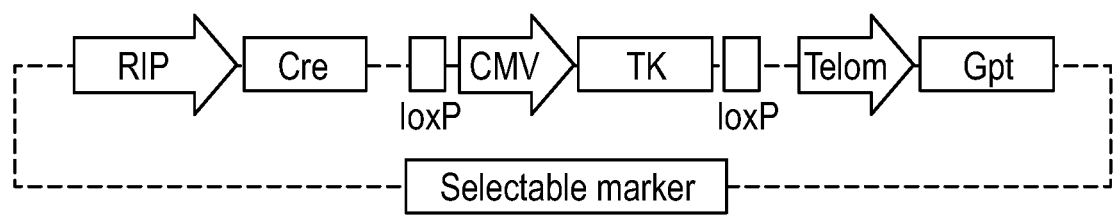
FIG. 5 is a schematic diagram of an exemplary recombinant expression vector comprising all components of the recombinant expression vector system of the present disclosure. RIP=rat insulin promoter, which is expressed in insulin-producing cells, such as islet beta cells; Cre=Cre recombinase, which excises any length of DNA comprised between two loxP sites; CMV=cytomegalovirus promoter, which ensures high constitutive levels of gene expression in mammalian cells; TK=thymidine kinase, which destroys the cell in the presence of the pro-drug ganciclovir; Telom=human telomerase promoter, which is expressed in non-terminally differentiated cells, as well as in active tumors; Gpt=guanine phosphoribosyl transferase, which destroys the cell in the presence of the pro-drug 6-TX; Selectable marker is used to select for stably transfected cell clones.
Figure 6A:
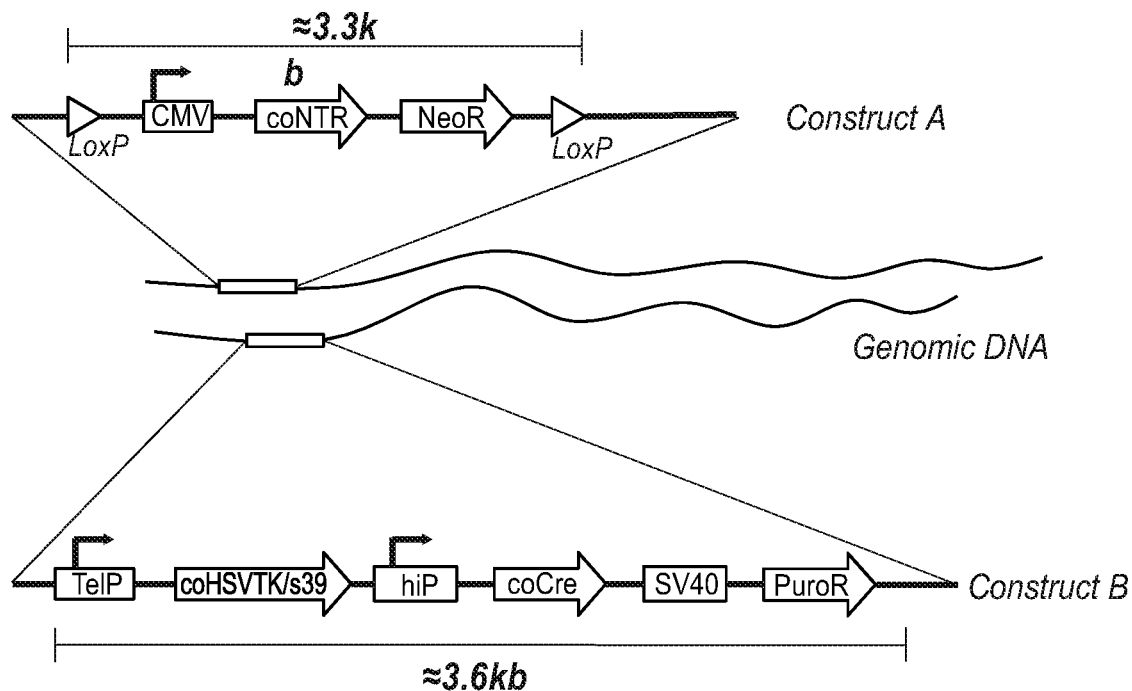
FIG. 6A depicts two vector constructs. Construct A comprises a CMV promoter and a nitroreductase gene (coNTR) followed by a neomycin resistance gene cassette. Such components are flanked by LoxP sites. Construct B comprises a telomerase promoter followed by a HSV-TK gene cassette. Construct B also comprises a human insulin promoter (hIP) followed by Cre recombinase gene cassette. Construct B further comprises an SV40 promoter followed by a puromycin resistance gene cassette.
Figure 6B:
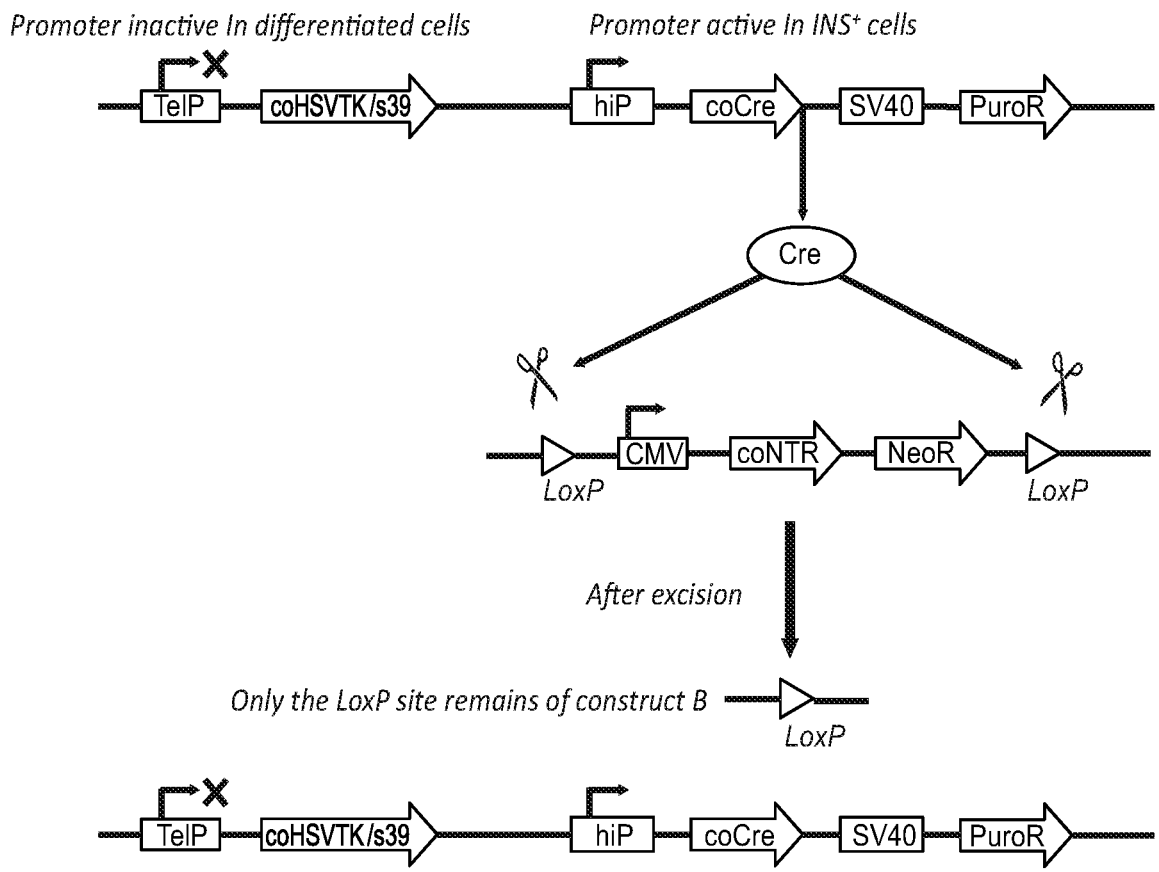
FIG. 6B depicts the mechanism of action of the constructs in cells under different conditions. hIP is active in insulin-positive cells causing the expression of Cre recombinase which acts on Construct A to cause excision of the components flanked between the LoxP sites, so that only LoxP remains in the construct.

In exemplary aspects, the recombinant expression vector system comprises the recombinant expression vectors shown in FIGS. 3 and 4. In exemplary aspects, the recombinant expression vector system comprises a recombinant expression vector comprising a sequence of SEQ ID NO: 1 (pUC57LoxNRNeoRLox) and/or SEQ ID NO: 2 (pPURH-tertpTKHipCre). The sequences of the individual components of SEQ ID NO: 1 and 2 are shown in FIG. 6. In exemplary aspects, the recombinant expression vector system comprises the recombinant expression vector shown in FIG. 5.

Host Cells

Also provided by the present disclosure is a host cell comprising any one of the recombinant expression vector systems described herein. As used herein, the term "host cell" refers to any type of cell that can contain the inventive recombinant expression vector system. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. In exemplary aspects, the host cell is a stem cell. In exemplary aspects, the host cell is a human stem cell. In exemplary aspects, the stem cell is a totipotent stem cell, a pluripotent stem cell or a multipotent stem cell. In exemplary aspects, the stem cell is an embryonic stem cell, a primordial germ cell, an adult stem cell (i.e., somatic stem cell, tissue-specific stem cell), or an induced pluripotent stem cell. In exemplary aspects, the stem cell is a mesenchymal stem cell (MSC) or a hematopoietic stem cell. In exemplary aspects, the MSC is an MSC from a pancreatic islet, a pancreatic ductal or acinar tissue, bone marrow, adipose tissue, amniotic fluid, umbilical cord or placenta. In exemplary aspects, the stem cell is a multipotent progenitor cell (MPP), a lineage-restricted progenitor cell (LRP), a common myeloid progenitor (CMP), a granulocyte-macrophage progenitor (GMP), or a megakaryocyte-erythroid progenitor (MEP). In exemplary aspects, the host cell is a human embryonic stem cells (hESc), a primordial germ cell, an induced pluripotent stem cells (iPSc), or a cell of a pluripotent cell type.

Also provided by the present disclosure is a population of cells comprising at least one host cell described herein. The population of cells can be a heterogeneous population comprising the host cell comprising any of the recombinant expression vectors described, in addition to at least one other cell. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

Kits

Kits comprising host cells or recombinant expression vector systems of the present disclosure are also provided. In exemplary embodiments, the kit comprises at least one agent which causes cell death to cells expressing a suicide gene. The kit in exemplary aspects comprises ganciclovir, if one of the suicide genes is thymidine kinase. In exemplary aspects, the kit comprises at least one agent which causes cell death to cells not expressing the selectable marker of the recombinant expression vector system. The kit in exemplary aspects comprises neomycin in the instance the system comprises a neomycin resistance gene. In exemplary aspects, the agent is selected from the group consisting of: ampicillin, hygromycin, zeocin, puromycin, kanamycin, geneticin, triclosan, R-fluoorotic acid or 5-fluorouracil.

In exemplary aspects, the kits comprise a unit dose of stem cells comprising the recombinant expression vector systems of the present disclosure. In exemplary aspects, the kit comprises a sterile, GMP-grade unit dose of the stem cells. In exemplary aspects, a unit dose of stem cells comprises $10^5$, $10^6$, $10^7$, $10^8$, $10^9$, $10^{10}$, $10^{11}$, $10^{12}$ $10^{13}$, or more than $10^{15}$ stem cells comprising the recombinant expression vector system of the present disclosure.

In exemplary aspects, the unit dose of stem cells is packaged in an intravenous bag. In exemplary aspects, the unit dose of stem cells is provided in a cryogenic form. In exemplary aspects, the unit dose of stem cells is ready to use. In exemplary aspects, the unit dose of stem cells are provided in a tube, a flask, a dish, or like container.

Methods

Further provided is a method of producing stem cells suitable for transplantation into a subject. In exemplary embodiments, the method comprising contacting a cell culture comprising stems cells with any one of the recombinant expression vector systems described herein and adding to the cell culture an agent which causes cell death to cells expressing a suicide gene or an agent which causes cell death to cells not expressing a selectable marker. In exemplary aspects, the method comprises contacting the cell culture with an agent which causes cell death to cells not expressing a selectable marker. In exemplary aspects, the agent is selected from the group consisting of neomycin, ampicillin, kanamycin, puromycin, hygromycin, zeocin, geneticin, triclosan, R-fluoroorotic acid or 5-fluorouracil.

Furthermore provided is a method of transplanting stem cells to a subject in need thereof, comprising administering to the subject stem cells comprising the recombinant expression vector system of the present disclosure and administering to the subject an agent which causes cell death to cells expressing a suicide gene.

Methods of administering stem cells to a subject are well-known. See, e.g., Karussis et al., Arch Neurol 67(10): 1187-1194 (2011); Kamani et al., *Biol Blood Marrow Transplant* 18(8) 1265-1272 (2012); Tedesco et al., Sci Transl Med 4: 149ra89 (2012); Bartlett, S. T., et al. Report from IPITA-TTS Opinion Leaders Meeting on the Future of beta-Cell Replacement. *Transplantation* 100 Suppl 2, S1-44 (2016); Schulz, T. C., et al. A scalable system for production of functional pancreatic progenitors from human embryonic stem cells. *PLoS One* 7, e37004 (2012); Dominguez-Bendala, J., et al. The Human Endocrine Pancreas: New Insights on Replacement and Regeneration. *Trends Endocrinol Metab* (2016); Kroon, E., et al. Pancreatic endoderm derived from human embryonic stem cells generates glucose-responsive insulin-secreting cells in vivo. *Nat Biotechnol* 26, 443-452 (2008); Stem Cells. 2013 October; 31(10):2047-60. doi: 10.1002/stem.1457; Concise review: clinical programs of stem cell therapies for liver and pancreas; Lanzoni G1, Oikawa T, Wang Y, Cui C B, Carpino G, Cardinale V, Gerber D, Gabriel M, Dominguez-Bendala J, Furth M E, Gaudio E, Alvaro D, Inverardi L, Reid L M.

Without being bound to a particular theory, the administration, e.g., transplantation, of such stem cells with the recombinant expression vector of the present disclosure provides cells which differentiate into cells having therapeutic value. Thus, the administration, e.g., transplantation, of such stem cells with the recombinant expression vector of the present disclosure provides therapeutic treatment of the subject. Accordingly, the present disclosure provides methods of treating a disease in a subject in need thereof, comprising administering, e.g., transplanting, stem cells with the recombinant expression vector of the present disclosure in an amount effective to treat the disease. In exemplary aspects, the disease is a metabolic disease (e.g., diabetes), a liver disease, a neurodegenerative disease, an autoimmune disease, a cardiac disease, a genetic blood disease, cancer and the like.

The following examples are given merely to illustrate the present invention and not in any way to limit its scope.

EXAMPLES

Example 1

This example demonstrates the construction of an exemplary vector system of the present disclosure.

The suicide gene cassettes shown in FIG. 1 were synthesized base pair by base pair by GenScript (Piscataway, N.J.) according to our design specifications. The vector was designed to contain Kozak sequences[33], terminator sequences and enhancers as required for each unit of expression. Human codon usage optimization was also applied, as some of the mutant sequences used (such as NR T41L/N71S, which has 100×higher $K_{cat}$/Km than the wild-type enzyme) contained codons that are infrequent in humans. Due to the size of the construct encompassing both suicide cassettes, for proof-of-principle purposes, it was decided to split the single vector into two separate plasmids that could be independently transfected: These were plasmid L (containing TeIP-TK-hiP-Cre) and F (LoxP-CMV-NR).

The main elements of plasmid F are Lox P sites and Nitroreductase (NTR, T41L/N71 S mutant). LoxP are 34 bp recombination sites from the bacteriophage P1 containing an asymmetric 8 bp flanked by two sets of palindromic 13 bp sequences. The Cre recombinase induces loxP-specific recombination. As a result of Cre activity, sequences flanked by loxP sites are excised out, leaving a single loxP site in place.

NTR is a flavoenzyme homodimer of 24 kDa subunits with tightly bound flavin mononucleotide (FMN) cofactors, encoded by the *E. coli* nsfB/nfnB gene. A variety of substrates, including CB1954 [5-(aziridin-1-yl)-2,4-dinitrobenzamide] bind to the enzyme and get reduced by the FMN to a 4-hydroxylamino derivative, which in the presence of acetyl coenzyme A becomes a highly cytotoxic DNA interstrand cross-linking agent[31,43]. Since virus-mediated expression of NTR in tumor cells sensitizes them to CB1954 in vitro and in vivo, this "suicide gene" strategy has been tested in human clinical trials for several types of cancer[35]. Site-directed mutagenesis has been used to identify several mutants with enhanced kinetics of CB1954 activation, which may improve cell sensitization to the pro-drug. Our construct contains the sequence of the double mutant T41L/N71S, kindly given by Professor P. F. Searle (University of Birmingham, UK). T41L/N71S is a much faster enzyme at low CB1954 concentrations in vitro (100×higher $K_{cat}$/Km than the wild-type NfsB). In tumor cell lines, it sensitizes cells to CB1954 concentrations up to ~15-fold lower than the native enzyme (Prof. Searle, personal communication). Also, T41L/N71S preferentially reduces the 4-$NO_2$ group of CB1954, which is more cytotoxic than 2-$NO_2$-reduction products. This makes the double mutant a superior enzyme for our purposes. In our construct, the T41L/N71S NTR gene is constitutively driven by the CMV promoter. This plasmid is selectable in Neomycin/G418. The neomycin resistance cassette is constitutively driven by the SV40 promoter. Upon Cre expression, both the NR and Neomycin resistance cassettes (which are in a region of the construct flanked by loxP sites) are eliminated.

The main elements of plasmid L are HSV thymidine kinase (HSV-TKSR39 mutant) and Cre. The thymidine kinase of the herpes simplex virus (HSV) helps viral DNA synthesis by adding a phosphate group to thymidine. The resulting dTMP is further phosphorylated to deoxythymidine di- and tri-phosphate, which is added to new viral DNA chains. However, HSV-TK can also phosphorylate nucleoside analogs such as aciclovir (ACV) and ganciclovir (GCV). Phosphorylation of GCV inside cells harboring the HSV-TK gene result in the accumulation of toxic metabolites, which eventually results in cell death[44]. As with NTR, this system has also been safely tested in clinical trials for the treatment of cancer[45,46]. Our construct features an enhanced mutant, HSV-TKSR39[47-49] (sequence kindly given by Dr. Qasim, UCL, UK), which has a higher activity at lower doses of the pro-drug[50]. The HSV TK gene has been placed under the control of the human telomerase reverse transcriptase (hTERT) promoter, which drives the expression of hTERT in immortal cells[51]. Most somatic cells express it at very low levels or not at all, whereas hESc and most tumoral cells exhibit high levels of hTERT expression. As naturally occurring immature teratomas have high telomerase activity[40], it is expected that the placement of HSV-TK under the control of the telomerase promoter will lead to the selective expression of the suicide gene in carry-over undifferentiated hESc.

Cre is a site-specific recombinase from the bacteriophage P1 (see loxP above). In our construct design, expression of Cre will excise out the sequence comprised between the two loxP sites (NTR cassette). Since Cre is driven by the human insulin promoter (region −362 to +1 bp, which contains its key activation domains[52]), these elements will be eliminated only in cells that express insulin upon differentiation, rendering them insensitive to CB1954.

Plasmid L is selectable in puromycin, and the resistance gene is driven by the SV40 promoter. Backbone sequences for both Plasmid R and L feature all the necessary elements for replication and expansion in bacterial hosts (including the ampicillin resistance marker). Throughout the entirety of this construct, we have been careful to add Kozak sequences[53] wherever needed to ensure maximal expression in human cells. Terminator sequences and enhancers are also placed as required for each unit of expression. We have also applied human codon usage optimization during the synthesis of Tel-TK(NR)hiP-Cre. This precaution is especially important because some of the mutant sequences used (such as NR T41L/N71S) contain codons that are used rather infrequently in highly expressed human genes (P. F. Searle, personal communication).

Example 2

This example demonstrates generation of a human embryonic stem cell line and in vitro testing thereof.

Figure 2:
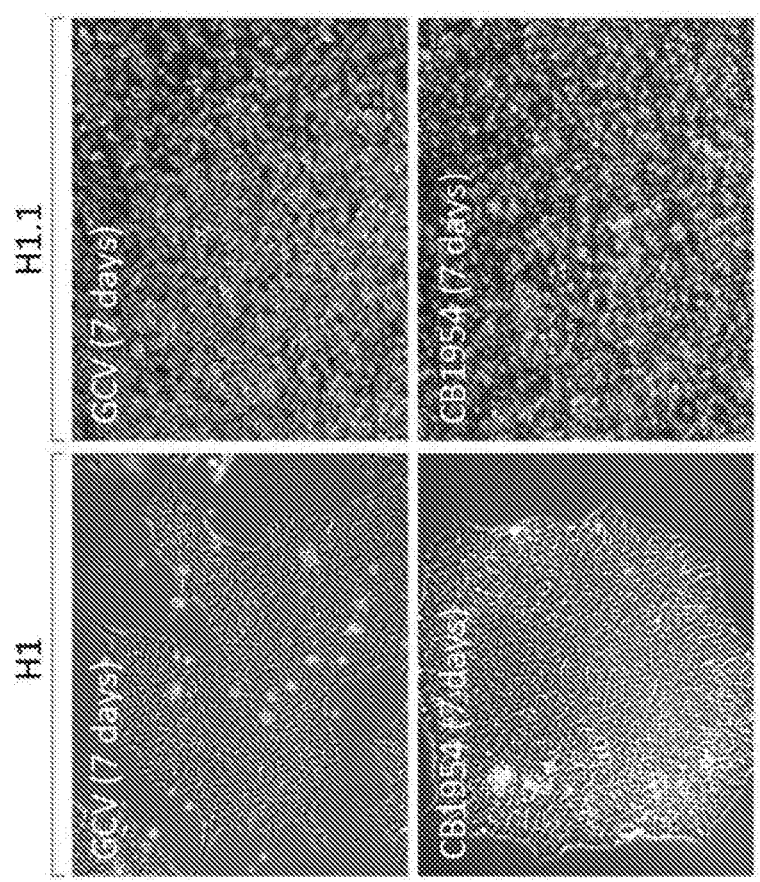
FIG. 2 is a set of images demonstrating H1 parental hESc cultures are resistant to GCV and CB1954 after 7 days of exposure (left column). In contrast, H1.1 cells, which contain two suicide constructs that render them sensitive to both pro-drugs, are 100% ablated after 7 days of exposure.

Clones of the hESc line H1 containing both constructs were selected using Puro (for plasmid L) and Neo (for plasmid F). We used electroporation of the linearized plasmids followed by Puro+Neo selection to achieve stable integration of both cassettes (λH1). Integration was confirmed by PCR, and positive clones were expanded and stocked in liquid $N_2$. ~25 double resistant clones were handpicked, expanded under antibiotic selection and frozen in liquid $N_2$. A typical undifferentiated colony of one such clone, propagated in Puro+Neo to maintain selective pressure, was imaged. In their undifferentiated state, such clones have been shown to be sensitive to both CB1954 and GCV. Aliquots were screened by genomic PCR to confirm the integration of both constructs (data not shown). qRT-PCR was performed to determine which clones had higher transgene (HSV-TK and NTR) expression. Clone A (H1.1 from now on) was selected for further testing based on the results of these assays. A kill curve using different dosages for GCV (0.01 to 1000 μM) and CB1954 (0.1 to 300 μM) was done for H1.1. Cell death was quantified by MTT assays on H1.1 and the parental wild-type H1 line. These assays helped us determine the optimal concentration of each pro-drug that leads to complete ablation of undifferentiated H1.1 cells while preserving the viability of the parental line within 7 days. Such concentration was in the range of 10-100 μM for GCV and 50-100 μM for CB1954, as previously reported in the literature for other cell types[26,54,55]. The integration of these constructs had no detectable effects in terms of pluripotency marker expression (TRA-1-60, SSEA3, SSEA4, Oct3/4, Nanog) vs. the unmodified parental line H1, as determined by qRT-PCR, immunofluorescence and FACS analyses (data not shown). FIG. 2 (right column) shows H1.1 cells after 7 days of GCV (top row) or CB1954 (bottom row) selection. Unmodified parental clones (left column) remain largely unscathed by these treatments at the same time point.

Example 3

This example demonstrates additional studies relating to the vectors of the present disclosure.

The aim of the first study will be to assess the ability of our suicide switches, e.g., Tel-TK(NR)hIP-CRE, to control non-specific differentiation and tumorigenic proliferation. Stable suicide gene-equipped clones in additional hESc line (Wicell's H9) and two iPSc lines (DF19-9-11T.H and DF4-3-7T.A, also from WiCell) are generated in order to demonstrate the repeatability of our strategy. The modified lines are karyotyped and it is confirmed that undifferentiated clones are GCV- and CB1954-sensitive. Next, their differentiation into pancreatic endocrine cells is induced. While the most recent state-of-the art protocols[5] are followed in this study, earlier versions that yield a mix of insulin+ cells, other differentiated cell types and cells that form teratomas when implanted in rodents[4] also are deliberately followed. The differentiated cells in vitro with both pro-drugs are challenged. The expected outcome is the ablation of all insulin− and telomerase+ cells by CB1954 and GCV, respectively. This outcome is quantified against unchallenged controls. Differentiated cell products, prior to and after selection, are submitted to the Beta-Cell Function Analysis Lab at the U. of Illinois in Chicago for beta-cell phenotype verification.

The aim of the second study is to design and test similar constructs based on pan-endocrine promoter selectivity (Isl1, synaptophysin). While the aim of the first study is designed to establish proof of principle, the presence of other non-beta endocrine cell types in the graft is widely perceived as important for the fine-tuning of glucose metabolism. By replacing the insulin promoter by pan-endocrine ones such as synaptophysi, Isl1 or chromogranin, the approach described herein will allow for the selective survival of endocrine cell types.

The aim of the third study is to integrate the above constructs into the ROSA26 locus of selected hPSC lines by CRISPR/Cas9 gene editing techniques. Once function has been proven, our next endpoint is to target these constructs into a known location of the human genome: (a) whose targeting does not result in harmful insertional mutagenesis (especially of tumor-suppressor genes); (b) that supports adequate transgene expression; and (c) that can be targeted with relative ease. ROSA26 is a locus that satisfies all the above criteria, and as such has been extensively used for targeted transgene integration in mice[44] and hESc[45]. hROSA26 has a sequence similarity of >85% with its mouse counterpart. It maps to a non-coding region of the DNA (THUMPD3-AS1), of which three variants have been described, transcribing long non-coding RNAs. However, since there have been two updates in the human genome database since the hROSA26 region was first published[45], there is a need to re-define what would be a safe harbor region for ectopic integration. Remarkably, within the 1220 bp region first identified, now lie the exons for the THUMPD3-AS1 gene in the negative sense strand and the first exon of the SETD5 gene in the positive strand. We posit that the region between these two exons is safe for integration of external sequences. Thus, we propose to target the region at chr3:9,397,494-9,397,698 (GRCh38.p7 2013 library). gRNAs will be designed to target this stretch of 205 bp, which does not contain any gene or known regulatory site.

Experimental plan: (a) tRNA design. Using the CRISPR tool developed by Dr. F. Zhang and available at the crispr.mit.edu website, we designed gRNAs to target the above region. Out of 57 gRNAs analyzed, we chose 3 with the best score (92, 94 and 95) and least predicted off-target cutting. The plasmid used for Cas9 expression is pX330-U6-ChimericBBCBhh-SpCas9 (Addgene). It contains an easy-to-incorporate sgRNA site flanked by BbsI restriction sites. We will also add an eGFP cassette for sorting of Cas9+ cells. Our lab uses a modified protocol that allows for colony formation from single cells without differentiation. (b) Donor plasmid design. A donor plasmid will be designed for a region flanking the 3 proposed cut sites. It is recommended (Dr. Zhang, personal communication) that the homology directed repair (HDR) flanking arms should be homologous to a site ≤100 bp away from the target. Our HDR arms will have homology to the flanking regions 800 bp to each side of the cut site of our 1$^{st}$ gRNA. We have designed a pUC19-hROSA26-HDR plasmid consisting of a 1.6 kb HDR region, with 10 restriction sites in the middle. This will allow for subcloning of L and F sequences in independent donor plasmids. hESc electroporation with the Cas9 plasmid will allow for eGFP sorting, followed by transfection with donor plasmids for hROSA26-directed knock-in (methods further described in[46]). Knock-in verification. We have designed surveyor primers specific to our HDRs. PCR amplification of genomic DNA showing amplicons of the predicted size will confirm specific knock-ins within hROSA26. Since Plasmid L and F sequences are in independent donor plasmids, we will screen for their insertion into each of the two alleles of the locus.

The aim of the fourth study is to perform in vivo tests of function in rodents. The ultimate goal is to confirm the approach in vivo, and, in particular, to characterize the method with respect to already formed tumors. To that end, the following groups of hPSC and/or derivatives are transplanted under the kidney capsule of immunodeficient (SCID/beige) mice: (1) Targeted undifferentiated cells (to perform straight teratoma formation assays and test their elimination by oral pro-drug administration 1-2 months after transplantation); (2) Targeted cells after in vitro differentiation and pro-drug selection; (3) Targeted cells after in vitro differentiation without pro-drug selection (after 1 month, one sub-group will receive both pro-drugs and a second sub-group will not receive any).

Example 4

This example demonstrates an exemplary recombinant expression vector system of the present disclosure.

The directed differentiation of human embryonic stem (huES) cells into islet cell types offers great promise, especially in view of the clinical success of islet transplantation for type I diabetes (1). However, transplantation of ES cell-derived tissues often results in the generation of tumors (teratomas) in animal models. Such concern would make this technology unusable for human therapy. It is desirable to devise alternative approaches for the selective ablation of those grafted cells that retain unlimited proliferation potential, while preserving the postmitotic ones. An even more specific level of selection would allow for the ablation, pre- or post-transplantation, of every cell not specific of the tissue of interest (e.g., insulin-positive cells).

A new construct has been designed to this effect. FIG. 5 is a schematic diagram of an exemplary construct. Stable transfection of such construct into any type of embryonic stem cell is expected to result in the molecular implementation of controls to avoid (a) non-specific differentiation and (b) uncontrolled proliferation.

Such cell line is used to derive insulin-producing cells by means of existing protocols. Successful differentiation results in the activation of the insulin promoter (RIP) and subsequent expression of the Cre recombinase. The 'floxed' CMV-TK cassette is excised in those cells that express insulin, but not in other cell by-products. Hence, ganciclovir selection could be applied prior to transplantation to get rid of undesired, non-specific tissues (TK+).

Insulin expression is usually associated to a state of terminal differentiation. Although beta cells do replicate in adult life (2), there is no evidence that such replication is accompanied by a re-activation of the telomerase gene. Therefore, ganciclovir selection (3) should result in the ablation of any undifferentiated escapee. However, from a safety standpoint, there are two hypothetical possibilities that cannot be ruled out: (a) The generation of semi-differentiated intermediates which, despite producing insulin (and therefore becoming ganciclovir-insensitive), are still locked in a proliferative mode; and (b) Spontaneous reversion of insulin-producing cells (already TK−) to a more undifferentiated, cycling stage.

Based on safety grounds, such theoretical concerns would still preclude the clinical transplantation of huES cell-derived insulin-producing cells. For this reason, we have included a secondary protective measure (telomerase-gpt) in the design of the construct. Telomerase expression is a common denominator of active tumors, including immature teratomas generated from undifferentiated stem cells (4). Grafted cells with teratogenic potential (telomerase-positive) that have escaped ganciclovir pre-selection could still be ablated in vivo by oral administration of 6-TX (5).

By changing the tissue-specific promoter used in this particular application (RIP), this vector can be customized to generate cell lines designed for any specific lineage of interest. For instance, using a liver-specific promoter (e.g., albumin), any cell not terminally differentiated into a hepatocyte could be ablated in vitro or in vivo. Similarly, any teratogenic escapee could be ablated in vivo upon transplantation.

Example 5

This example demonstrates a double fail-safe approach to prevent tumorigenesis and select pancreatic β-cells from human embryonic stem cells.

Pancreatic islet transplantation is an effective cell therapy for type 1 diabetes (T1D), but its clinical application is limited by the shortage of donor pancreata. Among the potential alternatives, the differentiation of human embryonic stem cells (hESc) into insulin-producing β-cells has taken an early lead. However, while the proportion of β-cells obtained through current methods is relatively high, a significant percentage of undefined non-endocrine cell types are still generated. Most importantly, there is the potential for carry-over of non-differentiated cell types that may produce teratomas upon transplantation. In order to address these issues, we sought to modify hESc so that their differentiated progeny could be selectively devoid of tumorigenic cells and enriched for cells of the desired phenotype (in this case, pancreatic β-cells). Here we report the generation of a modified H1 hESc line (λH1) harboring two stably integrated suicide gene cassettes, whose expression results in cell death in the presence of specific pro-drugs. The first one (HSV thymidine kinase, HSV-TK) is only active in telomerase-expressing cells, whereas the second (nitroreductase, NTR) is selectively excised out of the genome in insulin-expressing cells. The pro-drugs ganciclovir (GCV) and CB1954 kill cells that express HSV-TK or NTR, respectively. We show the efficacy of this system at enriching for β-cells and eliminating tumorigenic ones both in vitro and in vivo. Our approach is innovative inasmuch as it allows for the preservation of the desired cells while eliminating those with the potential to develop teratomas. hESc derivatives with these safeguard mechanisms would be deemed safe for transplantation in humans.

Introduction

Progress on the directed differentiation of human embryonic stem cells (hESc) has finally led to their clinical implementation: the website at clinicaltrials.gov lists multiple clinical trials in which hESc are used for conditions ranging from macular degeneration to type 1 diabetes. For the latter, Phase I/II studies have already been initiated based on promising preclinical data showing diabetes reversal after transplantation of hESc-derived pancreatic progenitor cells that further mature in vivo into insulin-producing β-cells(1). Functional β-like cells differentiated from hESc using the latest protocols are already lining up in the clinical pipeline (2, 3). However, for all its clinical promise, this approach is not without limitations. While the proportion of β-like cells obtained through state-of-the-art terminal differentiation methods is relatively high (30-40%) (2, 3) a significant percentage of undefined non-endocrine cell types are also generated (2, 4). Most importantly, there is the potential for carry-over of non-differentiated cell types that may produce teratomas upon transplantation (5). Although refinements of the prevailing differentiation protocols have significantly reduced this risk in preclinical studies, the foreseeable implementation of hESc-based therapies in thousands of patients calls for caution. One single case of hESc-derived tumors in patients may set the entire field back for years. To address this concern, we set out to engineer a hESc line with control mechanisms allowing for the selective ablation of both tumorigenic cells and cells differentiated along non-desired fates. We hypothesized that constructs of our invention, when stably integrated within the host cell line genome, would impart such selectivity. Given its clinical immediacy, we decided to focus on a model of differentiation for the treatment of diabetes (insulin-producing cells), even though our system could be customized for any cell type of choice. In such model, the control mechanisms are based, respectively, on (a) the activation of a suicide gene (herpes simplex virus thymidine kinase, or HSV-TK) in cells that resume/continue tumorigenic proliferation; and (b) the irreversible inactivation of a second suicide gene (nitroreductase, NTR) in cells that express insulin. These genes impart sensitivity to ganciclovir (GCV) (6) and CB1954(7), respectively, which have been safely tested in numerous clinical trials (8)'. In our construct design, the NTR cassette, flanked by loxP sites, is excised upon expression of Cre by the human insulin promoter (9). Therefore, cells that express insulin are rendered insensitive to CB1954. The HSV-TK gene is placed under the control of the telomerase promoter, which is active only in undifferentiated cell types(10). This makes proliferating cells sensitive to GCV. Thus, our method provides a double fail-safe control such that (1) only insulin+, non-proliferating cells survive selection in vitro; (2) cells that may de-differentiate after transplantation (11) (and in which NTR was lost with the onset of insulin expression) can be still be selectively killed in vivo by GCV, leaving the rest of the graft intact; and (3) undifferentiated cells are sensitive to two pro-drugs, making it less likely for tumorigenic cells to survive in case one single drug was insufficient to destroy 100% of them. No other method reported thus far offers the same degree of safety and specificity, as conventional suicide gene-based strategies bring about the destruction of the entire graft. Our results offer proof of principle of this novel approach and open the door to the subsequent targeting of these constructs to specific "safe harbor" locations within the genome of clinical-grade hESc.

Results

Suicide Cassette Composition

Suicide gene cassettes were synthesized base pair by base pair by GenScript (Piscataway, N.J.) according to our specifications. Owing to the size of the construct encompassing both suicide cassettes, we decided to split it into two constructs that could be independently transfected. FIG. 6 shows the composition of constructs A (containing LoxP-CMV-NTR-LoxP) and B (containing hTERTP-HSV-TK-hiP-Cre), as well as their predicted function. The main elements of construct A are: (a) LoxP sites. LoxP are 34 bp recombination sites from the bacteriophage P1 containing an asymmetric 8 bp flanked by two sets of palindromic 13 bp sequences. The Cre recombinase induces loxP-specific recombination. As a result of Cre activity, sequences flanked by loxP sites are excised out, leaving a single loxP site in place (12). (b) Nitroreductase (NTR, T41L/N71 S mutant). NTR is a flavoenzyme homodimer of 24 kDa subunits with tightly bound flavin mononucleotide (FMN) cofactors, encoded by the *E. coli* nsfB/nfnB gene (13). A variety of substrates, including CB1954 [5-(aziridin-1-yl)-2,4-dinitrobenzamide] bind to the enzyme and get reduced by the FMN to a 4-hydroxylamino derivative, which in the presence of acetyl coenzyme A becomes a highly cytotoxic DNA inter-strand cross-linking agent (7). Since virus-mediated expression of NTR in tumor cells sensitizes them to CB1954 in vitro and in vivo, this "suicide gene" strategy has been tested in human clinical trials for several types of cancer (8, 13). Site-directed mutagenesis has been used to identify several mutants with enhanced kinetics of CB1954 activation, which may improve cell sensitization to the pro-drug. Our construct contains the sequence of the double mutant T41L/N71 S, kindly given by Professor P. F. Searle (University of Birmingham, UK). T41L/N71 S is a much faster enzyme at low CB1954 concentrations in vitro (100×higher $K_{cat}$/Km than the wild-type nfsB). In tumor cell lines, it sensitizes cells to CB1954 concentrations up to ~15-fold lower than the native enzyme (Prof. Searle, personal communication). Also, T41L/N71 S preferentially reduces the 4-$NO_2$ group of CB1954, which is more cytotoxic than 2-$NO_2$-reduction products. In our construct, the T41L/N71 S NTR gene is constitutively driven by the CMV promoter. This plasmid is selectable in Neomycin/G418. The neomycin resistance cassette is constitutively driven by the SV40 promoter. Upon Cre expression, both the NTR and Neomycin resistance cassettes (which are in a region of the construct flanked by loxP sites) are eliminated (FIG. 6).

The main elements of construct B are: (a) HSV thymidine kinase (HSV-TKSR39 mutant). The thymidine kinase of the herpes simplex virus (HSV) helps viral DNA synthesis by adding a phosphate group to thymidine. The resulting dTMP is further phosphorylated to deoxythymidine di- and triphosphate, which is added to new viral DNA chains. However, HSV-TK can also phosphorylate nucleoside analogs such as aciclovir (ACV) and ganciclovir (GCV). Phosphorylation of GCV inside cells harboring the HSV-TK gene result in the accumulation of toxic metabolites, which results in cell death (14). As with NTR, this system has also been safely tested in clinical trials for the treatment of cancer (15, 16). Our construct features an enhanced mutant, HSV-TKSR39(17) (sequence kindly given by Dr. Qasim, UCL, UK), which has a higher activity at lower doses of the pro-drug (18). This gene has been placed under the control of the human telomerase reverse transcriptase (hTERT) promoter, which drives the expression of hTERT in immortal cells. Most somatic cells express it at very low levels or not at all, whereas hESc and most tumoral cells exhibit high levels of hTERT expression. As naturally occurring immature teratomas have high telomerase activity (10), it is expected that the placement of HSV-TK under the control of the telomerase promoter will lead to the selective expression of the suicide gene in carry-over undifferentiated hESc. (b) Cre is a site-specific recombinase from the bacteriophage P1 (see loxP above) (12). In our construct design, Cre will excise out the sequence comprised between the two loxP sites (NTR cassette). Since Cre is driven by the human insulin promoter (region −362 to +1 bp, which contains its key activation domains (19)), these elements will be eliminated only in cells that express insulin upon differentiation, rendering them insensitive to CB1954 (FIG. 6).

Construct A is selectable in puromycin, and the resistance gene is driven by the SV40 promoter. Backbone sequences for both constructs A and B feature all the necessary elements for replication and expansion in bacterial hosts (including the ampicillin resistance marker). Throughout the entirety of this construct, we were careful to add Kozak sequences (20) wherever needed to ensure maximal expression in human cells. Terminator sequences and enhancers are also placed as required for each unit of expression. We also applied human codon usage optimization during the synthesis of each construct. This precaution is especially important because some of the mutant sequences used contain codons that are used rather infrequently in highly expressed human genes (P. F. Searle, personal communication). The sequence of both constructs are provided in the sequence listing.

Modified hESc Express the Transgenes and Maintain Pluripotency

Figure 7C:
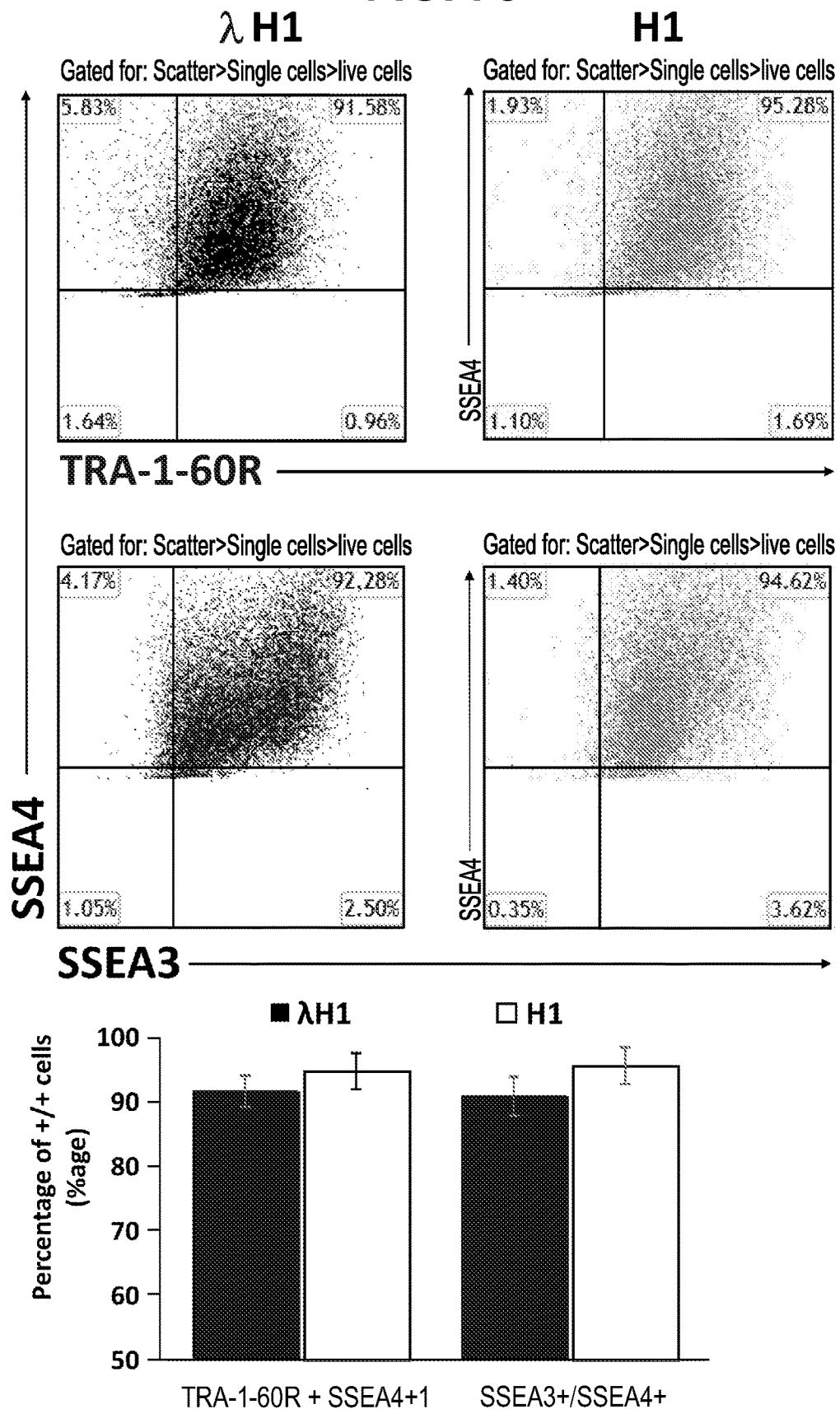
FIG. 7C is a set of flow cytometry scatter plots and graphs depicting the pattern of expression of pluripotency markers.
Figure 7D:
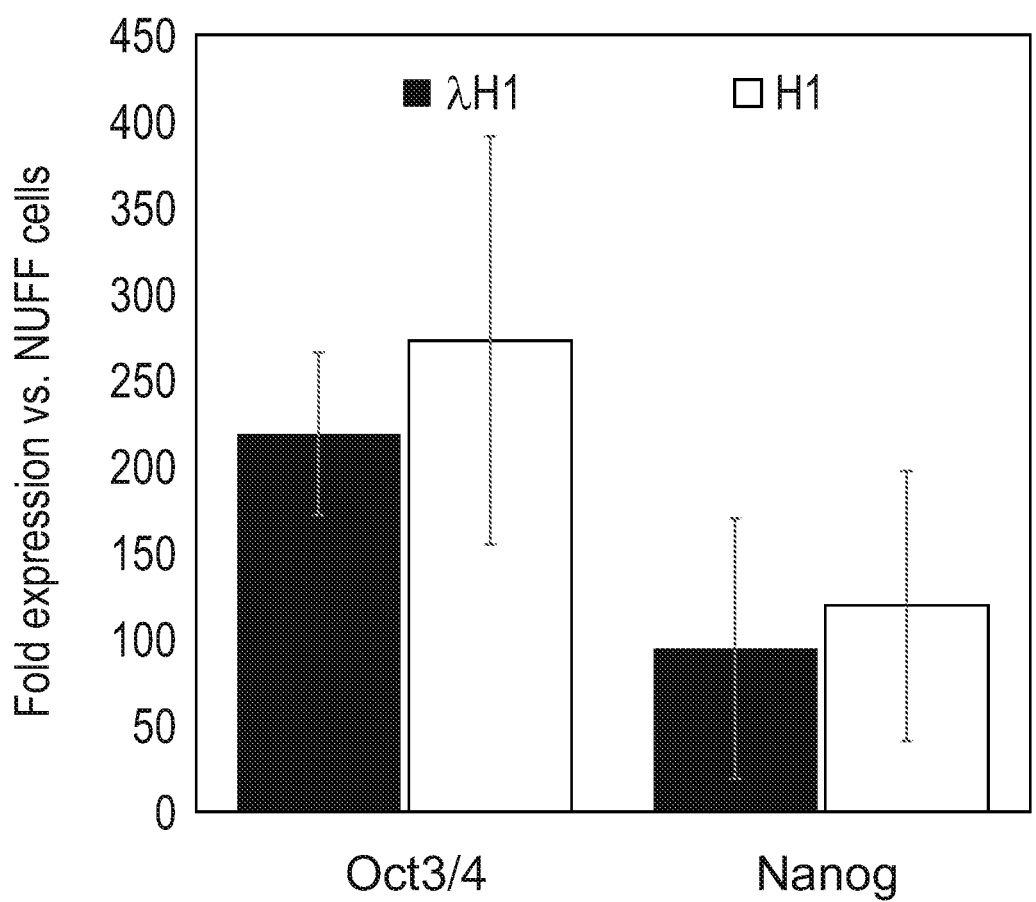
FIG. 7D is a graph depicting the fold expression (vs. NUFF cells) of Oct3/4 or Nanog in λH1 cells or H1 cells, as determined qRT-PCR.
Figure 7E:
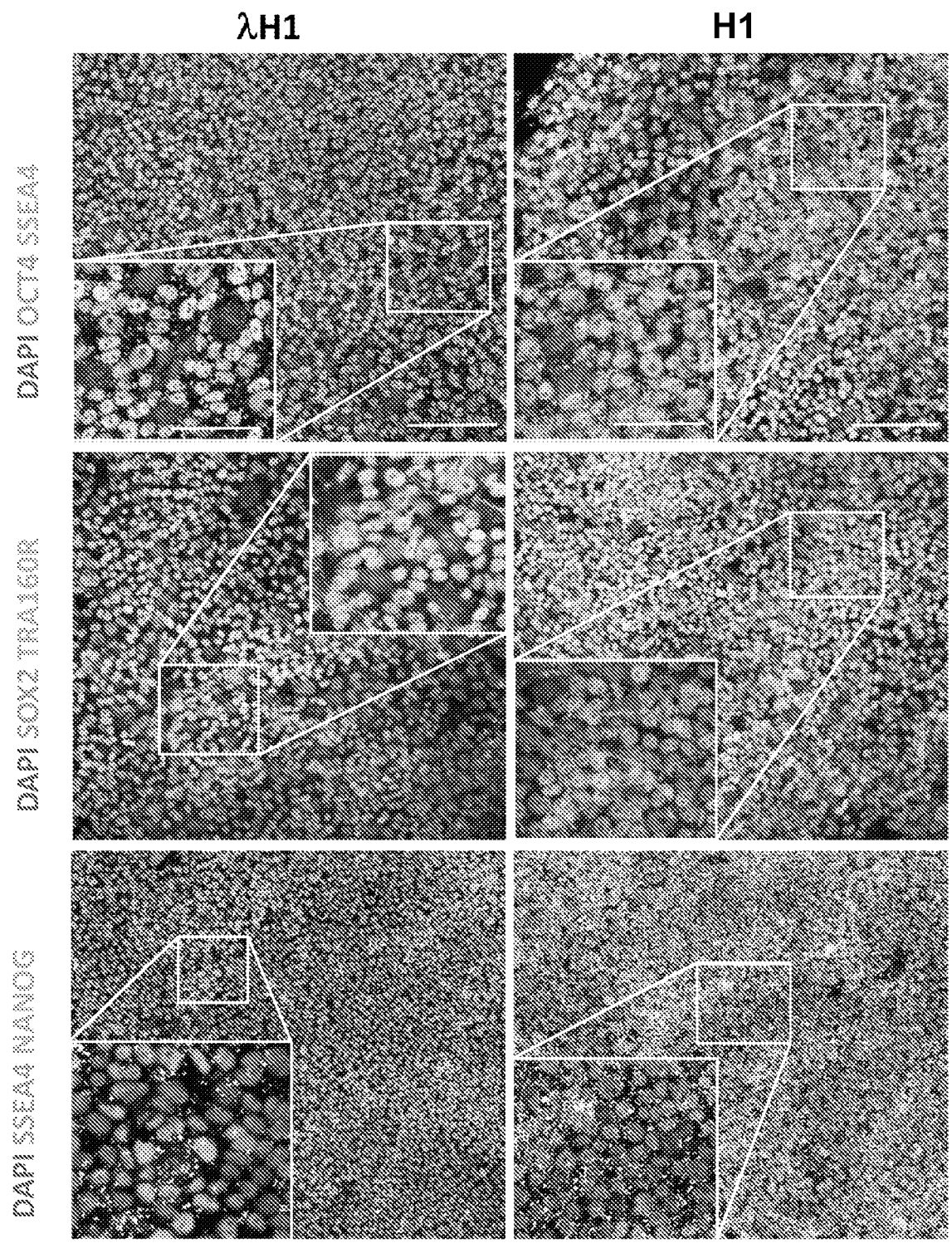
FIG. 7E is a set of immunofluorescent images depicting that the expression of indicated markers by λH1 cells were largely indistinguishable from those observed in the parental (unmodified) H1 cell line.

Clones of the hESc line H1 containing both constructs could be selected using puromycin (for A) and neomycin (for B). We used electroporation of the linearized plasmids followed by puromycin+neomycin selection to achieve stable integration of both cassettes. This cell line was therefore equipped with both suicide cassettes [hTERT-HSV-TK and (CMV-NTR)hIP-Cre]. Twenty six double resistant clones were handpicked, expanded under antibiotic selection and frozen in liquid $N_2$. Aliquots were screened by genomic PCR to confirm single-copy integration of both constructs. qRT-PCR was performed to determine which clones had higher transgene (HSV-TK and NTR) expression. Clone A (λH1 from now on) was selected for further testing based on the results of these assays. As shown in FIG. 7a, ΔH1 cells express both the NTR and HSV-TK transgenes. Both the morphology of λH1 colonies (FIG. 7b) and their pattern of expression of pluripotency markers [as determined by flow cytometry (FIGS. 7c, d), qRT-PCR (FIG. 7e) and immunofluorescence (FIG. 7f)] were largely indistinguishable from those observed in the parental (unmodified) H1 cell line.

λH1 Cells are Sensitive to Both Ganciclovir and C81954 In Vitro

Figure 8A:
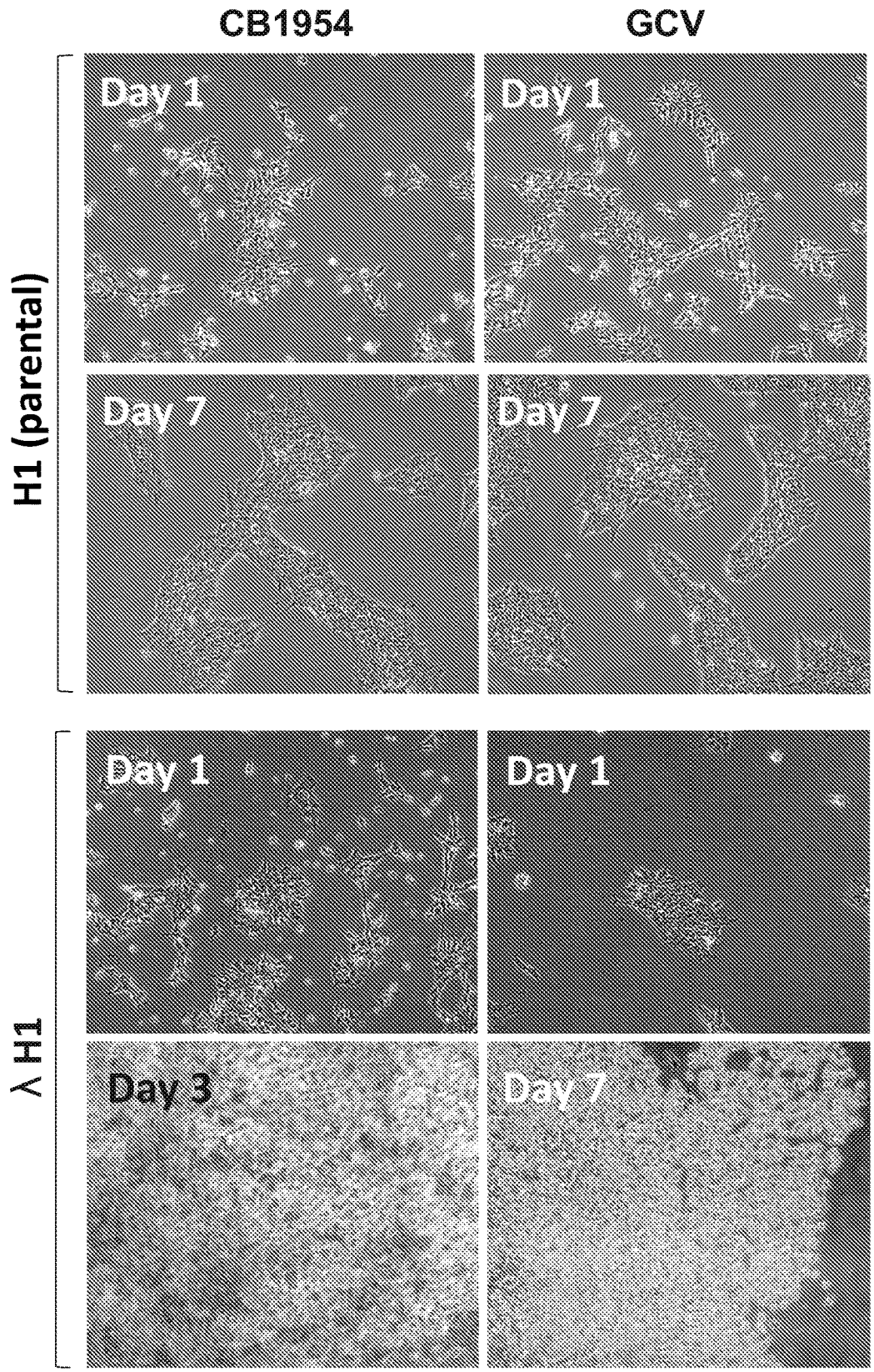
FIG. 8A is a set of images of λH1 cells or H1 cells treated with CB1954 (left column) or GCV (right column).
Figure 8B:
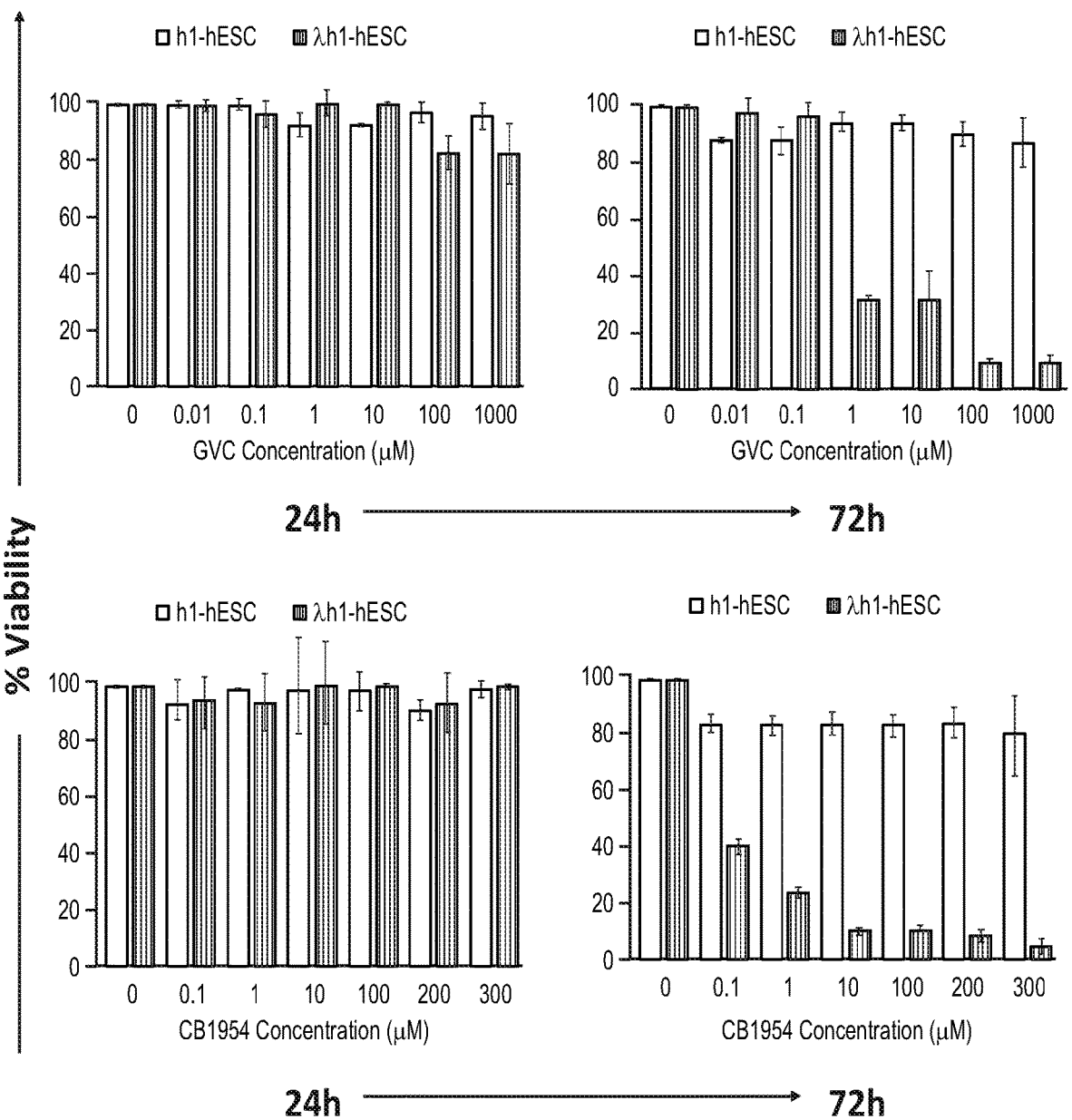
FIG. 8B is a set of graphs depicting the viability curve of both λH1 and H1 cells when exposed to the CB1954 or GCV dosages for 7 days. % viability is shown at 24 hours and 72 hours post treatment.
Figure 8C:
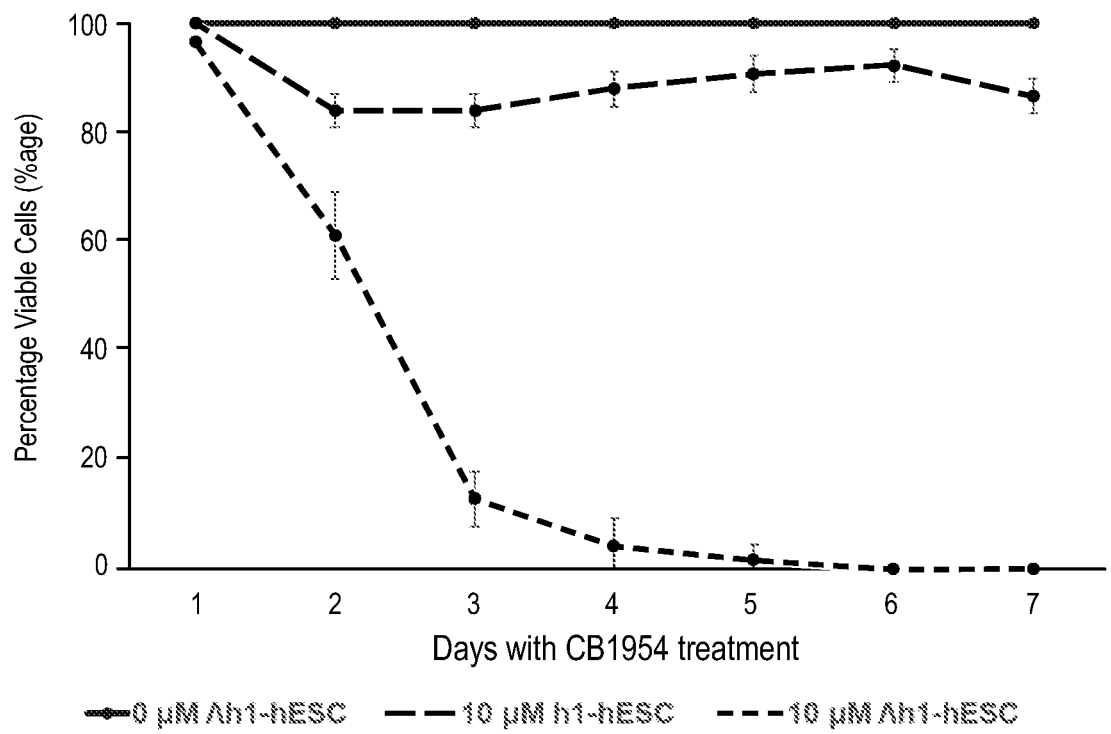
FIG. 8C is a pair of graphs demonstrating the percentage of viable cells expressed as a function of time after treatment with CB1954 (left graph) or with GCV (right graph).
Figure 8C:
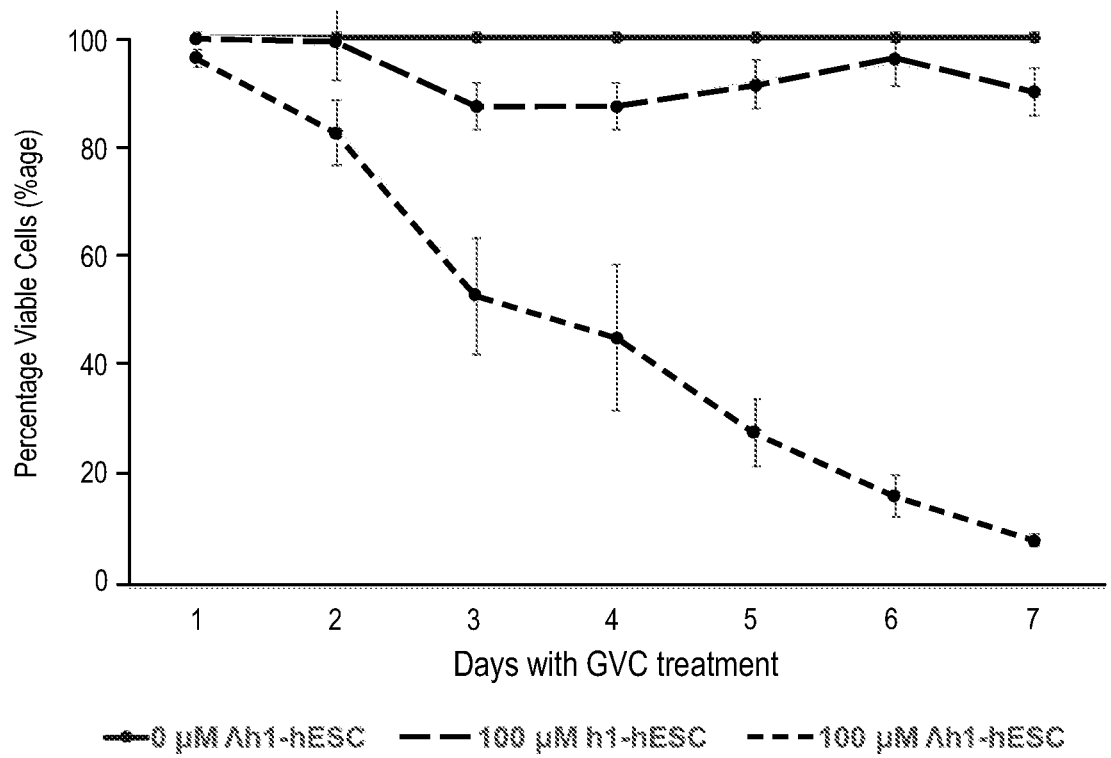
Figure 9A:
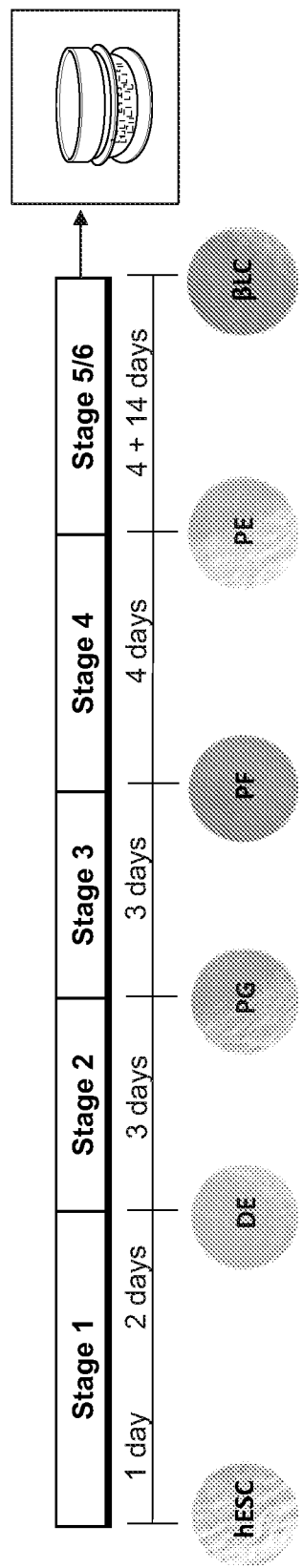
FIG. 9A is a series of photographs demonstrating an outline of the stages of the protocol (DE: definitive endoderm; PF: posterior foregut; PE: pancreatic endoderm; βLC: β-like cells).

A kill curve using different dosages for GCV (0.01 to 1000 μM) and CB1954 (0.1 to 300 μM) was done for λH1 and the parental H1 lines. Cell death was quantified by MTT [3-(4,5-dimethylthiazol-2-yl)-2,5-diphenyltetrazolium bromide] assays, which helped us determine the optimal concentration of each pro-drug that leads to ablation of undifferentiated λH1 cells while preserving the viability of the parental line within 7 days. Such concentration was in the range of 10-100 μM for both GCV and CB1954 (FIG. 8a), as previously reported in the literature for other cell types (21, 22). We used 10 μM for CB1954 and 100 μM of GCV for all subsequent experiments. FIG. 8b shows the viability curve of both λH1 and H1 cells when exposed to the above pro-drug dosages for 7 days. As shown in FIG. 8c, the parental H1 line is largely insensitive to either pro-drug, while most λH1 cells die just after 3 days of exposure to CB1954 and 7 days of exposure to GCV.

λH1 Cells are as Competent as their Parental Line to Differentiate Along the β-Cell Lineage Next, we proceeded to differentiate both λH1 and its parental cell line into β-like cells as described in Example 6. An outline of the stages of this protocol (DE: definitive endoderm; PF: posterior foregut; PE: pancreatic endoderm; βLC: β-like cells) is shown in FIG. 9a.

Figure 9B:
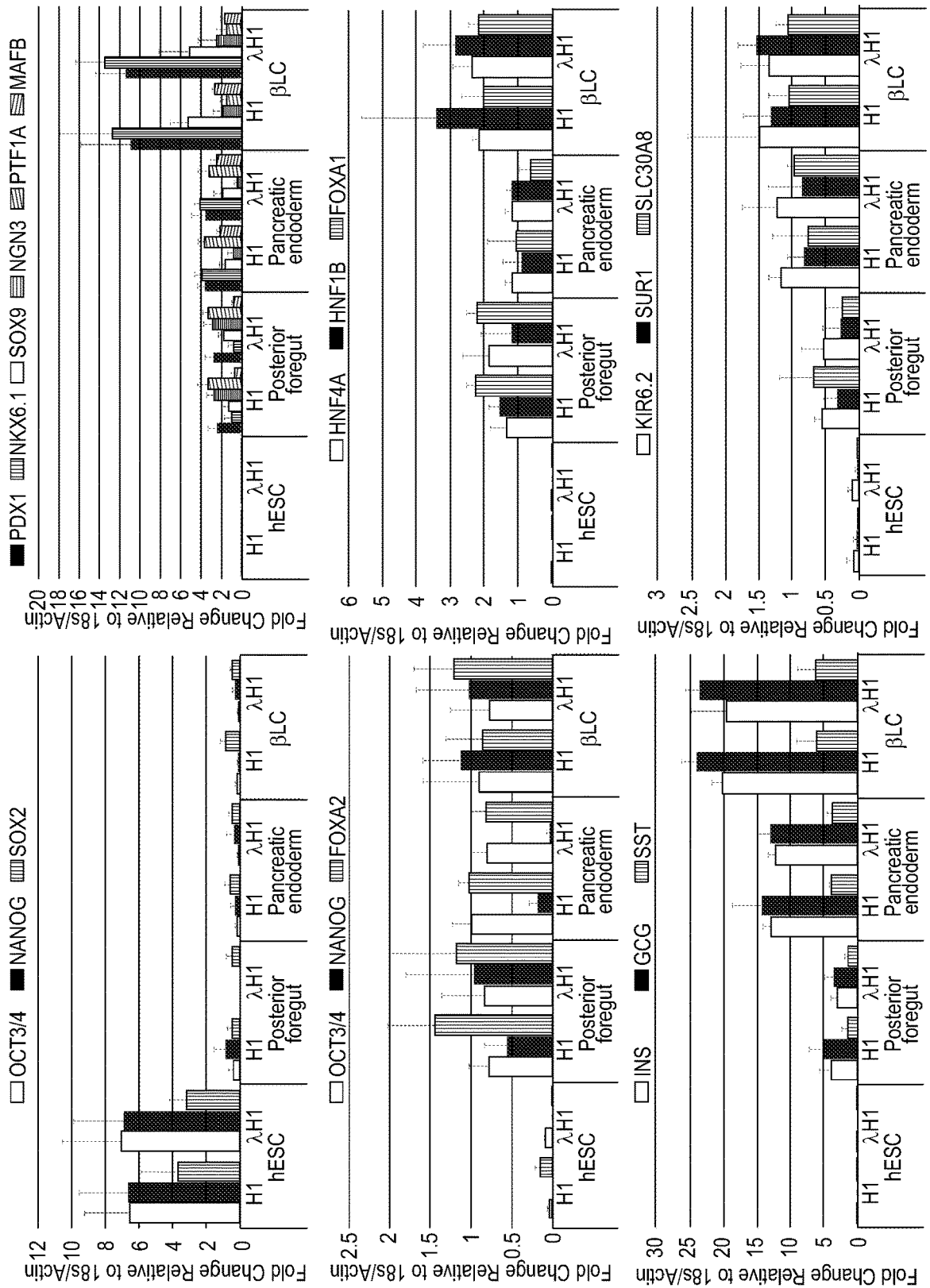
FIG. 9B is a series of graphs depicting gene expression patterns, as determined by qRT-PCR of a panel of representative genes at each stage.

Differentiation of λH1 and H1 cells was completed as indicated above. The gene expression pattern, as determined by qRT-PCR of a panel of representative genes at each stage, shows no statistical differences between λH1 and H1 cells at any of the stages analyzed (FIG. 9b). The percentage of the pancreatic progenitor markers PDX1+ and NKX6.1+ at the end of stage 4 (PE), which is used as a quality control for preparations prior to the last differentiation step (28), was similar for both the modified and the parental cell line (46.4 vs. 47.6%, respectively), and in line with previously reported results (2, 3, 27).

Figure 9C:
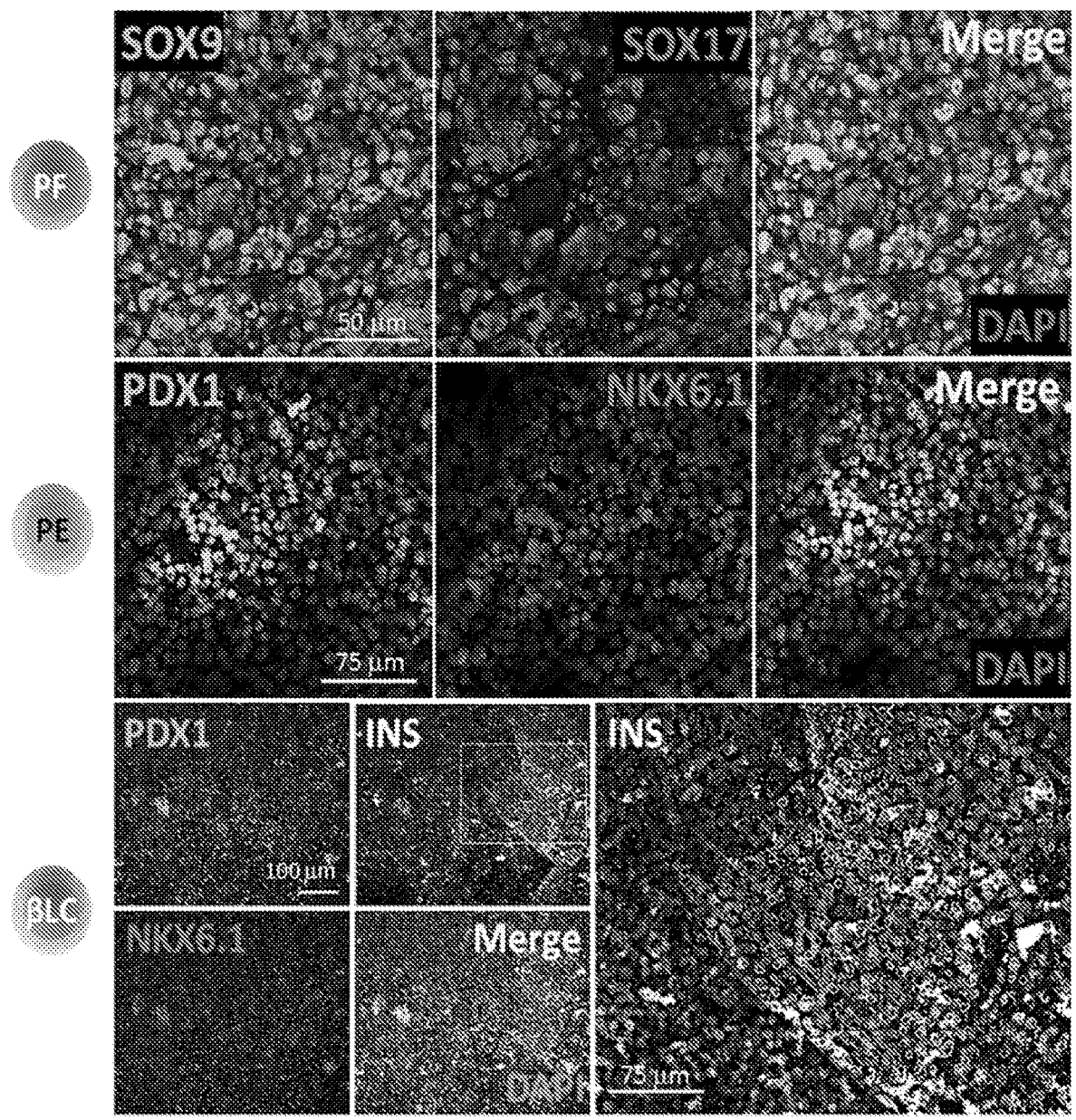
FIG. 9C is a series of representative immunofluorescent images at the different stages of differentiation (from PF onwards). The percentage of the pancreatic progenitor markers PDX1$^+$ and NKX6.1$^+$ at the end of stage 4 (PE), which is used as a quality control for preparations prior to the last differentiation step, was similar for both the modified and the parental cell line (46.4 vs. 47.6%, respectively), and in line with previously reported results. The bottom-right picture shows a magnified detail of the insulin staining at the last stage.

Representative immunofluorescence results at the different stages of differentiation (from PF onwards) are shown in FIG. 9c. The bottom-right picture shows a magnified detail of the insulin staining at the last stage. Of note, although we typically use C-peptide instead of insulin antibodies to make sure that the insulin is being produced and secreted by the cells and not taken up by the medium (29), in this particular case we trust the accuracy of insulin staining given that insulin is absent in all the defined media used throughout differentiation.

Suicide Constructs Function as Predicted after β-Cell Differentiation In Vitro

Figure 10A:
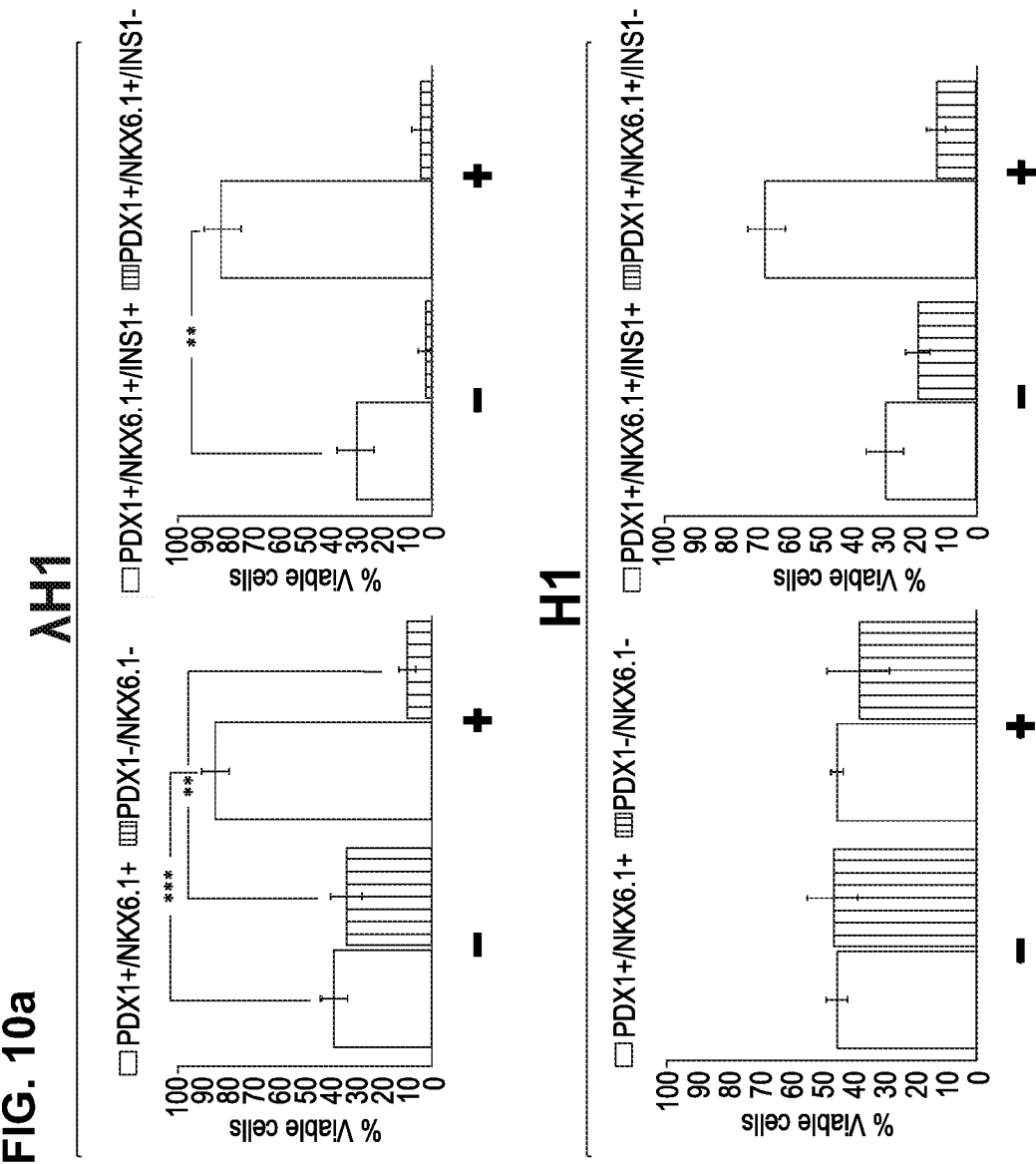
FIG. 10A is a series of graphs demonstrating the % viable cells under the indicated conditions: The top, left graph shows that the percentage of live λH1 cells that co-express PDX1 and NKX6.1 differs significantly between the untreated (38.3±6.3%, black column, left) and the treated (85.2±4.7%, black column, right) (P=0.0001). The top, right graph shows 29.6±7.5% of untreated vs. 81.7±6.4% of treated cells (P=0.004). The bottom graphs demonstrate that the parental H1 line does not show any statistically significant differences between treated and untreated groups.
Figure 10B:
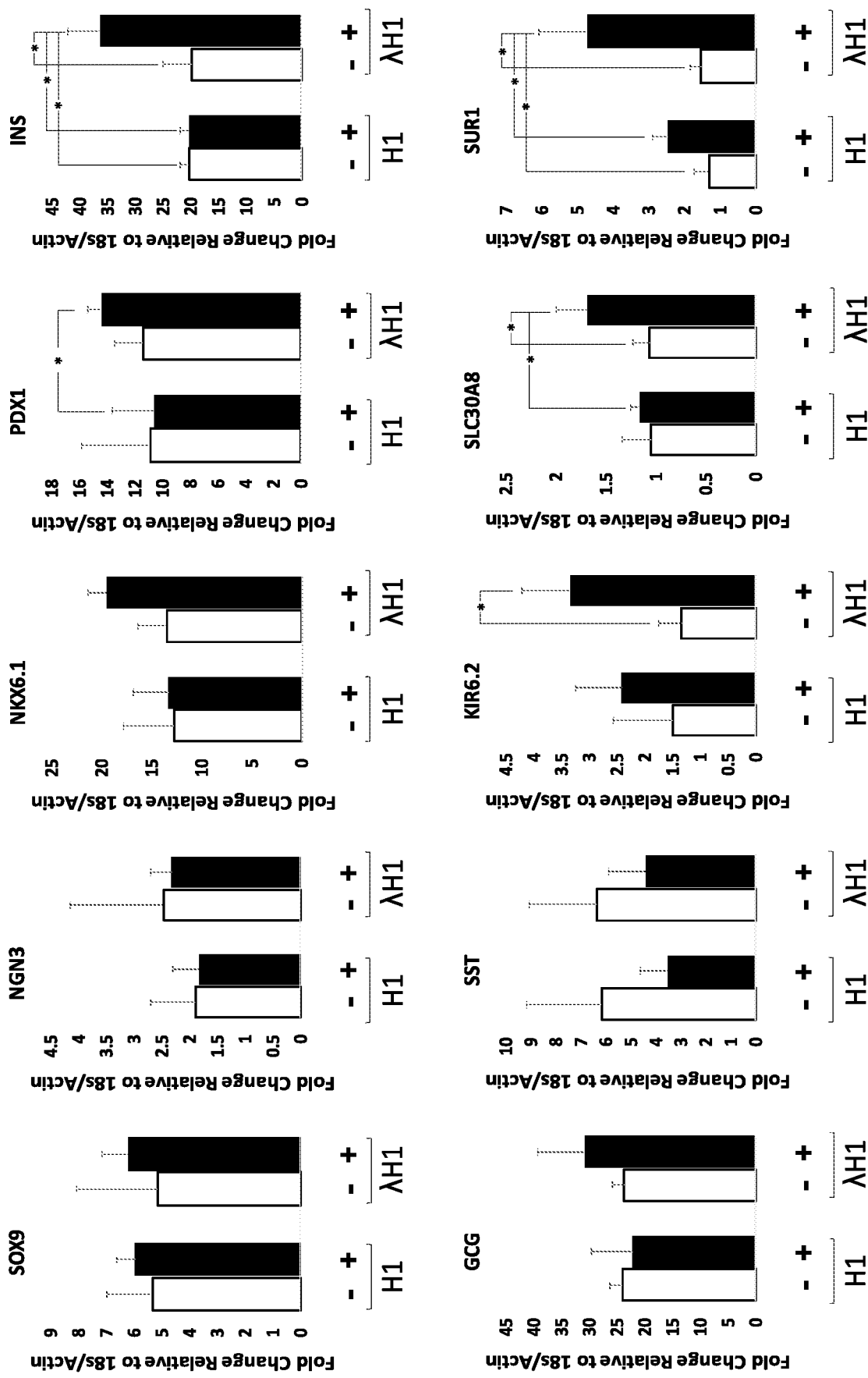
FIG. 10B is a series of graphs depicting the fold expression of the indicated pancreatic endocrine gene as measured by qRT-PCR at the conclusion of the experiment, for both treated and untreated λH1 and H1 cells.

Once differentiation was completed, we exposed cultures of both cell lines to CB1954 and GCV (10 and 100 μM, respectively) for 7 additional days, and analyzed the resulting populations by flow cytometry (n=3 independent experiments). Controls were kept in the same conditions, untreated, for the same length of time. As shown in FIG. 10a (top, left), the percentage of live λH1 cells that co-express PDX1 and NKX6.1 differs significantly between the untreated (38.3±6.3%, black column, left) and the treated (85.2±4.7%, black column, right) (P=0.0001). As it can be argued that PDX1 and NKX6.1 are also markers of undifferentiated β-cells, we further interrogated these populations for the marker combination PDX1$^+$/NKX6.1$^+$/INS$^+$, which represents a widely accepted β-cell signature (2, 3, 27). The same pattern held true, as shown in FIG. 10a (top, right): 29.6±7.5% of untreated vs. 81.7±6.4% of treated cells (P=0.004). As for the parental H1 line, there were no statistically significant differences between treated and untreated groups (FIG. 10a, bottom). To discard the possibility that the pro-drugs may negatively affect the phenotype of the selected β-like cells, we conducted a qRT-PCR analysis of key pancreatic endocrine genes at the conclusion of the experiment, for both treated and untreated λH1 and H1 cells. This analysis is presented in FIG. 10b. As expected, the parental line showed no significant differences in the expression of any of the studied genes between treated (red columns) and untreated (dark red) cells. Untreated λH1 cells (black columns) also exhibited the same pattern. In contrast, and surprisingly, the expression of insulin, the potassium channel subunit Kir6.2, the sulfonylurea receptor Sur1, and the zinc transporter SLC30A8 (all involved in the secretion of insulin by the β-cell) was significantly upregulated in the λH1 cells that received both pro-drugs (grey columns) vs. the untreated ones. These results suggest that, far from exerting a deleterious effect on the function of β-cells, selection and enrichment by the pro-drugs may in fact improve it. Furthermore, RNAseq analysis of pro-drug-selected cells indicates a high degree of hierarchical correlation with isolated pancreatic islets, but not with undifferentiated hESc (FIG. 10c). The comparison of specific pancreatic markers between islets and λH1-derived and selected β-like cells (FIG. 10d) further confirms the overall similitude of their transcriptional profile. Taken together, our data present evidence that: (1) λH1 cells are sensitive to both GCV and CB1954 when undifferentiated; and (2) treatment with the prodrugs upon differentiation induces a significant β-cell enrichment.

Figure 11A:
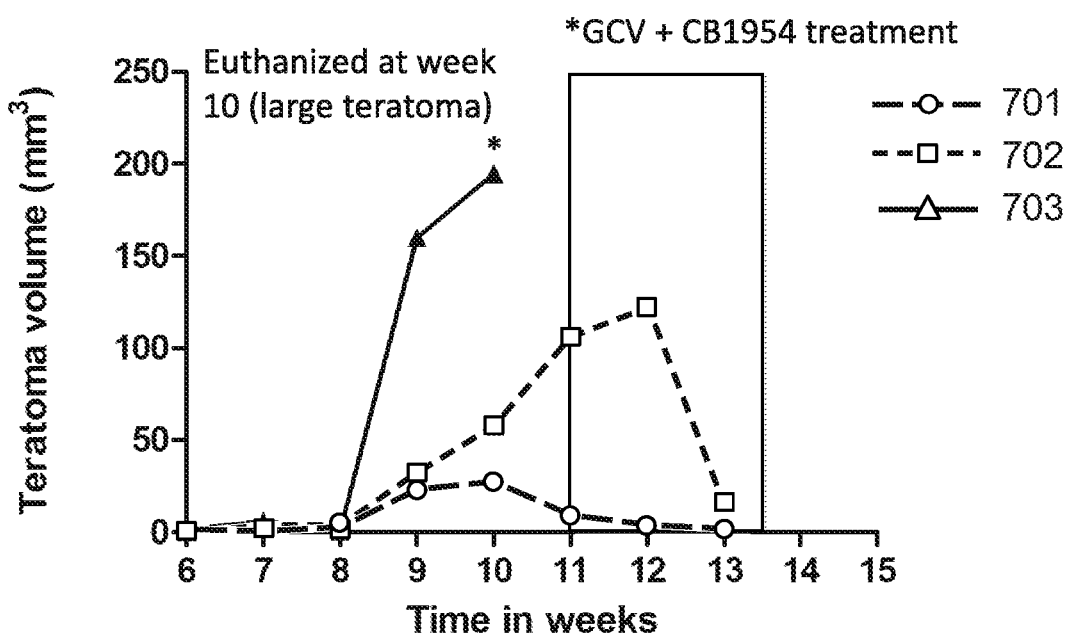
FIG. 11A is a graph of the teratoma volume ($mm^3$) of mice transplanted with H1 undifferentiated hES cells and treated with a combination of GCV and CB1954.

Treatment with Either GCV or CB1954 Prevents the Formation of and Eliminates Fully Formed Teratomas in Immunodeficient Mice Xenotransplanted with λH1 Cells In order to test whether our suicide gene strategy works as intended in vivo, 5×10$^6$ undifferentiated λH1 cells were transplanted subcutaneously in the left posterior dorsal flank of 5-6-week-old immunodeficient NOD-SCID mice. These conditions are known to result in the formation of teratomas within 6-9 weeks. Groups were assigned as follows:
1. Control (no treatment): 3 mice
2. Peri-transplantation treatment with GCV (40 mg/kg of body weight; 5 days, starting the 7$^{th}$ day after transplantation): 4 mice
3. Peri-transplantation treatment with CB1954 (20 mg/kg of body weight; 5 days, starting the 7$^{th}$ day after transplantation): 4 mice As described in the literature, tumors could be manually palpated and measured using calipers in the control group starting at week 6-7. At week 10, one of the mice was euthanized for histopathological characterization of the teratoma. Starting on week 11, we treated the remaining two mice with a combination of GCV and CB1954 to test the hypothesis that pro-drug administration would eliminate already formed tumors. As shown in FIG. 11a, this was indeed the case, as tumor volume recessed to near undetectable levels within 2 weeks of treatment (experiments still ongoing)

Figure 11B:
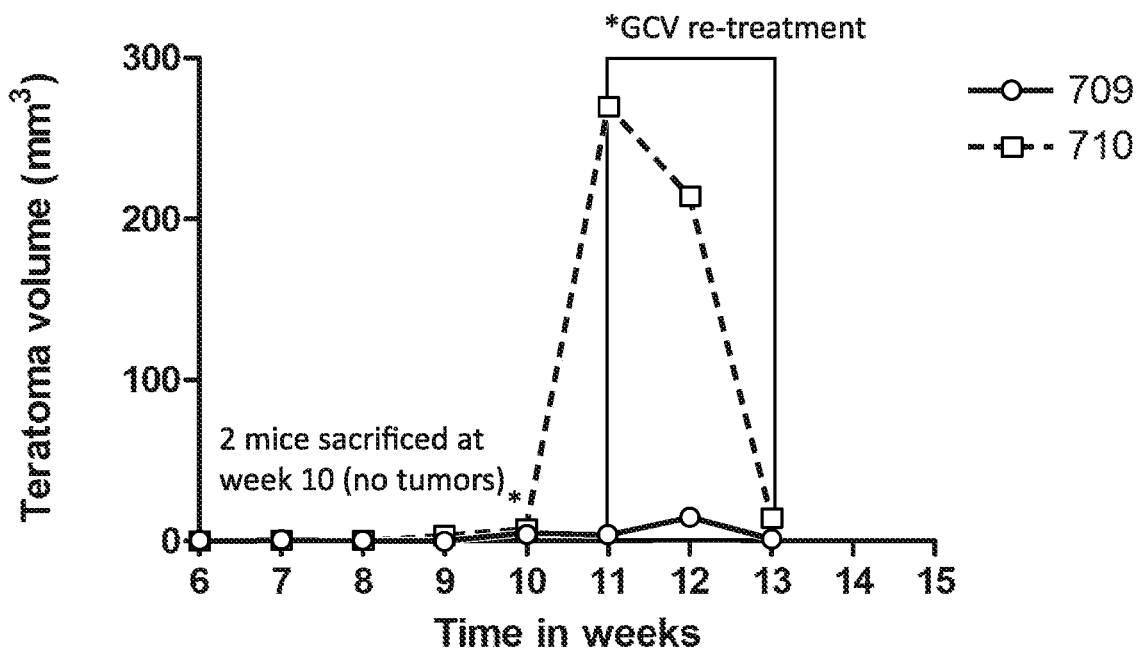
FIG. 11B is a graph of the teratoma volume ($mm^3$) of mice transplanted with H1 undifferentiated hES cells and re-treated with GCV.

No tumors could be detected in the ganciclovir-pretreated group up to week 10, 4 full weeks after tumors were first detected in the control group. Two mice in this group were euthanized at this point, showing no evidence of tumors (data not shown). However, manual palpation of the other two mice suggested the presence of very small teratomas, so we observed them for an additional week. During this period, the tumors grew significantly in both mice. This could be due to either the carry-over of residual hESc escapees that survived the initial GCV regimen, or to the development of GCV-resistant mutations in HSV-TK, as described in the literature. To test these two hypotheses, we re-treated these animals with ganciclovir in a 5-day drug/2-day rest regimen for the following two weeks. If the reason for the appearance of these late-onset tumors was resistance to the drug, we should continue to observe tumor growth despite the treatment; in contrast, if they were derived from surviving escapees, we might see tumor recession. Indeed, as shown in FIG. 11b, after a 2-week course of GCV re-treatment, both tumors virtually disappeared. This result is especially remarkable when considering that one of the mice had a very large tumor (>250 mm$^3$) at the initiation of the treatment. Finally, none of the animals in the third group (treated in the peri-transplantation period with CB1954) showed signs of tumor formation 11 weeks into the follow-up.

Discussion

It has been argued that, provided that the number of undifferentiated cells/batch is below the threshold known to produce teratomas in immunodeficient mice, hESc preparations are safe for transplantation (30). However, this strategy is based on statistical predictions, and does not take into account the risk of de-differentiation after engraftment (11). hESc-based therapies are predicted to reach millions. It would take only one incidence of tumorigenesis to bring the entire field to a screeching halt, perhaps for years. It is for this reason that key industry players are keen on adopting additional safeguards going to the clinic (see attached letters of support from Roslin Cells Ltd. and Semma Therapeutics). To this end, the use of suicide genes under constitutive promoters has been proposed (22). However, the pro-drug would kill the whole graft, including the cells for which there was a need in the first place. Considering the frequency at which teratogenic lesions are observed in some conditions, such safeguard would render the approach impractical. More recently, an hTERT-driven HSV-TK adenoviral transduction approach has been used with success for preclinical treatment of renal cell carcinoma (31). These findings reinforce the validity of our approach but do not replace it. Our method is innovative because it allows for the selective preservation and enrichment of the desired cells while destroying those with tumorigenic potential. The provision of a double failsafe mechanism is another novelty of our system, as tumorigenic escapees would be sensitive to not one but two pro-drugs. To our knowledge, no similar tactic has been described thus far. Also, as we intend to target the integration of this construct into a safe genomic harbor, the risks of insertional mutagenesis (32) are minimized. This has not been accomplished to date either. hESc lines modified in this fashion would be considered safe for transplantation.

The BIRC-5-GLuc reporter system is novel as well and will potentially streamline the necessary preclinical testing of the cell lines herein discussed. Finally, even if the experiments herein proposed are based on β-cell differentiation, our strategy will also be adapted for pan-endocrine cells (specific aim 2) in order to preserve the cross-talk between the different endocrine cell types that arise upon directed hESc differentiation (33). If successful, our strategy has far-reaching applications beyond diabetes. Selectivity could be adjusted for many other settings by simply replacing the insulin promoter by regulatory sequences specific to the cell type of interest (e.g., albumin promoter for hepatocytes, PNR promoter for retinal photoreceptor cells, GFAP for glial cells, etc.).

Example 6

This example demonstrates the methods and materials used in the experiments described in Example 5.

Cell Culture, Differentiation and MTT Growth Assays hESc (H1, National Stem Cell Registry #WA01, passage 35-45) were cultured as described in Schuldiner et al., PNAS USA 97: 11307-11312 (2000) using mTeSR™ (STEMCELL Technologies, Vancouver, Canada). The cells were differentiated along the β-cell lineage using a variation of our published protocol (Cechin et al., Stem Cells Translational Medicine 3: 277-289 (2014), which in turn is an adaptation of Razania et al., Nat Biotechnol 32: 1121-1133 (2014). In our version, the last maturation step is conducted in perfluorocarbon (PFC)-based dishes that provide a bi-directional oxygenation pattern to pancreatic progenitors. Such pattern has been shown to minimize $O_2$ diffusion gradients and hypoxia in 3D aggregates, while accurately targeting the β-cell physiological $pO_2$ range. A second variation is the removal of commonly used BMP inhibitors, as recently reported by Russ and colleagues. MTT (3-(4,5-dimethylthiazol-2-yl)-2,5-Diphenyltetrazolium Bromide) is a reagent which is converted from a soluble tetrazolium to its insoluble formazan form via the activity of mitochondrial NAD(P)H-dependent oxidoreductase activity. This can be used to evaluate growth and proliferation of hESC colonies. MTT growth assays were performed for the sensitivity of transfected colonies to neomycin, puromycin, GCV and CB1954 at varying concentrations as previously described.

Codon Optimization, Vector Construction and Plasmid Transfection

Cre recombinase (Cre), Herpes Simplex Virus Thymidine Kinase SR39 mutant (HSV-TKSR39) and Nitroreductase mutant T41L/N71 S (T41L/N71S-NTR) coding sequences were codon-usage optimized in silico to increase eukaryotic translational efficiency. This was performed using the OptimumGene™ Codon Optimization by GenScript (Piscataway, N.J.). Both suicide cassette sequences were synthesized using custom gene synthesis at GenScript. Construct A is 3665 bp and the sequence comprises a LoxP site followed by a CMV enhancer and promoter site, the T41L/N71 S-NTR sequence, a poly(A) signal, a SV40 promoter, aminoglycoside phosphotransferase gene, a SV40 poly(A) signal and a LoxP site. This sequence was subcloned into a pUC57 backbone (GenScript) using BstEII/NotI. Construct B is 4996 bp and is comprised of a human telomerase gene promoter, the HSV-TKSR39 sequence, a poly(A) signal, the human insulin promoter, Cre recombinase, Myc tag, β-globin poly(A) signal, the SV40 promoter, puromycin N-acetyltransferase gene and a SV40 poly(A) signal. This sequence was subcloned into a pPUR backbone (Clontech, Mountainview, Calif.) using BamHI/SapI. Constructs A and B were linearized using SspI and BamHI, respectively, and purified on a 2% agarose gel. The linearized plasmid was retrieved from the agarose using the QIAquick™ Gel Extraction Kit and the QIAquick™ PCR purification kit, both from Qiagen (Germantown, Md.). AT75 flask was coated with hESC-qualified Matrigel matrix solution comprising of 255 μl of Matrigel™ Matrix (Cat#354277, Lot #600473) (Corning, Corning, N.Y.) for 2 hours, and then washed three times with cold Dulbecco's Phosphate Buffered Saline (DPBS, Sigma-Aldrich, St. Louis, Mo.). H1 hESc were cultured until 70% confluent and then disassociated using the enzyme-free disassociation buffer ReLeSR™ (STEMCELL Technologies). Cells were carefully centrifuged at 300 rcf for five minutes, washed in DPBS and counted using 4% Trypan blue. Approximately 5 million cells were then resuspended in 800 μL transfection buffer containing mTeSR, HEPES buffer 10 mM and 40 μg linearized DNA. The cell suspension was then placed in a pre-chilled sterile Gene Pulser® cuvette (Bio-Rad, Hercules, Calif.). The cuvette's edges were wiped clean and then placed in the shocking chamber of a Bio-rad Gene Pulser® II Electroporation System. Voltage was set at 286V, high capacitance at 200 μF and maximum high capacitance to allow 500V. Following electroporation, the cells were then placed in fresh mTeSR containing 10 mM Y-27632 dihydrochloride (Sigma, Cat # Y0503), and plated onto a Matrigel-coated 100 mm×15 mm dish. After 24 hours, the cells were challenged with 100 μg/ml neomycin (Sigma, Cat # N1142) for Construct A. Resistant colonies were picked and passaged 6 times. PCR was used to determine construct integration and expression. Select expanded clones underwent a second electroporation procedure with Construct B. Stable integrants were selected using 3 μg/ml puromycin (Sigma, Cat # P9620). 26 clones generated were assessed for the integration and expression of both constructs after 6 passages. Subsequently, all the clones were frozen and stored at −196° C. in liquid Nitrogen cryotanks.

Fluorescence-Activated Cell Sorting (FACS) Analysis

FACS analyses of hESc and the hESc-derived differentiation products were performed on the FACSCalibur system (Becton Dickinson; Franklin Lakes, N.J.). SSEA4, TRA160R, SSEA3, Insulin, NKX6.1 and PDX1. Details on the antibodies used in these analyses as well as their dilution are provided in Table 1. Isotype controls were used to set background fluorescence. Analyses were completed using Kaluza FACS analysis software (Beckman Coulter, Brea, Calif.).

TABLE 1

| Antibody to | Concentration | | | | Cat | Reactivity |
| | IF | FACS | Host | Company | number | to Human |
| --- | --- | --- | --- | --- | --- | --- |
| SSEA3-AF647 | | 1:50 | Rat | BD Biosciences | 561145 | ++ |
| SSEA4-AF488 | | 1:100 | Mouse | STEMCELL Technologies | 60062AD | ++ |

TABLE 1-continued

| Antibody to | Concentration | | | Company | Cat number | Reactivity to Human |
|---|---|---|---|---|---|---|
| | IF | FACS | Host | | | |
| TRA-1-60R-PE | | 1:100 | Mouse | STEMCELL Technologies | 60064PE | ++ |
| PDX1 | 1:100 | 1:100 | Goat | R&D Systems | AF2419 | +++ |
| NKX6.1 | 1:50 | 1:50 | Goat | R&D Systems | AF5857 | +++ |
| Insulin | 1:300 | 1:300 | Guinea Pig | Dako | A0564 | +++ |
| FVD-eFluor780 | | 1:1000 | N/A | Invitrogen | 65-0865-14 | +++ |

Quantitative RT-PCR and Qualitative PCR

Total RNA was extracted using the mirVana™ miRNA Isolation Kit (Invitrogen, Cat # AM1560). cDNA was synthesized from 100 ng total RNA using the High-Capacity cDNA Reverse Transcription Kit (Invitrogen, Carlsbad, Calif.). cDNA samples were then subjected to PCR amplification with custom-designed primers for NTR and HSV-TK as well as previously described primers. For the NTR gene, the primers were: forward 5'-CCC-CACAGGCAGTGCT-3' (SEQ ID NO: 35); reverse 5'-GT-TAGTCCCGGGCAGTGTAG-3' (SEQ ID NO: 36); and the FAM probe 5'-TTGTCGCTCTGATCCC-3' (SEQ ID NO: 37). For the HSV-TK gene, the primers were: forward 5'-CCAAAGCAGCCAACGATAAGG-3' (SEQ ID NO: 38; reverse 5'-CCATCCACTCAGCATCGTCATG-3' (SEQ ID NO: 39); and the FAM probe 5'-TCGGCAAAGAATTTC-3' (SEQ ID NO: 40). Qualitative PCR was performed using surveyor primers designed to flank HSV-TK and NTR genes. For HSV-TK, the forward primer was 5'-CCCGGGACTAACATTGTGCT-3' (SEQ ID NO: 41); and the reverse primer 5'-CAGCTCGGGTGCTCTAAACA-3' (SEQ ID NO: 42). For NTR, the forward primer was 5'-CCTCACATGTGGTCGTGTTT-3' (SEQ ID NO: 43), and the reverse primer 5'-ACCTGTTTTGCCATCCACTC-3' (SEQ ID NO: 44). PCR was performed using the NEB interactive protocol design software (New England Biolabs, Ispwich, Mass.; available at the website at protocols.io/view/PCR-with-Taq-DNA-Polymerase-M0273-imst9m).

Mouse Transplantation Experiments

All animal experiments were conducted under the supervision of the University of Miami Institutional Animal Care and Use Committee (IACUC). NOD-SCID mice (5-6 weeks old; Jackson Laboratories, Bar Harbour, Me.) were housed in non-specific pathogen-free (SPF) conditions at the Division of Veterinary Resources (DVR). $5 \times 10^6$ hESc were resuspended in 50 µl mTeSR supplemented with 10 mM of the ROCK inhibitor Y-27632A, and subsequently mixed with undiluted Matrigel of equal volume. The cell suspension was injected into the subcutis of the left posterior dorsal flank of the animal. Tumor growth was monitored with a caliper. Mice were euthanized after the observation/re-treatment period, as described in the Results section. Euthanized animals were subject to general observation. The injection site was inspected and tumor tissue, if present, was collected and processed for histopathological analysis. Lungs, liver spleen and pancreas were also harvested for histological analysis of potential tumor invasion.

Histological Analysis, Immunofluorescence Staining and Cellular Imaging

Cells for Immunofluorescence staining were cultured in 4 well chambered slides (NUNC™ Lab-Tek™ Chamber Slide™ System; Thermo Fisher Scientific, Waltham, Mass.) coated with Matrigel. Cells were then fixed with 4% paraformaldehyde. Tumors and tissues were also fixed overnight in 4% paraformaldehyde. Immunofluorescence was performed as previously described in Cechin et al, 2014 (3).

REFERENCES

The following references are cited in Examples 1-4 and Background.
1. Kroon et al., Nat Biotechnol 26, 443-452 (2008).
2. Schulz et al., PLoS One 7 (5): e37004 (2012).
3. Cechin et al., Stem cells translational medicine 3, 277-289, (2014).
4. Pagliuca et al., Cell 159, 428-439, (2014).
5. Rezania et al., Nat Biotechnol 32, 1121-1133, (2014).
6. Russ et al. EMBO J 34, 1759-1772, (2015).
7. Vegas et al., Nat Med 22, 306-311, (2016).
8. Yoshihara et al., Cell Metab 23, 622-634 (2016).
9. Dominguez-Bendala et al., Trends Endocrinol Metab, 37(3): 153-162 (2016).
10. Thomson et al., Science 282, 1145-1147 (1998).
11. Fujikawa et al., Am J Pathol 166, 1781-1791 (2005).
12. Hori et al., Proc Natl Acad Sci USA 99, 16105-16110 (2002).
13. Sipione et al., Diabetologia 47, 499-508 (2004).
14. Odorico et al., Stem Cells 19, 193-204 (2001).
15. Fox, J. L. Nat Biotechnol 26, 598-599 (2008).
16. Tamada et al., World J Surg 29, 325-333 (2005).
17. Wang et al., J Gastrointest Surg 8, 98-108; discussion 106-108 (2004).
18. Yazawa et al., World J Surg 26, 783-789 (2002).
19. Schuldiner et al., Stem Cells 21, 257-265 (2003).
20. Fareed et al., Gene Ther 9, 955-962 (2002).
21. Nishiyama et al., J Gen Virol 45, 227-230 (1979).
22. Elion, Adv Enzyme Regul 18, 53-66 (1980).
23. Moolten, Cancer Res 46, 5276-5281 (1986).
24. Grove et al., Anticancer Drug Des 14, 461-472 (1999).
25. Bridgewater et al., Eur J Cancer 31A, 2362-2370 (1995).
26. Clark et al., Gene Ther 4, 101-110 (1997).
27. Drabek et al., Gene Ther 4, 93-100 (1997).
28. Williams et al., Biochem J 471, 131-153, (2015).
29. Kos, Nutr Rev 62, 243-246 (2004).
30. Kuhn and Torres, Methods Mol Biol 180, 175-204 (2002).
31. Yoshimura et al., Mol Urol 5, 81-84 (2001).
32. Albanell et al., J Natl Cancer Inst 91, 1321-1326 (1999).
33. Kozak, Nucleic Acids Res 15, 8125-8148 (1987).
34. Vogel, Science 308, 1534-1538 (2005).
35. Baum et al., Hum Gene Ther 17, 253-263 (2006).
36. Mikkers & Berns, Adv Cancer Res 88, 53-99 (2003).
37. Belteki et al., Nucleic Acids Res 33, e51 (2005).
38. Irion et al., Nat Biotechnol 25, 1477-1482 (2007).

The following references are cited in Examples 5-6.
1. Schulz T C, et al. (2012) PLoS One 7(5):e37004.
2. Pagliuca F W, et al. (2014) Cell 159(2):428-439.

3. Rezania A, et al. (2014) *Nat Biotechnol* 32(11):1121-1133.
4. Dominguez-Bendala et al., (2016) *Trends Endocrinol Metab.*
5. Kroon E, et al. (2008) *Nat Biotechnol* 26(4):443-452.
6. Fareed M U & Moolten F L (2002) *Gene Ther* 9(14): 955-962.
7. Grove J I, et al. (1999) *Anticancer Drug Des* 14(6):461-472.
8. Williams E M, et al. (2015) *Biochem J* 471(2):131-153.
9. Kuhn R & Torres R M (2002) *Methods Mol Biol* 180: 175-204.
10. Albanell J, et al. (1999) *J Natl Cancer Inst* 91(15):1321-1326.
11. Fujikawa T, et al. (2005) *Am J Pathol* 166(6):1781-1791.
12. Schuldiner et al., *Proc Natl Acad Sci USA* 97, 11307-11312 (2000).
13. Cechin et al., *Stem cells translational medicine* 3, 277-289 (2014).
14. Fraker C A, et al., *Stem Cells* 25, 3155-3164 (2007).
15. Fraker C A, et al., *Cell Transplant* 22, 1723-1733 (2013).
16. Fraker C, et al., *Biology of the Cell* 101, 431-440 (2009).
17. Russ H A, et al. *EMBO J* 34, 1759-1772 (2015).
18. Behar et al., *Curr Protoc Stem Cell Biol* Chapter 1, Unit 1C 13 (2012).
19. Nagy A. *Genesis* 26, 99-109 (2000).
20. Searle P F, et al., *Clin Exp Pharmacol Physiol* 31, 811-816 (2004).
21. Schipper et al., *Mol Imaging Biol* 9, 110-116 (2007).
22. Klatzmann D, et al. *Hum Gene Ther* 9, 2585-2594 (1998).
23. Karjoo et al., *Adv Drug Deliv Rev* 99, 113-128 (2016).
24. Black et al., *Cancer Res* 61, 3022-3026 (2001).
25. Qasim et al., *Gene Ther* 9, 824-827 (2002).
26. Odagiri et al., *J Biol Chem* 271, 1909-1915 (1996).
27. Kozak M. *Nucleic Acids Res* 15, 8125-8148 (1987).
28. Felmer and Clark, *Biol Res* 37, 449-460 (2004).
29. Schuldiner et al., *Stem Cells* 21, 257-265 (2003).
30. Rezania A, et al. *Stem Cells*, (2013).
31. Hansson M, et al. *Diabetes* 53, 2603-2609 (2004).
32. Vogel G. *Science* 308, 1534-1538 (2005).
33. Tian D, et al., *Onco Targets Ther* 6, 419-426 (2013).
34. Baum C, et al., *Hum Gene Ther* 17, 253-263 (2006).
35. Cabrera et al., *Proc Natl Acad Sci USA* 103, 2334-2339 (2006).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of treating diabetes in a subject in need thereof, comprising
   a. administering to the subject stem cells comprising a recombinant expression vector system comprising a first suicide gene and a second suicide gene, wherein the first suicide gene is excised via action of a recombinase in cells exhibiting a phenotype of a differentiated pancreatic cell, and wherein expression of the second suicide gene in the cell is controlled by a promoter that is active in a cancer or tumor cell,
   wherein expression of the recombinase is controlled by an islet beta cell-specific promoter, and wherein the promoter that is active in a cancer or tumor cell is a telomerase promoter, BIRC5 (survivin) promoter or hTERT-CMV promoter; and
   b. administering to the subject an agent which causes death of cells expressing the first suicide gene or the second suicide gene.

2. The method of claim 1, wherein the recombinase is selected from Cre, FLT, and Tre recombinases.

3. The method of claim 2, wherein the suicide gene which is excised by the action of the recombinase is flanked by two loxP sites, two FRT sites, or two HIV markers in the recombinant expression vector system.

4. The method of claim 1, wherein the islet beta cell-specific promoter is an insulin promoter.

5. The method of claim 1, wherein the promoter that is active in a cancer or tumor cell is a human telomerase promoter.

6. The method of claim 1, wherein the first suicide gene and/or the second suicide gene encodes a heterologous enzyme that metabolizes an inactive prodrug into a cytotoxin.

7. The method of claim 1, wherein the expression of the first suicide gene is controlled by a constitutive promoter.

8. The method of claim 1, wherein the first suicide gene and the second suicide gene are present on the same recombinant expression vector.

9. The method of claim 1, wherein the recombinant vector system comprises two or more recombinant expression vectors, wherein at least one first recombinant expression vector comprises the first suicide gene excised via action of a recombinase in cells exhibiting a phenotype of a differentiated cell, and at least one second recombinant expression vector comprises the second suicide gene.

10. The method of claim 6, wherein the wherein the first suicide gene and/or the second suicide gene is thymidine kinase, guanine phosphoribosyl transferase, cytosine deaminase-5-fluorocytosine, cytochrome P450-ifosfamide, cytochrome P450-cyclophosphamide, nitroreductase-5-[aziridin-1-yl]-2,4-dinitrobenzamide, carboxypeptidase G2, or purine nucleoside phosphorylase.

11. The method of claim 7, wherein the constitutive promoter is CMV, SV40, UBC, EF1A, PGK, or CAGG.

* * * * *

SEQUENCE LISTING

```
<160> NUMBER OF SEQ ID NOS: 44

<210> SEQ ID NO 1
<211> LENGTH: 6560
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: pUC57LoxNRNeoRLox

<400> SEQUENCE: 1
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
```

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cctagagacg gatcgggaga    420
tctcccgatc ccctatggtg cactctcagt acaatctgct ctgatgccgc atagttaagc    480
cagtatctgc tccctgcttg tgtgttggag gtcgctgagt agtgcgcgag caaaatttaa    540
gctacaacaa ggcaaggctt gaccgacaat tgcatgaaga atctgcttag ggttaggcgt    600
tttgcgctgc ttcgcgaggt aaccataact tcgtatagca tacattatac gaagttattg    660
tacgggccag atatacgcgt tgacattgat tattgactag ttattaatag taatcaatta    720
cggggtcatt agttcatagc ccatatatgg agttccgcgt tacataactt acggtaaatg    780
gcccgcctgg ctgaccgccc aacgaccccc gcccattgac gtcaataatg acgtatgttc    840
ccatagtaac gccaataggg actttccatt gacgtcaatg ggtggagtat ttacggtaaa    900
ctgcccactt ggcagtacat caagtgtatc atatgccaag tacgccccct attgacgtca    960
atgacggtaa atggcccgcc tggcattatg cccagtacat gaccttatgg gactttccta   1020
cttggcagta catctacgta ttagtcatcg ctattaccat ggtgatgcgg ttttggcagt   1080
acatcaatgg gcgtggatag cggtttgact cacggggatt tccaagtctc cacccccattg  1140 acgtcaatgg gagtttgttt tggcaccaaa atcaacggga ctttccaaaa tgtcgtaaca   1200
actccgcccc attgacgcaa atgggcggta ggcgtgtacg gtgggaggtc tatataagca   1260
gagctctctg gctaactaga gaacccactg cttactggct tatcgaaatt aatacgactc   1320
actataggga gacccaagct ggctagcgtt taaacttaag cttggtacgc caccatggac   1380
atcatttcag tggcactgaa gcgacacagc actaaagcat tcgatgcctc caagaaactg   1440
actcccgagc aggctgaaca gatcaagacc ctgctgcagt actctccaag ctccctgaac   1500
agtcagccct ggcactttat tgtggcctct acagaggaag gaaaggctag ggtggcaaaa   1560
tctgccgctg gcaattacgt gttcagcgag cgcaagatgc tggacgcctc acatgtggtc   1620
gtgttttgcg ccaagaccgc tatggacgac gtgtggctga aactggtcgt ggaccaggag   1680
gacgccgatg ggagattcgc aacacctgaa gccaaagcag ccaacgataa gggacggaaa   1740
ttctttgccg acatgcacag aaaggatctg catgacgatg ctgagtggat ggcaaaacag   1800
gtgtacctga acgtcggcaa ttttctgctg ggagtggctg cactgggact ggacgccgtc   1860
cctatcgaag gcttcgacgc cgctattctg gatgctgagt ttggcctgaa ggaaaaaggg   1920
tatacaagcc tggtcgtggt cccagtgggg caccattccg tcgaggattt caacgccact   1980
ctgcccaagt cccggctgcc tcagaatatc accctgacag aagtgtgatg accgctgatc   2040
agcctttaat taacgactgt gccttctagt tgccagccat ctgttgtttg ccctccccc    2100 gtgccttcct tgaccctgga aggtgccact cccactgtcc tttcctaata aaatgaggaa   2160
attgcatcgc attgtctgag taggtgtcat tctattctgg ggggtggggt ggggcaggac   2220
agcaaggggg aggattggga agacaatagc aggcatgctg gggatgcggt gggctctatg   2280
gcttctgagg cggaaagaac cagctggggc tctaggggt atccccacgc gccctgtagc    2340
ggcgcattaa gcgcggcggg tgtggtggtt acgcgcagcg tgaccgctac acttgccagc   2400
gccctagcgc ccgctccttt cgctttcttc ccttcctttc tcgccacgtt cgccggcttt   2460
ccccgtcaag ctctaaatcg ggggctccct ttagggttcc gatttagtgc tttacggcac   2520
ctcgacccca aaaaacttga ttagggtgat ggttcacgta gtgggccatc gccctgatag   2580
```

```
acggtttttc gcccttttgac gttggagtcc acgttcttta atagtggact cttgttccaa    2640
actggaacaa cactcaaccc tatctcggtc tattcttttg atttataagg gattttgccg    2700
atttcggcct attggttaaa aaatgagctg atttaacaaa aatttaacgc gaattaattc    2760
tgtggaatgt gtgtcagtta gggtgtggaa agtccccagg ctccccagca ggcagaagta    2820
tgcaaagcat gcatctcaat tagtcagcaa ccaggtgtgg aaagtcccca ggctccccag    2880
caggcagaag tatgcaaagc atgcatctca attagtcagc aaccatagtc ccgcccctaa    2940
ctccgcccat cccgccccta actccgccca gttccgccca ttctccgccc catggctgac    3000 taatttttt tatttatgca gaggccgagg ccgcctctgc ctctgagcta ttccagaagt    3060
agtgaggagg cttttttgga ggcctaggct tttgcaaaaa gctcccggga gcttgtatat    3120
ccattttcgg atctgatcaa gagacaggat gaggatcgtt tcgcatgatt gaacaagatg    3180
gattgcacgc aggttctccg gccgcttggg tggagaggct attcggctat gactgggcac    3240
aacagacaat cggctgctct gatgccgccg tgttccggct gtcagcgcag ggcgcccgg    3300 ttcttttgt caagaccgac ctgtccgtg ccctgaatga actgcaggac gaggcagcgc    3360
ggctatcgtg gctggccacg acgggcgttc cttgcgcagc tgtgctcgac gttgtcactg    3420
aagcgggaag ggactggctg ctattgggcg aagtgccggg gcaggatctc ctgtcatctc    3480
accttgctcc tgccgagaaa gtatccatca tggctgatgc aatgcggcgg ctgcatacgc    3540
ttgatccggc tacctgccca ttcgaccacc aagcgaaaca tcgcatcgag cgagcacgta    3600
ctcggatgga agccggtctt gtcgatcagg atgatctgga cgaagagcat caggggctcg    3660
cgccagccga actgttcgcc aggctcaagg cgcgcatgcc cgacggcgag gatctcgtcg    3720
tgacccatgg cgatgcctgc ttgccgaata tcatggtgga aaatggccgc ttttctggat    3780
tcatcgactg tggccggctg ggtgtggcgg accgctatca ggacatagcg ttggctaccc    3840
gtgatattgc tgaagagctt ggcggcgaat gggctgaccg cttcctcgtg ctttacggta    3900
tcgccgctcc cgattcgcag cgcatcgcct tctatcgcct tcttgacgag ttcttctgag    3960
cgggactctg gggttcgaaa tgaccgacca agcgacgccc aacctgccat cacgagattt    4020
cgattccacc gccgccttct atgaaaggtt gggcttcgga atcgttttcc gggacgccgg    4080
ctggatgatc ctccagcgcg gggatctcat gctggagttc ttcgcccacc ccaacttgtt    4140
tattgcagct tataatggtt acaaataaag caatagcatc acaaatttca caaataaagc    4200 attttttca ctgcattcta gttgtggttt gtccaaactc atcaatgtat cttatataac    4260
ttcgtatagc atacattata cgaagttatg cggccgcgtc gactgcagag gcctgcatgc    4320
aagcttggcg taatcatggt catagctgtt tcctgtgtga aattgttatc cgctcacaat    4380
tccacacaac atacgagccg gaagcataaa gtgtaaagcc tggggtgcct aatgagtgag    4440
ctaactcaca ttaattgcgt tgcgctcact gcccgctttc cagtcgggaa acctgtcgtg    4500
ccagctgcat taatgaatcg gccaacgcgc ggggagaggc ggtttgcgta ttgggcgctc    4560
ttccgcttcc tcgctcactg actcgctgcg ctcggtcgtt cggctgcggc gagcggtatc    4620
agctcactca aaggcggtaa tacggttatc cacagaatca ggggataacg caggaaagaa    4680
catgtgagca aaaggccagc aaaaggccag gaaccgtaaa aaggccgcgt tgctggcgtt    4740
tttccatagg ctccgccccc ctgacgagca tcacaaaaat cgacgctcaa gtcagaggtg    4800
gcgaaacccg acaggactat aaagatacca ggcgtttccc cctggaagct ccctcgtgcg    4860
ctctcctgtt ccgaccctgc cgcttaccgg atacctgtcc gcctttctcc cttcgggaag    4920
cgtggcgctt tctcatagct cacgctgtag gtatctcagt tcggtgtagg tcgttcgctc    4980
```

```
caagctgggc tgtgtgcacg aaccccccgt tcagcccgac cgctgcgcct tatccggtaa    5040
ctatcgtctt gagtccaacc cggtaagaca cgacttatcg ccactggcag cagccactgg    5100
taacaggatt agcagagcga ggtatgtagg cggtgctaca gagttcttga agtggtggcc    5160
taactacggc tacactagaa gaacagtatt tggtatctgc gctctgctga agccagttac    5220
cttcggaaaa agagttggta gctcttgatc cggcaaacaa accaccgctg gtagcggtgg    5280
tttttttgtt tgcaagcagc agattacgcg cagaaaaaaa ggatctcaag aagatccttt    5340
gatcttttct acggggtctg acgctcagtg gaacgaaaac tcacgttaag gattttggt    5400 catgagatta tcaaaaagga tcttcaccta gatccttta aattaaaaat gaagttttaa    5460
atcaatctaa agtatatatg agtaaacttg gtctgacagt taccaatgct taatcagtga    5520
ggcacctatc tcagcgatct gtctatttcg ttcatccata gttgcctgac tccccgtcgt    5580
gtagataact acgatacggg agggcttacc atctggcccc agtgctgcaa tgataccgcg    5640
agacccacgc tcaccggctc cagatttatc agcaataaac cagccagccg aagggccga    5700 gcgcagaagt ggtcctgcaa ctttatccgc ctccatccag tctattaatt gttgccggga    5760
agctagagta agtagttcgc cagttaatag tttgcgcaac gttgttgcca ttgctacagg    5820
catcgtggtg tcacgctcgt cgtttggtat ggcttcattc agctccggtt cccaacgatc    5880
aaggcgagtt acatgatccc ccatgttgtg caaaaaagcg gttagctcct tcggtcctcc    5940
gatcgttgtc agaagtaagt tggccgcagt gttatcactc atggttatgg cagcactgca    6000
taattctctt actgtcatgc catccgtaag atgcttttct gtgactggtg agtactcaac    6060
caagtcattc tgagaatagt gtatgcggcg accgagttgc tcttgcccgg cgtcaatacg    6120
ggataatacc gcgccacata gcagaacttt aaaagtgctc atcattggaa aacgttcttc    6180
ggggcgaaaa ctctcaagga tcttaccgct gttgagatcc agttcgatgt aacccactcg    6240
tgcacccaac tgatcttcag catctttac tttcaccagc gtttctgggt gagcaaaaac    6300
aggaaggcaa aatgccgcaa aaaagggaat aagggcgaca cggaaatgtt gaatactcat    6360
actcttcctt tttcaatatt attgaagcat ttatcagggt tattgtctca tgagcggata    6420
catatttgaa tgtatttaga aaaataaaca aataggggtt ccgcgcacat ttccccgaaa    6480
agtgccacct gacgtctaag aaaccattat tatcatgaca ttaacctata aaaataggcg    6540
tatcacgagg ccctttcgtc                                               6560

<210> SEQ ID NO 2
<211> LENGTH: 7862
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: pPURHtertpTKHipCre

<400> SEQUENCE: 2
tggaatgtgt gtcagttagg gtgtggaaag tccccaggct ccccagcagg cagaagtatg      60
caaagcatgc atctcaatta gtcagcaacc aggtgtggaa agtccccagg ctccccagca    120
ggcagaagta tgcaaagcat gcatctcaat tagtcagcaa ccatagtccc gcccctaact    180
ccgcccatcc cgcccctaac tccgcccagt tccgcccatt ctccgcccca tggctgacta    240 attttttta tttatgcaga ggccgaggcc gcctcggcct ctgagctatt ccagaagtag    300
tgaggaggct ttttggagg cctaggcttt tgcaaaaagc ttgcatgcct gcaggtcggc    360
```

```
cgccacgacc ggtgccgcca ccatcccctg acccacgccc ctgacccctc acaaggagac      420
gaccttccat gaccgagtac aagcccacgg tgcgcctcgc cacccgcgac gacgtccccc      480
gggccgtacg cacccccgcc gccgcgttcg ccgactaccc cgccacgcgc cacaccgtcg      540
acccggaccg ccacatcgag cgggtcaccg agctgcaaga actcttcctc acgcgcgtcg      600
ggctcgacat cggcaaggtg tgggtcgcgg acgacggcgc gcggtggcg gtctggacca       660 cgccggagag cgtcgaagcg ggggcggtgt tcgccgagat cggcccgcgc atggccgagt      720
tgagcggttc ccggctggcc gcgcagcaac agatggaagg cctcctggcg ccgcaccggc      780
ccaaggagcc cgcgtggttc ctggccaccg tcggcgtctc gcccgaccac cagggcaagg      840
gtctgggcag cgccgtcgtg ctccccggag tggaggcggc cgagcgcgcc ggggtgcccg      900
ccttcctgga gacctccgcg ccccgcaacc tccccttcta cgagcggctc ggcttcaccg      960
tcaccgccga cgtcgagtgc ccgaaggacc gcgcgacctg gtgcatgacc cgcaagcccg     1020
gtgcctgacg cccgccccac gaccgcagc gcccgaccga aggagcgca cgaccccatg      1080 gctccgaccg aagccgaccc gggcggcccc gccgaccccg caccgcccc cgaggcccac      1140 cgactctaga ggatcataat cagccatacc acatttgtag aggttttact tgctttaaaa      1200
aacctcccac acctccccct gaacctgaaa cataaaatga atgcaattgt tgttgttaac      1260
ttgtttattg cagcttataa tggttacaaa taaagcaata gcatcacaaa tttcacaaat      1320
aaagcatttt tttcactgca ttctagttgt ggtttgtcca aactcatcaa tgtatcttat      1380
catgtctgga tccccaggaa gctcctctgt gtcctcataa accctaacct cctctacttg      1440
agaggacatt ccaatcatag gctgcccatc caccctctgt gtcctcctgt taattaggtc      1500
acttaacaaa aaggaaattg ggtaggggtt tttcacagac cgctttctaa gggtaatttt      1560
aaaatatctg ggaagtccct tccactgctg tgttccagaa gtgttggtaa acagcccaca      1620
aatgtcaaca gcagaaacat acaagctgtc agctttgcac aagggcccaa caccctgctc      1680
atcaagaagc actgtggttg ctgtgttagt aatgtgcaaa acaggaggca catttttccc      1740
acctgtgtag gttccaaaat atctagtgtt ttcattttta cttggatcag gaacccagca      1800
ctccactgga taagcattat ccttatccaa aacagcttg tggtcagtgt tcatctgctg      1860
actgtcaact gtagcatttt ttggggttac agtttgagca ggatatttgg tcctgtagtt      1920
tgctaacaca ccctgcagct ccaaaggttc cccaccaaca gcaaaaaaat gaaaatttga      1980
cccttgaatg ggttttccag caccattttc atgagttttt tgtgtccctg aatgcaagtt      2040
taacatagca gttaccccaa taacctcagt tttaacagta acagcttccc acatcaaaat      2100
atttccacag gttaagtcct catttaaatt aggcaaagga attcttgaag acgaagggc      2160 ctcgtgatac gcctattttt ataggttaat gtcatgataa taatggtttc ttagacgtca      2220
ggtggcactt ttcggggaaa tgtgcgcgga acccctattt gtttattttt ctaaatacat      2280
tcaaatatgt atccgctcat gagacaataa ccctgataaa tgcttcaata atattgaaaa      2340
aggaagagta tgagtattca acatttccgt gtcgccctta ttcccttttt tgcggcattt      2400
tgccttcctg ttttgctca cccagaaacg ctggtgaaag taaaagatgc tgaagatcag      2460
ttgggtgcac gagtgggtta catcgaactg gatctcaaca gcggtaagat ccttgagagt      2520
tttcgccccg aagaacgttt tccaatgatg agcactttta aagttctgct atgtggcgcg      2580
gtattatccc gtgttgacgc cgggcaagag caactcggtc gccgcataca ctattctcag      2640
aatgacttgg ttgagtactc accagtcaca gaaaagcatc ttacggatgg catgacagta      2700
```

-continued

```
agagaattat gcagtgctgc cataaccatg agtgataaca ctgcggccaa cttacttctg    2760
acaacgatcg gaggaccgaa ggagctaacc gcttttttgc acaacatggg ggatcatgta    2820
actcgccttg atcgttggga accggagctg aatgaagcca taccaaacga cgagcgtgac    2880
accacgatgc ctgcagcaat ggcaacaacg ttgcgcaaac tattaactgg cgaactactt    2940
actctagctt cccggcaaca attaatagac tggatggagg cggataaagt tgcaggacca    3000
cttctgcgct cggcccttcc ggctggctgg tttattgctg ataaatctgg agccggtgag    3060
cgtgggtctc gcggtatcat tgcagcactg gggccagatg gtaagccctc ccgtatcgta    3120
gttatctaca cgacggggag tcaggcaact atggatgaac gaaatagaca gatcgctgag    3180
ataggtgcct cactgattaa gcattggtaa ctgtcagacc aagtttactc atatatactt    3240
tagattgatt taaaacttca ttttttaattt aaaaggatct aggtgaagat ccttttttgat    3300 aatctcatga ccaaaatccc ttaacgtgag ttttcgttcc actgagcgtc agaccccgta    3360
gaaaagatca aaggatcttc ttgagatcct ttttttctgc gcgtaatctg ctgcttgcaa    3420
acaaaaaaac caccgctacc agcggtggtt tgtttgccgg atcaagagct accaactctt    3480
tttccgaagg taactggctt cagcagagcg cagataccaa atactgtcct tctagtgtag    3540
ccgtagttag gccaccactt caagaactct gtagcaccgc ctacatacct cgctctgcta    3600
atcctgttac cagtggctgc tgccagtggc gataagtcgt gtcttaccgg gttggactca    3660
agacgatagt taccggataa ggcgcagcgg tcgggctgaa cggggggttc gtgcacacag    3720
cccagcttgg agcgaacgac ctacaccgaa ctgagatacc tacagcgtga gctatgagaa    3780
agcgccacgc ttcccgaagg gagaaaggcg gacaggtatc cggtaagcgg cagggtcgga    3840
acaggagagc gcacgaggga gcttccaggg ggaaacgcct ggtatcttta tagtcctgtc    3900
gggtttcgcc acctctgact tgagcgtcga ttttgtgat gctcgtcagg ggggcggagc    3960
ctatggaaaa acgccagcaa cgcggccttt ttacggttcc tggccttttg ctggcctttt    4020
gctcacatgt tctttcctgc gttatcccct gattctgtgg ataaccgtat taccgccttt    4080
gagtgagctg ataccgctcg ccgcagccga acgaccgagc gcagcgagtc agtgagcgag    4140
gaagcggaag agcgcctgat gcggtatttt ctccttacgc atctgtgcgg tatttcacac    4200
cgcatatggt gcactctcag tacaatctgc tctgatgccg catagttcag ctgagtggat    4260
tcgcgggcac agacgcccag gaccgcgctt cccacgtggc ggagggactg gggacccggg    4320
cacccgtcct gccccttcac cttccagctc cgcctcctcc gcgcggaccc cgccccgtcc    4380 cgaccctcc cgggtcccg gcccagcccc ctcgggccc tcccagcccc tccccttcct    4440
ttccgcggcc ccgccctctc ctcgcgcgcg gagtttcagg cagcgctgcg tcctgctgcg    4500
cacgtgggaa gccctggccc cggccacccc gcgggccgg cccgccacca tggcctccta    4560
cccatgccac cagcatgcat ctgccttcga ccaggccgct agatcaaggg gccacagcaa    4620
ccggagaacc gccctgaggc ccaggcgcca gcaggaggct accgaagtgc gccctgagca    4680
gaagatgcca acactgctgc gagtctatat cgatggccct catgggatgg aaaaaccac    4740 aactacccag ctgctggtgg ccctggggtc ccgggacgac atcgtgtacg tccctgagcc    4800
aatgacttat tggagagtgc tggggcctc tgaaaccatc gctaatatct acacaactca    4860
gcaccgcctg gaccagggag agatcagcgc cggcgatgca gccgtggtca tgacctccgc    4920
acagattaca atgggaatgc cttatgccgt gaccgacgcc gtcctggctc cacacatcgg    4980
aggagaagca ggcagctccc atgcaccacc tccagccctg acaatcttcc tggataggca    5040
cccaattgct tttatgctgt gctaccccgc tgcacgctat ctgatgggca gcatgacccc    5100
```

```
acaggcagtg ctggcctttg tcgctctgat ccccccctaca ctgcccggga ctaacattgt    5160
gctgggagct ctgcctgagg acaggcatat cgatcgactg gcaaagcgac agcgaccagg    5220
agaacggctg gacctggcaa tgctggccgc tattcgacgg gtgtacggac tgctggctaa    5280
caccgtgaga tacctgcagt gtggaggcag ttggagggag gactggggac agctgtcagg    5340
gactgccgtg ccaccacagg gagctgaacc tcagagtaat gcaggccccc ggcctcacat    5400
cggggatact ctgttcaccc tgtttagagc acccgagctg ctggccccta acggagacct    5460
gtacaacgtg ttcgcttggg cactggatgt cctggccaaa cggctgcgga gcatgcacgt    5520
gtttattctg gactatgatc agagtcccgc tggctgtagg gatgcactgc tgcagctgac    5580
ttcaggaatg gtgcagaccc atgtcaccac accaggcagc atccccacaa tttgcgacct    5640
ggctcgaact ttcgcacggt ctagtgattg tgccttttga ttgccagcca tctgttgttt    5700
gcccctcccc cgtgccttcc ttgaccctgg aaggtgccac tcccactgtc ctttcctaat    5760
aaaatgagga aattgcatcg cattgtctga gtaggtgtca ttctattctg ggggtgggg    5820 tggggcagga cagcaagggg gaggattggg aagacaatag caggcatgct ggggatgcgg    5880
tgggctctat ggctctgtat accgtcgacc tctagctaga gctggcgcgc cgggacaggg    5940
gtgtggggac aggggtctgg ggacagggt gtggggacag gggtcctggg gacaggggtg    6000
tgggataggg ggtgtgggga caggggtgtg gggacagggg tgtggggaca ggggtctggg    6060
gacagcagcg caaagagccc cgccctgcag cctccagctc tcctggtcta atgtggaaag    6120 tgcccaggt gagggctttg ctctcctgga gacatttgcc cccagctgtg agcagggaca    6180
ggtctggcca ccgggcccct ggttaagact ctaatgaccc gctggtcctg aggaagaggt    6240
gctgacgacc aaggagatct tcccacagac ccagcaccag ggaaatggtc cggaggcaaa    6300
gaattctgag ccgccaccat ggccaattta ctgaccgtgc accagaatct gccagctctg    6360
cccgtggacg caacatctga tgaggtccgg aagaacctga tggacatgtt ccgagatcgg    6420
caggccttta gtgaacatac ctggaaaatg ctgctgtcag tgtgccgaag ctgggccgct    6480
tggtgtaagc tgaacaatag aaaatggttc cctgccgagc cagaagacgt gcgcgattac    6540
ctgctgtatc tgcaggcccg agggctggct gtcaagacaa ttcagcagca cctggggcag    6600
ctgaatatgc tgcatcggag aagcggactg cccaggccta gcgactccaa tgccgtgtcc    6660
ctggtcatga ggcgcatccg gaaggagaac gtggatgcag gcgaaagagc caaacaggcc    6720
ctggctttcg agagaactga ctttgatcag gtgaggtccc tgatggaaaa ctctgacagg    6780
tgccaggata ttcgcaatct ggcctttctg ggaatcgctt acaacacact gctgcgcatc    6840
gctgagattg caagaatcag ggtgaaggac atttcccgaa ctgatggcgg cagaatgctg    6900
atccacattg gccggaccaa aacactggtg agtacagcag gagtcgagaa ggccctgtca    6960
ctgggcgtga ctaaactggt cgaaagatgg atctctgtga gtggcgtcgc agacgatccc    7020
aacaattatc tgttctgtcg cgtgcgaaag aacggggtcg cagccccttc agctactagc    7080
cagctgtcca ccagggccct ggagggaatt tttgaagcta cacaccgcct gatctacggg    7140
gccaaagacg attctggaca gaggtatctg gcttggtctg acatagtgc acgcgtggga    7200 gctgcacggg acatggcaag agccggcgtc agcattcccg agatcatgca ggccggaggc    7260
tggactaacg tgaatattgt catgaactac atcagaaatc tggatagcga aaccggggct    7320
atggtgcgcc tgctgaaaga tggcgatgga ccggtgaac aaaaaactat ttctgaagaa    7380
gatctgtgat acctcaggct aagcgtgcag gctgcctatc agaaggtggt ggctggtgtg    7440
```

```
gccaatgccc tggctcacaa ataccactga gatctttttc cctctgccaa aaattatggg    7500
gacatcatga agccccttga gcatctgact tctggctaat aaaggaaatt tattttcatt    7560
gcaatagtgt gttggaattt tttgtgtctc tcactcggaa ggacatatgg agggcaaat    7620 catttaaaac atcagaatga gtatttggtt tagagtttgg caacatatgc catatgctgg    7680
ctgccatgaa caaggtggc tataaagagg tcatcagtat atgaaacagc ccctgctgt     7740 ccattcctta ttccatagaa aagccttgac ttgaggttag attttttta tattttgttt    7800 tgtgttattt ttttctttaa catccctaaa attttcctta catgttttac tagccacagc    7860
tg                                                                   7862

<210> SEQ ID NO 3
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: M13 Fwd of SEQ ID NO: 1 (pUC57LoxNRNeoRLox)

<400> SEQUENCE: 3
gtaaaacgac ggccagt                                                   17

<210> SEQ ID NO 4
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: LoxP of SEQ ID NO: 1 (pUC57LoxNRNeoRLox)

<400> SEQUENCE: 4
ataacttcgt atagcataca ttatacgaag ttat                                34

<210> SEQ ID NO 5
<211> LENGTH: 380
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: CMV Enhancer of SEQ ID NO: 1
      (pUC57LoxNRNeoRLox)

<400> SEQUENCE: 5
gacattgatt attgactagt tattaatagt aatcaattac gggtcatta gttcatagcc      60 catatatgga gttccgcgtt acataactta cggtaaatgg cccgcctggc tgaccgccca    120 acgaccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgccccta ttgacgtcaa tgacggtaaa tggcccgcct    300
ggcattatgc ccagtacatg acctatggg actttcctac ttggcagtac atctacgtat    360
tagtcatcgc tattaccatg                                               380

<210> SEQ ID NO 6
<211> LENGTH: 204
<212> TYPE: DNA
<213> ORGANISM: Artificial Sequence
```

<220> FEATURE:
<223> OTHER INFORMATION: Synthetic polynucleotide
<220> FEATURE:
<221> NAME/KEY: misc_feature
<223> OTHER INFORMATION: CMV promoter of SEQ ID NO: 1
      (pUC57LoxNRNeoRLox)

<400> SEQUENCE: 6
gtgatgcggt tttggcagta catcaatggg cgtggatagc ggtttgactc acggggattt     60
ccaagtctcc accccattga cgtcaatggg agtttgtttt ggcaccaaaa tcaacgggac    120
tttccaaaat gtcgtaacaa ctccgcccca ttgacgcaaa tgggcggtag cgtgtacgg    180 tgggaggtct atataagcag agct                                            204

<210> SEQ ID NO 7
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: T7 Promoter of SEQ ID NO: 1 (pUC57LoxNRNeoRLox)

<400> SEQUENCE: 7
taatacgact cactatagg                                                  19

<210> SEQ ID NO 8
<211> LENGTH: 509
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Codon Optimized Nitroreductase for efficient
      mammalian translation of SEQ ID NO: 1 (pUC57LoxNRNeoRLox)

<400> SEQUENCE: 8
actaaagcat tcgatgcctc caagaaactg actcccgagc aggctgaaca gatcaagacc     60
ctgctgcagt actctccaag ctccctgaac agtcagccct ggcactttat tgtggcctct    120
acagaggaag gaaaggctag ggtggcaaaa tctgccgctg gcaattacgt gttcagcgag    180
cgcaagatgc tggacgcctc acatgtggtc gtgttttgcg ccaagaccgc tatgacgac    240 gtgtggctga aactggtcgt ggaccaggag gacgccgatg ggagattcgc aacacctgaa    300
gccaaagcag ccaacgataa gggacggaaa ttctttgccg acatgcacag aaaggatctg    360
catgacgatg ctgagtggat ggcaaaacag gtgtacctga acgtcggcaa ttttctgctg    420
ggagtggctg cactgggact ggacgccgtc cctatcgaag cttcgacgc cgctattctg    480 gatgctgagt ttggcctgaa ggaaaaaagg                                     509

<210> SEQ ID NO 9
<211> LENGTH: 225
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: bGH poly(A) signal of SEQ ID NO: 1
      (pUC57LoxNRNeoRLox)

<400> SEQUENCE: 9
ctgtgccttc tagttgccag ccatctgttg tttgcccctc ccccgtgcct tccttgaccc     60

```
tggaaggtgc cactcccact gtcctttcct aataaaatga ggaaattgca tcgcattgtc      120
tgagtaggtg tcattctatt ctgggggtg gggtggggca ggacagcaag ggggaggatt       180
gggaagacaa tagcaggcat gctggggatg cggtgggctc tatgg                     225
```

<210> SEQ ID NO 10
<211> LENGTH: 429
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: f1 ori of SEQ ID NO: 1 (pUC57LoxNRNeoRLox)

<400> SEQUENCE: 10

```
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca     120
cgttcgccgg ctttccccgt caagctctaa atcgggggct cccttagggg ttccgattta    180
gtgctttacg gcacctcgac cccaaaaaac ttgattaggg tgatggttca cgtagtgggc    240
catcgcccta tagacggtt tttcgccctt tgacgttgga gtccacgttc tttaatagtg     300
gactcttgtt ccaaactgga acaacactca accctatctc ggtctattct tttgatttat    360
aagggatttt gccgatttcg gcctattggt taaaaaatga gctgatttaa caaaaattta    420
acgcgaatt                                                            429
```

<210> SEQ ID NO 11
<211> LENGTH: 330
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: SV40 promoter of SEQ ID NO: 1
       (pUC57LoxNRNeoRLox)

<400> SEQUENCE: 11

```
gtgtgtcagt tagggtgtgg aaagtcccca ggctccccag caggcagaag tatgcaaagc      60
atgcatctca attagtcagc aaccaggtgt ggaaagtccc caggctcccc agcaggcaga    120
agtatgcaaa gcatgcatct caattagtca gcaaccatag tcccgcccct aactccgccc    180
atcccgcccc taactccgcc cagttccgcc cattctccgc cccatggctg actaattttt    240
tttatttatg cagaggccga ggccgcctct gcctctgagc tattccagaa gtagtgagga    300
ggcttttttg gaggcctagg cttttgcaaa                                     330
```

<210> SEQ ID NO 12
<211> LENGTH: 795
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Neomycin resistance gene Aminoglycoside
       phosphotransferase from Tn5 of SEQ ID NO: 1 (pUC57LoxNRNeoRLox)

<400> SEQUENCE: 12

```
atgattgaac aagatggatt gcacgcaggt tctccggccg cttgggtgga gaggctattc      60
ggctatgact gggcacaaca gacaatcggc tgctctgatg ccgccgtgtt ccggctgtca    120
```

```
gcgcagggc  gcccggttct  ttttgtcaag  accgacctgt  ccggtgccct  gaatgaactg    180
caggacgagg  cagcgcggct  atcgtggctg  gccacgacgg  gcgttccttg  cgcagctgtg    240
ctcgacgttg  tcactgaagc  gggaagggac  tggctgctat  tgggcgaagt  gccggggcag    300
gatctcctgt  catctcacct  tgctcctgcc  gagaaagtat  ccatcatggc  tgatgcaatg    360
cggcggctgc  atacgcttga  tccggctacc  tgcccattcg  accaccaagc  gaaacatcgc    420
atcgagcgag  cacgtactcg  gatggaagcc  ggtcttgtcg  atcaggatga  tctggacgaa    480
gagcatcagg  ggctcgcgcc  agccgaactg  ttcgccaggc  tcaaggcgcg  catgcccgac    540
ggcgaggatc  tcgtcgtgac  ccatggcgat  gcctgcttgc  cgaatatcat  ggtggaaaat    600
ggccgctttt  ctggattcat  cgactgtggc  cggctgggtg  tggcggaccg  ctatcaggac    660
atagcgttgg  ctacccgtga  tattgctgaa  gagcttggcg  gcgaatgggc  tgaccgcttc    720
ctcgtgcttt  acggtatcgc  cgctcccgat  tcgcagcgca  tcgccttcta  tcgccttctt    780
gacgagttct  tctga                                                          795

<210> SEQ ID NO 13
<211> LENGTH: 122
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: SV40 poly(A) signal of SEQ ID NO: 1
      (pUC57LoxNRNeoRLox)

<400> SEQUENCE: 13
aacttgttta  ttgcagctta  taatggttac  aaataaagca  atagcatcac  aaatttcaca     60
aataaagcat  ttttttcact  gcattctagt  tgtggtttgt  ccaaactcat  caatgtatct    120
ta                                                                        122

<210> SEQ ID NO 14
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: LoxP of SEQ ID NO: 1 (pUC57LoxNRNeoRLox)

<400> SEQUENCE: 14
ataacttcgt  atagcataca  ttatacgaag  ttat                                   34

<210> SEQ ID NO 15
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: M13rev of SEQ ID NO: 1 (pUC57LoxNRNeoRLox)

<400> SEQUENCE: 15
gtcatagctg  tttcctg                                                        17

<210> SEQ ID NO 16
<211> LENGTH: 17
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Lac operator of SEQ ID NO: 1
      (pUC57LoxNRNeoRLox)

<400> SEQUENCE: 16
ttgttatccg ctcacaa                                                     17

<210> SEQ ID NO 17
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Lac promoter of SEQ ID NO: 1
      (pUC57LoxNRNeoRLox)

<400> SEQUENCE: 17
caacatacga gccggaagca taaagtgtaa a                                     31

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: CAP binding site of SEQ ID NO: 1
      (pUC57LoxNRNeoRLox)

<400> SEQUENCE: 18
atgagtgagc taactcacat ta                                               22

<210> SEQ ID NO 19
<211> LENGTH: 589
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Ori seq of SEQ ID NO: 1 (pUC57LoxNRNeoRLox)

<400> SEQUENCE: 19
tttccatagg ctccgccccc ctgacgagca tcacaaaaat cgacgctcaa gtcagaggtg       60
gcgaaacccg acaggactat aaagatacca ggcgtttccc cctggaagct ccctcgtgcg      120
ctctcctgtt ccgaccctgc cgcttaccgg atacctgtcc gcctttctcc cttcgggaag      180
cgtggcgctt tctcatagct cacgctgtag gtatctcagt tcggtgtagg tcgttcgctc      240
caagctgggc tgtgtgcacg aaccccccgt tcagcccgac cgctgcgcct tatccggtaa      300
ctatcgtctt gagtccaacc cggtaagaca cgacttatcg ccactggcag cagccactgg      360
taacaggatt agcagagcga ggtatgtagg cggtgctaca gagttcttga agtggtggcc      420
taactacggc tacactagaa gaacagtatt tggtatctgc gctctgctga gccagttac       480 cttcggaaaa agagttggta gctcttgatc cggcaacaa accaccgctg gtagcggtgg       540
tttttttgtt tgcaagcagc agattacgcg cagaaaaaaa ggatctcaa                 589

<210> SEQ ID NO 20
```

```
<211> LENGTH: 861
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Ampicillin resistance gene Beta-lactamase of
      SEQ ID NO: 1 (pUC57LoxNRNeoRLox)

<400> SEQUENCE: 20
ttaccaatgc ttaatcagtg aggcacctat ctcagcgatc tgtctatttc gttcatccat      60
agttgcctga ctccccgtcg tgtagataac tacgatacgg gagggcttac catctggccc     120
cagtgctgca atgataccgc gagacccacg ctcaccggct ccagatttat cagcaataaa     180
ccagccagcc ggaagggccg agcgcagaag tggtcctgca actttatccg cctccatcca     240
gtctattaat tgttgccggg aagctagagt aagtagttcg ccagttaata gtttgcgcaa     300
cgttgttgcc attgctacag gcatcgtggt gtcacgctcg tcgtttggta tggcttcatt     360
cagctccggt tcccaacgat caaggcgagt tacatgatcc cccatgttgt gcaaaaaagc     420
ggttagctcc ttcggtcctc cgatcgttgt cagaagtaag ttggccgcag tgttatcact     480
catggttatg gcagcactgc ataattctct tactgtcatg ccatccgtaa gatgcttttc     540
tgtgactggt gagtactcaa ccaagtcatt ctgagaatag tgtatgcggc gaccgagttg     600
ctcttgcccg gcgtcaatac gggataatac cgcgccacat agcagaactt taaaagtgct     660
catcattgga aaacgttctt cggggcgaaa actctcaagg atcttaccgc tgttgagatc     720
cagttcgatg taacccactc gtgcacccaa ctgatcttca gcatctttta ctttcaccag     780
cgtttctggg tgagcaaaaa caggaaggca aaatgccgca aaaaagggaa taagggcgac     840
acggaaatgt tgaatactca t                                              861

<210> SEQ ID NO 21
<211> LENGTH: 105
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Amp promoter of SEQ ID NO: 1
      (pUC57LoxNRNeoRLox)

<400> SEQUENCE: 21
actcttcctt tttcaatatt attgaagcat ttatcagggt tattgtctca tgagcggata      60
catatttgaa tgtatttaga aaaataaaca ataggggtt ccgcg                      105

<210> SEQ ID NO 22
<211> LENGTH: 330
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: SV40 Promoter of SEQ ID NO: 2
      (pPURHtertpTKHipCre)

<400> SEQUENCE: 22
gtgtgtcagt tagggtgtgg aaagtcccca ggctccccag caggcagaag tatgcaaagc      60
atgcatctca attagtcagc aaccaggtgt ggaaagtccc caggctcccc agcaggcaga     120
agtatgcaaa gcatgcatct caattagtca gcaaccatag tcccgcccct aactccgccc     180
```

-continued

```
atcccgcccc taactccgcc cagttccgcc cattctccgc cccatggctg actaatttttt    240 tttatttatg cagaggccga ggccgcctcg gcctctgagc tattccagaa gtagtgagga    300
ggcttttttg gaggcctagg cttttgcaaa                                      330
```

<210> SEQ ID NO 23
<211> LENGTH: 600
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Puromycin resistance gene Puromycin N-acetyl
      transferase of SEQ ID NO: 2 (pPURHtertpTKHipCre)

<400> SEQUENCE: 23

```
atgaccgagt acaagcccac ggtgcgcctc gccacccgcg acgacgtccc ccgggccgta     60
cgcaccctcg ccgccgcgtt cgccgactac cccgccacgc gccacaccgt cgacccggac    120
cgccacatcg agcgggtcac cgagctgcaa gaactcttcc tcacgcgcgt cggggctcgac   180 atcggcaagg tgtgggtcgc ggacgacggc gccgcggtgg cggtctggac cacgccggag    240
agcgtcgaag cggggggcggt gttcgccgag atcggcccgc gcatggccga gttgagcggt    300
tcccggctgg ccgcgcagca acagatggaa ggcctcctgg cgccgcaccg gcccaaggag    360
cccgcgtggt tcctggccac cgtcggcgtc tcgcccgacc accagggcaa gggtctgggc    420
agcgccgtcg tgctccccgg agtggaggcg gccgagcgcg ccggggtgcc cgccttcctg    480
gagacctccg cgccccgcaa cctcccccttc tacgagcggc tcggcttcac cgtcaccgcc    540
gacgtcgagt gcccgaagga ccgcgcgacc tggtgcatga cccgcaagcc cggtgcctga    600
```

<210> SEQ ID NO 24
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: SV40 poly(A) signal of SEQ ID NO: 2
      (pPURHtertpTKHipCre)

<400> SEQUENCE: 24

```
aacttgttta ttgcagctta taatggttac aaataaagca atagcatcac aaatttcaca     60
aataaagcat ttttttcact gcattctagt tgtggtttgt ccaaactcat caatgtatct    120
tatcatgtct ggatc                                                      135
```

<210> SEQ ID NO 25
<211> LENGTH: 105
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AmpR promoter of SEQ ID NO: 2
      (pPURHtertpTKHipCre)

<400> SEQUENCE: 25

```
cgcggaaccc ctatttgttt attttttctaa atacattcaa atatgtatcc gctcatgaga    60
caataaccct gataaatgct tcaataatat tgaaaaagga agagt                    105
```

<210> SEQ ID NO 26
<211> LENGTH: 861
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Ampicillin resistance gene Beta lactamase of
SEQ ID NO: 2 (pPURHtertpTKHipCre)

<400> SEQUENCE: 26

```
atgagtattc aacatttccg tgtcgccctt attcccttttt ttgcggcatt ttgccttcct      60
gtttttgctc acccagaaac gctggtgaaa gtaaaagatg ctgaagatca gttgggtgca     120
cgagtgggtt acatcgaact ggatctcaac agcggtaaga tccttgagag ttttcgcccc     180
gaagaacgtt ttccaatgat gagcactttt aaagttctgc tatgtggcgc ggtattatcc     240
cgtgttgacg ccgggcaaga gcaactcggt cgccgcatac actattctca gaatgacttg     300
gttgagtact caccagtcac agaaaagcat cttacggatg gcatgacagt aagagaatta     360
tgcagtgctg ccataaccat gagtgataac actgcggcca acttacttct gacaacgatc     420
ggaggaccga aggagctaac cgcttttttg cacaacatgg gggatcatgt aactcgcctt     480
gatcgttggg aaccggagct gaatgaagcc ataccaaacg acgagcgtga ccacgatg      540
cctgcagcaa tggcaacaac gttgcgcaaa ctattaactg gcgaactact tactctagct     600
tcccggcaac aattaataga ctggatggag gcggataaag ttgcaggacc acttctgcgc     660
tcggcccttc cggctggctg gtttattgct gataaatctg gagccggtga gcgtgggtct     720
cgcggtatca ttgcagcact ggggccagat ggtaagccct cccgtatcgt agttatctac     780
acgacgggga gtcaggcaac tatggatgaa cgaaatagac agatcgctga gataggtgcc     840
tcactgatta agcattggta a                                                861
```

<210> SEQ ID NO 27
<211> LENGTH: 589
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Ori seq of SEQ ID NO: 2 (pPURHtertpTKHipCre)

<400> SEQUENCE: 27

```
ttgagatcct ttttttctgc gcgtaatctg ctgcttgcaa acaaaaaaac caccgctacc      60
agcggtggtt tgtttgccgg atcaagagct accaactctt tttccgaagg taactggctt     120
cagcagagcg cagataccaa atactgtcct tctagtgtag ccgtagttag gccaccactt     180
caagaactct gtagcaccgc ctacatacct cgctctgcta atcctgttac cagtggctgc     240
tgccagtggc gataagtcgt gtcttaccgg gttggactca agacgatagt taccggataa     300
ggcgcagcgg tcgggctgaa cggggggttc gtgcacacag cccagcttgg agcgaacgac     360
ctacaccgaa ctgagatacc tacagcgtga gctatgagaa agcgccacgc ttcccgaagg     420
gagaaaggcg gacaggtatc cggtaagcgg cagggtcgga acaggagagc gcacgaggga     480
gcttccaggg ggaaacgcct ggtatcttta tagtcctgtc gggtttcgcc acctctgact     540
tgagcgtcga tttttgtgat gctcgtcagg gggcggagc ctatggaaa                  589
```

<210> SEQ ID NO 28

<211> LENGTH: 281
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: hTERTp of SEQ ID NO: 2 (pPURHtertpTKHipCre)

<400> SEQUENCE: 28

```
agtggattcg cgggcacaga cgcccaggac cgcgcttccc acgtggcgga gggactgggg      60
acccgggcac ccgtcctgcc ccttcacctt ccagctccgc ctcctccgcg cggaccccgc     120
cccgtcccga cccctcccgg gtccccggcc cagccccctc cgggccctcc cagcccctcc     180
ccttcctttc gcggccccg  ccctctcctc gcggcgcgag tttcaggcag cgctgcgtcc     240
tgctgcgcac gtgggaagcc ctggccccgg ccaccccgc g                          281
```

<210> SEQ ID NO 29
<211> LENGTH: 1115
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Herpes Simplex Virus Thymidine Kinase gene
      codon optimized for mammalian transalation of SEQ ID NO: 2
      (pPURHtertpTKHipCre)

<400> SEQUENCE: 29

```
atggcctcct acccatgcca ccagcatgca tctgccttcg accaggccgc tagatcaagg      60
ggccacagca accggagaac cgccctgagg cccaggcgcc agcaggaggc taccgaagtg     120
cgccctgagc agaagatgcc aacactgctg cgagtctata tcgatggccc tcatgggatg     180
ggaaaaacca caactaccca gctgctggtg gccctggggt cccgggacga catcgtgtac     240
gtccctgagc caatgactta ttggagagtg ctggggcct  ctgaaaccat cgctaatatc     300
tacacaactc agcaccgcct ggaccaggga gagatcagcg ccggcgatgc agccgtggtc     360
atgacctccg cacagattac aatgggaatg ccttatgccg tgaccgacgc cgtcctggct     420
ccacacatcg gaggagaagc aggcagctcc catgcaccac ctccagccct gacaatcttc     480
ctggataggc acccaattgc ttttatgctg tgctaccccg ctgcacgcta tctgatgggc     540
agcatgaccc cacaggcagt gctggccttt gtcgctctga tcccccctac actgcccggg     600
actaacattg tgctgggagc tctgcctgag gacaggcata tcgatcgact ggcaaagcga     660
cagcgaccag gagaacggct ggacctggca atgctggccg ctattcgacg ggtgtacgga     720
ctgctggcta acaccgtgag atacctgcag tgtggaggca gttggaggga ggactgggga     780
cagctgtcag ggactgccgt gccaccacag ggagctgaac ctcagagtaa tgcaggcccc     840
cggcctcaca tcggggatac tctgttcacc ctgtttagag cacccgagct gctggcccct     900
aacggagacc tgtacaacgt gttcgcttgg gcactggatg tcctggccaa acggctgcgg     960
agcatgcacg tgtttattct ggactatgat cagagtcccg ctggctgtag ggatgcactg    1020
ctgcagctga cttcaggaat ggtgcagacc catgtcacca caccaggcag catccccaca    1080
atttgcgacc tggctcgaac tttcgcacgg tctag                                1115
```

<210> SEQ ID NO 30
<211> LENGTH: 232
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: misc_feature
<223> OTHER INFORMATION: Bi-allelic poly(A) trap vector of SEQ ID NO: 2
      (pPURHtertpTKHipCre)

<400> SEQUENCE: 30
gattgtgcct tttgattgcc agccatctgt tgtttgcccc tcccccgtgc cttccttgac    60
cctggaaggt gccactccca ctgtcctttc ctaataaaat gaggaaattg catcgcattg   120
tctgagtagg tgtcattcta ttctgggggg tggggtgggg caggacagca agggggagga   180
ttgggaagac aatagcaggc atgctgggga tgcggtgggc tctatggctc tg           232

<210> SEQ ID NO 31
<211> LENGTH: 266
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Human Insulin Promoter of SEQ ID NO: 2
      (pPURHtertpTKHipCre)

<400> SEQUENCE: 31
gacaggggtg tggggacagg ggtctgggga cagcagcgca aagagccccg ccctgcagcc    60
tccagctctc ctggtctaat gtggaaagtg gcccaggtga gggctttgct ctcctggaga   120
catttgcccc cagctgtgag cagggacagg tctggccacc gggcccctgg ttaagactct   180
aatgacccgc tggtcctgag gaagaggtgc tgacgaccaa ggagatcttc ccacagaccc   240
agcaccaggg aaatggtccg gaggca                                        266

<210> SEQ ID NO 32
<211> LENGTH: 1028
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Cre recombinase of SEQ ID NO: 2
      (pPURHtertpTKHipCre)

<400> SEQUENCE: 32
ccaatttact gaccgtgcac cagaatctgc cagctctgcc cgtggacgca acatctgatg    60
aggtccggaa gaacctgatg gacatgttcc gagatcggca ggcctttagt gaacatacct   120
ggaaaatgct gctgtcagtg tgccgaagct gggccgcttg gtgtaagctg aacaatagaa   180
aatggttccc tgccgagcca gaagacgtgc gcgattacct gctgtatctg caggcccgag   240
ggctggctgt caagacaatt cagcagcacc tggggcagct gaatatgctg catcggagaa   300
gcggactgcc caggcctagc gactccaatg ccgtgtccct ggtcatgagg cgcatccgga   360
aggagaacgt ggatgcaggc gaaagagcca acaggcccgg gctttcgag agaactgact   420 ttgatcaggt gaggtccctg atggaaaact ctgacaggtg ccaggatatt cgcaatctgg   480
cctttctggg aatcgcttac aacacactgc tgcgcatcgc tgagattgca gaatcagggg   540
tgaaggacat ttcccgaact gatggcggca gaatgctgat ccacattggc cggaccaaaa   600
cactggtgag tacagcagga gtcgagaagg ccctgtcact gggcgtgact aaactggtcg   660
aaagatggat ctctgtgagt ggcgtcgcag acgatcccaa caattatctg ttctgtcgcg   720
```

```
tgcgaaagaa cggggtcgca gcccctthcag ctactagcca gctgtccacc agggccctgg        780
agggaatttt tgaagctaca caccgcctga tctacggggc caaagacgat tctggacaga        840
ggtatctggc ttggtctgga catagtgcac gcgtgggagc tgcacgggac atggcaagag        900
ccggcgtcag cattcccgag atcatgcagg ccggaggctg gactaacgtg aatattgtca        960
tgaactacat cagaaatctg gatagcgaaa ccggggctat ggtgcgcctg ctggaagatg       1020
gcgatgga                                                                1028

<210> SEQ ID NO 33
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Myc of SEQ ID NO: 2 (pPURHtertpTKHipCre)

<400> SEQUENCE: 33
gaacaaaaac ttatttctga agaagatctg                                          30

<210> SEQ ID NO 34
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Beta-globin poly(A) signal of SEQ ID NO: 2
      (pPURHtertpTKHipCre)

<400> SEQUENCE: 34
aataaaggaa atttattttc attgcaatag tgtgttggaa ttttttgtgt ctctca             56

<210> SEQ ID NO 35
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: NTR forward primer

<400> SEQUENCE: 35
ccccacaggc agtgct                                                         16

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: NTR reverse primer

<400> SEQUENCE: 36
gttagtcccg ggcagtgtag                                                     20

<210> SEQ ID NO 37
<211> LENGTH: 16
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<223> OTHER INFORMATION: NTR FAM probe

<400> SEQUENCE: 37
ttgtcgctct gatccc                                                    16

<210> SEQ ID NO 38
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HSV-TK forward primer

<400> SEQUENCE: 38
ccaaagcagc caacgataag g                                              21

<210> SEQ ID NO 39
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HSV-TK reverse primer

<400> SEQUENCE: 39
ccatccactc agcatcgtca tg                                             22

<210> SEQ ID NO 40
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HSV-TK FAM probe

<400> SEQUENCE: 40
tcggcaaaga atttc                                                     15

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HSV-TK forward primer

<400> SEQUENCE: 41
cccgggacta acattgtgct                                                20

<210> SEQ ID NO 42
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HSV-TK reverse primer
```

```
<400> SEQUENCE: 42
cagctcgggt gctctaaaca                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: NTR forward primer

<400> SEQUENCE: 43
cctcacatgt ggtcgtgttt                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: NTR reverse primer

<400> SEQUENCE: 44
acctgttttg ccatccactc                                              20
```